US007943295B2

(12) United States Patent
Nakamura et al.

(10) Patent No.: US 7,943,295 B2
(45) Date of Patent: May 17, 2011

(54) SCREENING AND THERAPEUTIC METHOD FOR NSCLC TARGETING CDCA1-KNTC2 COMPLEX

(75) Inventors: Yusuke Nakamura, Bunkyo-ku (JP); Yataro Daigo, Bunkyo-ku (JP); Shuichi Nakatsuru, Kawasaki (JP)

(73) Assignee: Oncotherapy Science, Inc., Kanagawa (JP)

( * ) Notice: Subject to any disclaimer, the term of this patent is extended or adjusted under 35 U.S.C. 154(b) by 139 days.

(21) Appl. No.: 11/913,142

(22) PCT Filed: Jul. 19, 2006

(86) PCT No.: PCT/JP2006/314715

§ 371 (c)(1), (2), (4) Date: Jan. 28, 2009

(87) PCT Pub. No.: WO2007/013480

PCT Pub. Date: Feb. 1, 2007

(65) Prior Publication Data

US 2009/0215683 A1 Aug. 27, 2009

Related U.S. Application Data

(60) Provisional application No. 60/703,704, filed on Jul. 29, 2005.

(51) Int. Cl.
*C12Q 1/00* (2006.01)
*G01N 33/574* (2006.01)

(52) U.S. Cl. ................................ 435/4; 435/6; 435/7.23

(58) Field of Classification Search ........................ None
See application file for complete search history.

(56) References Cited

U.S. PATENT DOCUMENTS

| | | | | |
|---|---|---|---|---|
| 2002/0172952 | A1 * | 11/2002 | Henderson et al. | 435/6 |
| 2003/0211510 | A1 * | 11/2003 | Henderson et al. | 435/6 |
| 2006/0024692 | A1 | 2/2006 | Nakamura et al. | |
| 2007/0224201 | A1 * | 9/2007 | Wu et al. | 424/155.1 |

FOREIGN PATENT DOCUMENTS

| | | | |
|---|---|---|---|
| EP | 1 548 032 | A1 | 6/2005 |
| EP | 2 186 889 | A1 | 5/2010 |
| WO | WO 03/077875 | A2 | 10/2003 |
| WO | WO 2004/024766 | A1 | 3/2004 |
| WO | WO 2004/055050 | A2 | 7/2004 |
| WO | WO 2004/065577 | A2 | 8/2004 |
| WO | WO 2004/091548 | A2 | 10/2004 |
| WO | WO 2005/016962 | A2 | 2/2005 |
| WO | WO 2009/025117 | A1 | 2/2009 |

OTHER PUBLICATIONS

Sequence search result-Hendersen, 2010.*
Sequence search result (Henderson), 2010.*
Sequence search result (Sanicola-Nadel , 2010.*
Lin et al, Biochemistry USA, vol. 14, p. 1559-1563, 1975.*
Burgess et al, Journal of Cell biology, vol. 111, p. 2129-2138, 1990.*
Mesh term CDCA1, 2010.*
Hayama, S., et al., "Activation of CDCA1-KNTC2, members of centromere protein complex, involved in pulmonary carcinogenesis," *Cancer Research*, vol. 66(21), pp. 10339-10348 (Nov. 1, 2006).
Harao, M., et al., "Development of cancer immunotherapy directed against CDCA1 which is a novel cancer testis antigen highly expressed in lung cancer," Abstract of the *12th Annual Meeting of the Society for Fundamental Cancer Immunology*, p. 34 (Jun. 13, 2008).
Harao, M., et al., "CDCA1, a novel cancer-testis antigen useful for immunotherapy of lung cancer," Abstract of the *66th Annual Meeting of Luno Cancer*, pp. 163-164, Abstract # P294 (Jan. 1, 2007).
Harao, M., "Cell division cycle associated 1, an ideal lung cancer antigen for immunotherapy, identified using cDNA microarray analysis," Doctor's Thesis, 49 pgs. (Apr. 21, 2008).
Harao, M., et al., "HLA-A2-restricted CTL epitopes of a novel lung cancer-associated cancer testis antigen, cell division cycle associated 1, can induce tumor-reactive CTL," *Int. J. Cancer*, vol. 123(11), pp. 2616-2625 (Dec. 1, 2008).
Harao, M., et al., "CDCA1, a novel cancer-testis antigen useful for immunotherapy of lung cancer," *J. Japan Surgical Society*, SF-077-1, (109), p. 282 (Apr. 25, 2008).
Kikuchi, T., et al., "Expression profiles of non-small cell lung cancers on cDNA microarrays: Identification of genes for prediction of lymph-node metastasis and sensitivity of anti-cancer drugs," *Oncogene*, vol. 22(14), pp. 2192-2205 (Apr. 10, 2003).
Satoshi, H., et al., "Isolation and characterization of a novel cancer-testis antigen IMS-CL54 that is frequently up-regulated in non-small cell lung cancer," *Nihon Gan Gakkai Shoroku*, (63), p. 54, Abstract #W-072 (Aug. 25, 2004).
Suzuki, C., et al., "Identification of COX17 as a Therapeutic Target for Non-Small Cell Lung Cancer," *Cancer Res.*, vol. 63(21), pp. 7038-7041 (Nov. 1, 2003).

* cited by examiner

*Primary Examiner* — Misook Yu
*Assistant Examiner* — Lei Yao
(74) *Attorney, Agent, or Firm* — Kilpatrick Townsend & Stockton LLP

(57) ABSTRACT

The present invention is based on the observation that the co-activation of CDCA1 and KNTC2, and their cognate interactions, play significant roles in lung-cancer progression and that methods of inhibiting the complex can be used to treat non-small-cell lung cancer.

3 Claims, 10 Drawing Sheets

Continuation of Fig. 1
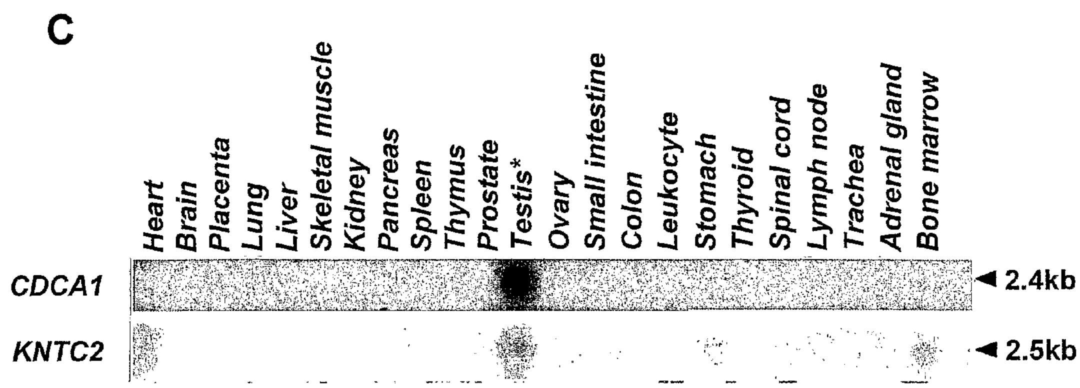

Continuation of Fig. 2
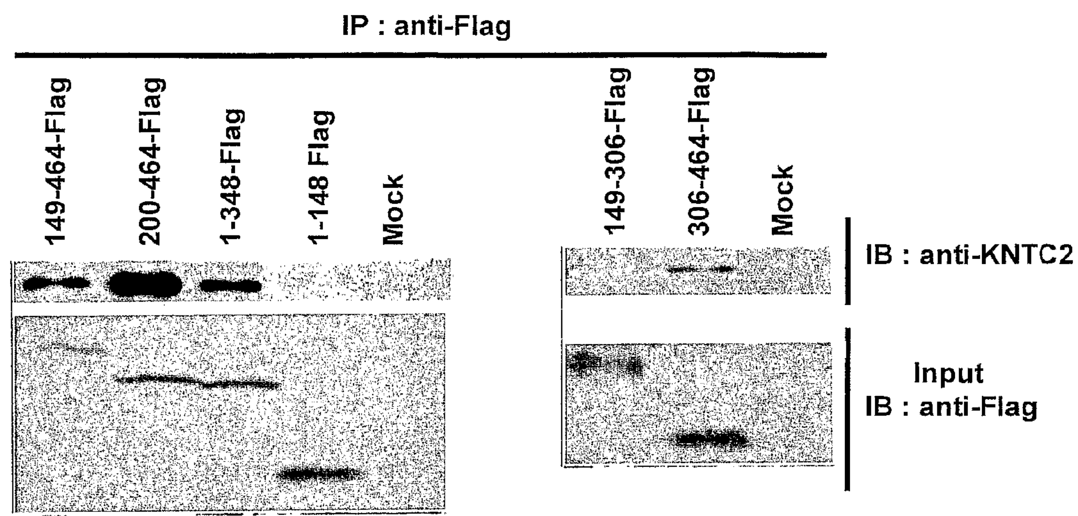
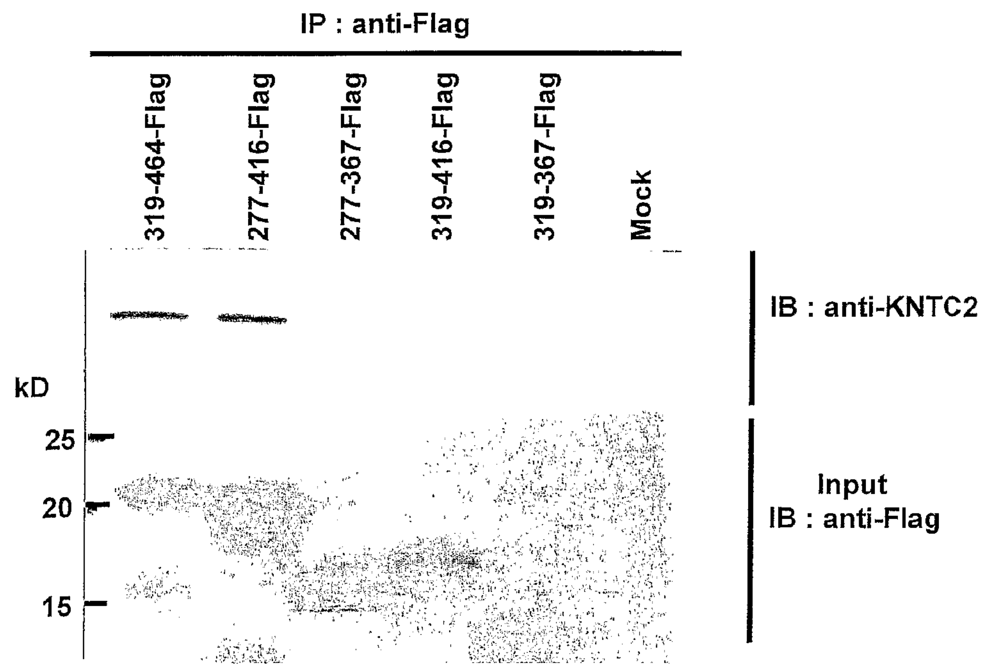

Continuation of Fig. 3
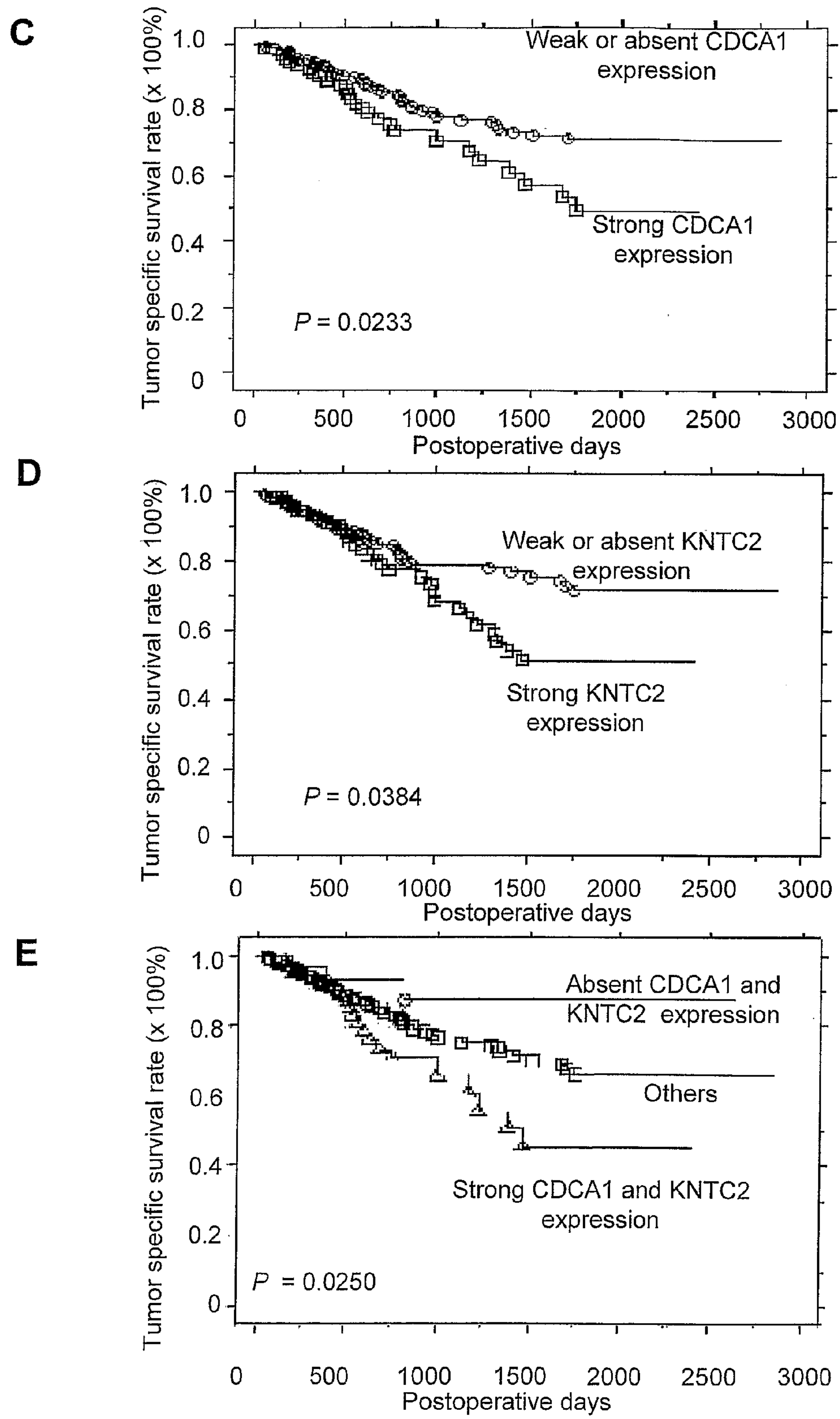

A Semi-quantitative RT-PCR

Colony -formation assay

B Semi-quantitative RT-PCR

Colony -formation assay

SCREENING AND THERAPEUTIC METHOD FOR NSCLC TARGETING CDCA1-KNTC2 COMPLEX

CROSS-REFERENCES TO RELATED APPLICATIONS

This application is a U.S. National Stage Application of PCT/JP2006/314715, filed Jul. 19, 2006, which claims the benefit of U.S. Provisional Application Ser. No. 60/703,704 filed Jul. 29, 2005, all of which are hereby incorporated by reference in their entirety.

FIELD OF THE INVENTION

This invention relates to the field of biological science, more specifically to the field of cancer therapy. In particular, the invention relates to the treatment of cancer based on the observation that the co-activation of CDCA1 and KNTC2, and their cognate interactions, play significant roles in lung-cancer progression and that methods of inhibiting the complex can be used to treat non-small-cell lung cancer.

BACKGROUND OF THE INVENTION

Lung cancer is one of the most common cancers in the world, and non-small-cell lung cancer (NSCLC) is by far the most common form, accounting for nearly 80% of those cases (Qreenlee R T., et al., CA Cancer J Clin. 2001; 51:15-36). Many genetic alterations associated with the development and progression of lung cancer have been reported. However, to date, the precise molecular mechanisms remain unclear (Sozzi G., Eur J Cancer. 2001; 37 Suppl 7:S63-73). Over the last decade newly developed cytotoxic agents, including paclitaxel, docetaxel, gemcitabine, and vinorelbine, have emerged to offer multiple therapeutic choices for patients with advanced NSCLC; however, those regimens provide only modest survival benefits compared with cisplatin-based therapies (Schiller J H, et al, N Engl J Med. 2002; 346:92-8; Kelly K, et al., J Clin Oncol. 2001; 19:3210-8). Hence, new therapeutic strategies are eagerly anticipated.

Systematic analysis of expression levels of thousands of genes using cDNA microarrays is an effective approach for identifying unknown molecules involved in pathways of carcinogenesis, and can reveal candidate target molecules for the development of novel therapeutics and diagnostics. The present inventors analyzed genome-wide expression profiles of NSCLC cells on a cDNA microarray containing 23,040 genes, using tumor-cell populations purified by laser microdissection, in an attempt to isolate potential molecular targets for diagnosis, treatment, and/or prevention of NSCLC (Kikuchi T, et al., Oncogene. 2003; 22:2192-205; Suzuki C, et al., Cancer Res. 2003; 63:7038-41; Kakiuchi S, et al., Mol Cancer Res. 2003; 1:485-99; Zembutsu H, et al., Int J Oncol. 2003; 23:29-39; Kakiuchi S, et al., Hum Mol Genet. 2004; 13:3029-43). To verify the biological and clinicopathological significance of the respective gene products, the present inventors have also performed tumor-tissue microarray analysis of clinical lung-cancer materials (Ishikawa N, et al., Clin Cancer Res. 2004; 10(24):8363-70). This systematic approach revealed that a cell division associated 1 (CDCA1) and a kinetocore associated 2 (KNTC2) were frequently co-over-expressed in primary NSCLCs (see also WO2004/031413).

Altered regulation of the cell cycle is a hallmark of human cancers. CDCA1 and KNTC2 are members of several proteins involved in spindle checkpoint signaling. Specifically, attachment sites within the kinetochore outer plate generate microtubule dependent forces for chromosome movement and regulate spindle checkpoint protein assembly at the kinetochore. The Ndc80 complex, composed of Ndc80 (Hec1), Nuf2, Spc24, and Spc25, is essential for metaphase chromosome alignment and anaphase chromosome segregation. The Ndc80 complex was first isolated in budding yeast and its homologues have been identified in worm, frog, chicken, and human (Ciferri, C. et al. J Biol Chem. 280, 29088-95 (2005).; McCleland, M. L et al. Genes Dev. 17, 101-114 (2003).; Desai, A. et al. Genes Dev. 17, 2421-2435 (2003).; DeLuca, J. G. et al. Curr Biol. 13, 2103-2109 (2003).). The attachment sites of the CDCA1-KNTC2 complex within the kinetochore outer plate generate microtubule dependent forces for chromosomal movement and regulate spindle checkpoint protein assembly at the kinetochore. Yeast cells that lost members of the complex or had mutated members were known to exhibit loss of kinetocore-microtubule attachment without global loss of kinetochore structure (Wigge, P. A. et al. J Cell Biol. 152, 349-60 (2001).). Yeast Nuf2 also disappears from the centromere during meiotic prophase, when centromeres lose their connection to the spindle pole body, and plays a regulatory role in the segregation of chromosomes (Nabetani, A. et al. Chromosoma. 110, 322-334 (2001).). Human CDCA1 was identified as a member of genes that were co-expressed with known cell cycle genes, including CDC2, cyclin, topoisomerase II and others21, and was reported to be associated with centromeres of mitotic HeLa cells; this confers the prospect that CDCA1 is a functional homolog of yeast Nuf2 (Wigge, P. A. et al. J Cell Biol. 152, 349-360 (2001).).

On the other hand, human KNTC2 was identified as an interacting protein with the C-terminus of the retinoblastoma protein (RB1) using a yeast 2-hybrid screening and was suggested to be one of several proteins involved in spindle checkpoint signaling (Durfee, T. et al. Genes Dev. 7, 555-569 (1993).; Chen, Y. et al. Mol. Cell. Biol. 17, 6049-6056 (1997).). This surveillance mechanism involving KNTC2 recruits the MPS1 kinase and MAD1/MAD2 complexes to kinetochores and assures correct segregation of chromosomes during cell division by detecting unaligned chromosomes and causing prometaphase arrest until the proper bipolar attachment of chromosomes is achieved (Martin-Lluesma, S. et al. Science 297, 2267-2270 (2002)).

Despite these advances, to date, there has been no report describing the significance of the co-activation of the CDCA1-KNTC2 complex in human cancer progression and its potential as therapeutic and prognostic targets.

BRIEF SUMMARY OF THE INVENTION

Through analysis of genome-wide gene-expression profiles among non-small cell lung carcinomas (NSCLCs), the present inventors detected the over-expression of a cell division associated 1 (CDCA1). The present inventors further found that the CDCA1 protein physically interacted with kinetocore associated 2 (KNTC2), a protein that was also specifically over-expressed in lung cancer. Northern-blot analysis revealed that these two genes were expressed only in testis among the 23 normal adult tissues examined. Immunohistochemical analysis of lung-cancer tissue microarrays demonstrated that co-activation of CDCA1 and KNTC2 in lung-cancer patients was associated with poor prognosis. In vitro, suppressing the expression of either CDCA1 or KNTC2 with siRNA, or inhibiting their binding using dominant-negative CDCA1 fragments or a synthesized 33 amino-acids polypeptide composed of the membrane transducing 11 poly-arginine sequence and the CDCA1-derived 19 amino-acids peptides (codons 398-416), effectively suppressed growth of NSCLC cells. As the data herein demonstrate that CDCA1 and KNTC2 fall in the category of cancer-testis antigens (CTAs) and that their simultaneous up-regulation is a frequent and important feature of lung-cancer cell growth/survival, selective suppression of CDCA1 or KNTC2 activity and/or inhibition of the formation of the CDCA1-KNTC2 complex purports to be a convenient therapeutic strategy for the treatment of many lung cancers.

Accordingly, the present invention provides methods of screening for a compound for treating or preventing NSCLC. An illustrative method includes the steps of:

(1) contacting a KNTC2 polypeptide or functional equivalent thereof with a CDCA1 polypeptide or functional equivalent thereof in the presence of a test compound;

(2) detecting the binding between the polypeptides of step (1); and (3) selecting the test compound that inhibits the binding between the polypeptides.

A functional equivalent of a CDCA1 polypeptide may have an amino acid sequence corresponding to the KNTC2 binding domain, for example the amino acid sequence of SEQ ID NO: 35 (IQKIKLGIQQLKDAAEREK). Likewise, a functional equivalent of a KNTC2 polypeptide may have an amino acid sequence that corresponds to the CDCA1 binding domain.

The present invention also provides methods for treating or preventing NSCLC in a subject by administering a compound that is obtained by the screening methods of the present invention described above.

The present invention further provides a kit for screening for a compound for treating or preventing NSCLC. The kit preferably includes the following components:

a: a KNTC2 polypeptide or functional equivalent thereof, and b: a CDCA1 polypeptide or functional equivalent thereof.

The present invention also provides methods of treating or preventing NSCLC in a subject including the step of administering to said subject an siRNA composition containing an siRNA that reduces the expression of a KNTC2 gene, wherein the siRNA has the nucleotide sequence of SEQ ID NO: 9, in the sense strand. The siRNA preferably has the following general formula:

5'-[A]-[B]-[A']-3', wherein [A] is a ribonucleotide sequence corresponding to SEQ ID NO: 9; [B] is a ribonucleotide sequence composed of 3 to 23 nucleotides; and [A'] is a ribonucleotide sequence complementary to [A].

The method of the present invention also provides for treating or preventing NSCLC in a subject by administering a CDCA1 mutant having dominant negative effect, or a polynucleotide encoding such a mutant. The CDCA1 mutant may have an amino acid sequence that includes a KNTC2 binding region, and excludes the nuf2 domain thereof. In a preferred embodiment, the CDCA1 mutant has the amino acid sequence of SEQ ID NO: 35. The CDCA1 mutant may have the following general formula:

[R]-[D], wherein [R] is a membrane transducing agent, and [D] is a polypeptide having the amino acid sequence of SEQ ID NO: 35. The membrane transducing agent can be selected from group consisting of;

poly-arginine;

SEQ ID NO: 37
Tat/RKKRRQRRR/;

SEQ ID NO: 38
Penetratin/RQIKIWFQNRRMKWKK/;

SEQ ID NO: 39
Buforin II/TRSSRAGLQFPVGRVHRLLRK/;

SEQ ID NO: 40
Transportan/GWTLNSAGYLLGKINLKALAALAKKIL;/

SEQ ID NO: 41
MAP (model amphipathic peptide)/KLALKLALKALKAALKLA/;

SEQ ID NO: 42
K-FGF/AAVALLPAVLLALLAP/;

SEQ ID NO: 43
Ku70/VPMLK/;

SEQ ID NO: 50
Ku70/PMLKE/;

SEQ ID NO: 44
Prion/MANLGYWLLALFVTMWTDVGLCKKRPKP/;

SEQ ID NO: 45
pVEC/LLIILRRRIRKQAHAHSK/;

SEQ ID NO: 46
Pep-1/KETWWETWWTEWSQPKKKRKV/;

SEQ ID NO: 47
SynB1/RGGRLSYSRRRFSTSTGR/;

SEQ ID NO: 48
Pep-7/SDLWEMMMVSLACQY/;
and

SEQ ID NO: 49
HN-1/TSPLNThNGQKL/.

The present invention provides a double-stranded molecule composed of a sense strand and an antisense strand, wherein the sense strand is a ribonucleotide sequence corresponding to a KNTC2 target sequence, and wherein the antisense strand is a ribonucleotide sequence which is complementary to said sense strand, wherein said sense strand and said antisense strand hybridize to each other to form said double-stranded molecule, and wherein said double-stranded molecule, when introduced into a cell expressing a KNTC2 gene, inhibits the expression of said gene. The double-stranded molecule may include a KNTC2 target sequence composed of at least about 10 contiguous nucleotides from the nucleotide sequence of SEQ ID NO: 31. In a preferred embodiment, the KNTC2 target sequence contains from about 19 to about 25 contiguous nucleotides from the nucleotide sequence of SEQ ID NO: 9, or may be composed entirely of SEQ ID NO: 9.

The double-stranded molecule may be a single ribonucleotide transcript composed of the sense strand and the antisense strand linked via a single-stranded ribonucleotide sequence. The double-stranded molecule is typically an oligonucleotide of less than about 100 nucleotides in length, less than about 75 nucleotides in length, less than about 50 nucleotides in length, or less than about 25 nucleotides in length. The double-stranded molecule can be an oligonucleotide of between about 19 and about 25 nucleotides in length.

The present invention also provides a vector encoding the double-stranded molecule of the invention described above. The vector may encode a transcript having a secondary structure that includes the sense strand and the antisense strand. The transcript may further include a single-stranded ribonucleotide sequence linking the sense strand and the antisense strand.

The present invention provides a vector containing a polynucleotide composed of a combination of a sense strand nucleic acid and an antisense strand nucleic acid, wherein the sense strand nucleic acid has the nucleotide sequence of SEQ ID NO: 9, and the antisense strand nucleic acid has a sequence complementary to the sense strand.

The polynucleotide may have the general formula of:

5'-[A]-[B]-[A']-3', wherein [A] is a nucleotide sequence of SEQ ID NO: 9; [B] is a nucleotide sequence consisting of 3 to 23 nucleotides; and [A'] is a nucleotide sequence complementary to [A].

The present invention provides compositions for treating or preventing NSCLC, such compositions including a pharmaceutically effective amount of an siRNA against KNTC2 gene. The siRNA may include a sense strand having the nucleotide sequence of SEQ ID NO: 9 as the target sequence.

The present invention further provides compositions for treating or preventing NSCLC, such compositions including a pharmaceutically effective amount of a compound selected by the screening methods of the present invention described above as an active ingredient, and a pharmaceutically acceptable carrier.

The present invention also provides compositions for treating or preventing NSCLC, such compositions including a pharmaceutically effective amount of a CDCA1 mutant of the present invention.

The present invention provides methods of assessing an NSCLC prognosis, wherein the method includes the steps of:

(a) detecting the expression level of either or both of CDCA1 and KNTC2 in a specimen collected from a subject whose NSCLC prognosis is to be assessed, and (b) indicating a poor prognosis when an elevation in the expression level of either or both of CDCA1 and KNTC2 is detected.

The above method may include the step of detecting the expression level of both of CDCA1 and KNTC2. The expression level may be detected by any one of the following methods:

(a) detecting the presence of an mRNA encoding the amino acid sequence of SEQ ID NO: 34 (CDCA1) or SEQ ID NO: 32 (KNTC2), (b) detecting the presence of a protein having the amino acid sequence of SEQ ID NO: 34 (CDCA1) or SEQ ID NO: 32 (KNTC2), and (c) detecting the biological activity of a protein having the amino acid sequence of SEQ ID NO: 34 (CDCA1) or SEQ ID NO: 32 (KNTC2).

The present invention also provides kits for assessing an NSCLC prognosis, wherein the kit includes any one component selected from the group consisting of:

(a) a reagent for detecting an mRNA encoding the amino acid sequence of SEQ ID NO: 34 (CDCA1) or SEQ ID NO: 32 (KNTC2), (b) a reagent for detecting a protein having the amino acid sequence of SEQ ID NO: 34 (CDCA1) or SEQ ID NO: 32 (KNTC2), and (c) a reagent for detecting the biological activity of a protein having the amino acid sequence of SEQ ID NO: 34 (CDCA1) or SEQ ID NO: 32 (KNTC2).

Definitions

The words "a", "an" and "the" as used herein mean "at least one" unless otherwise specifically indicated. The terms "protein" and "polypeptide" are used interchangeably. Furthermore, the terms "gene", "polynucleotide", and "nucleic acids" are used interchangeably unless otherwise specifically indicated.

The term "efficacious" refers to a treatment that results in a decrease in size, prevalence or metastatic potential of NSCLC in a subject. When a treatment is applied prophylactically, "efficacious" means that the treatment retards or prevents the occurrence of NSCLC or alleviates a clinical symptom of NSCLC. The assessment of NSCLC can be made using standard clinical protocols. Furthermore, the efficaciousness of a treatment may be determined in association with any known method for diagnosing or treating NSCLC. For example, NSCLC is frequently diagnosed histopathologically or by identifying symptomatic anomalies such as chronic cough, hoarseness, coughing up blood, weight loss, loss of appetite, shortness of breath, wheezing, repeated bouts of bronchitis or pneumonia and chest pain.

BRIEF DESCRIPTION OF THE DRAWINGS

FIG. 1A depicts the expression of CDCA1 and KNTC2 in clinical samples of 16 NSCLC (T) and corresponding normal lung tissues (N), examined by semiquantitative RT-PCR. The present inventors prepared appropriate dilutions of each single-stranded cDNA prepared from mRNAs of clinical lung-cancer samples, taking the level of β-actin (ACTB) expression as a quantitative control. FIG. 1B depicts the expression of CDCA1 and KNTC2 in NSCLC cell lines, (1:A549, 2:LC319, 3:PC14, 4:PC3, 5:PC9, 6:A427, 7:NCI-H1373, 8:EBC-1, 9:LU61, 10:NCI-H520, 11:NCI-H1703, 12:NCI-H2170, 13:NCI-H226, 14:RERF-LC-A1, 15:SK-MES-1, 16:NCI-H647, 17:LX1, 18:DMS114, 19:DMS273, 20:SBC-3, 21:SBC-5, 22:NCI-H1666, 23:NCI-H781) examined by semiquantitative RT-PCR. FIG. 1C depicts the expression of CDCA1 and KNTC2 in normal human tissues, detected by northern-blot analysis.

FIG. 2A identifies KNTC2 as a CDCA1-interacting protein. IP, immunoprecipitation; IB, immunoblot. FIG. 2B depicts the co-localization of endogenous CDCA1 (green) and endogenous KNTC2 (red) in LC319 cells. FIGS. 2C and 2D identify the region of CDCA1 that binds to KNTC2, through immunoprecipitation experiments. The CDCA11-148 and CDCA1149-306 constructs, which lacked C-terminal 158 amino-acids of CDCA1 did not retain any appreciable ability to interact with endogenous KNTC2 in LC319 cells (C). The CDCA1 277-367 and CDCA1 319-367 constructs, which lost 49 amino-acids of CDCA1 368-416, were unable to interact with endogenous KNTC2, suggesting that 49 amino-acid peptides of CDCA1 368-416, were supposed to be the most important region to interact with endogenous KNTC2 (D).

FIG. 3A depicts the results of immunohistochemical evaluation of representative samples from surgically-resected SCC tissues, using anti-CDCA1 (upper panels) and anti-KNTC2 (lower panels) polyclonal antibodies on tissue microarrays (×100). FIG. 3B-E depict the results of Kaplan-Meier analysis of tumor-specific survival times according to co-expression of CDCA1 and KNTC2 expression (B), CDCA1 expression (C), KNTC2 expression (D) on tissue microarrays. FIG. 3E, Association of co-over-expression of CDCA1 and KNTC2 with poor prognosis of NSCLC patients. The 282 NSCLC cases were divided into three groups; group-1 for cases with strong-positive staining for both CDCA1 and KNTC2 (62 patients), group-2 for cases with negative staining for both markers (29 patients), group-3 for any other cases (191 patients, shown as others).

FIGS. 4A and 4B, Left upper panels, indicate the gene knock-down effect in response to si-CDCA1, si-KNTC2 or control siRNAs in A549 cells, analyzed by semiquantitative RT-PCR. FIGS. 4 A and 4B, left lower and right panels, depict the results of colony-formation and MTT assays of LC319 cells transfected with specific siRNAs or control plasmids (EGFP, Scramble, or Luciferase). Error bars represent the standard deviation of triplicate assays.

FIG. 5A depicts the reduction of the complex formation detected by immunoprecipitation between exogenous CDCA1 and KNTC2 in LC319 cells that were co-transfected with the CDCA11-464 (full length) and CDCA1 200-464 construct (left top panel; black arrow). Interaction of the CDCA1 200-464 fragment with endogenous KNTC2 in LC319 cells (left top panel; white arrow). Input fractions (left third and bottom panels). Co-localization of CDCA1 200-464 and endogenous KNTC2 in the LC319 cells was detected by immunocytochemistry (right panels). FIG. 5B, MTT assay of LC319 cells, detecting a dominant-negative effect of CDCA1 200-464. CDCA1 149-306 was served as a control. Error bars represent the standard deviation of triplicate assays. FIG. 5C depicts the results of an MTT assay of LC319 cells, detecting a suppression of growth of LC319 cells by 11R-CDCA1 398-416 peptide transduction. Error bars represent the standard deviation of triplicate assays.

FIG. 6A depicts the results of the cell cycle analysis of LC319 cells after treatment with 11R-CDCA1398-416 peptides or Scramble peptides. FIG. 6B depicts the expressions of CDCA1 and KNTC2 proteins in normal human lung fibroblast-derived MRC5 cells as compared to 3 lung-cancer cell lines, examined by western-blot analysis (left panels). MTT assay shows no off-target effect of the 11R-CDCA1398-416 peptides on MRC5 cells that scarcely expressed CDCA1 and KNTC2 protein (right panel).

FIG. 7A depicts the growth suppressive effect of 11R-CDCA1398-416 peptides to A549 cells that were transplanted to nude mice. Average tumor volumes of 3 mice treated with 11R-CDCA1398-416 peptides (0.15 μmol/body/day), scramble peptides (0.15 μmol/body/day), or PBS (control) were plotted. Animals were daily administered with each of the peptides by intratumoral injection for 7 weeks. Growth of grafted tumor derived from A549 cells was significantly suppressed by dominant-negative cell-permeable 11R-CDCA1398-416 peptides. FIG. 7B depicts the gross appearance of tumors transplanted to the mice treated with 11R-CDCA1398-416 peptides (0.15 μmol/body/day), scramble peptides (0.15 μmol/body/day), or PBS (control) for 7 weeks.

DETAILED DESCRIPTION

Figure 1:
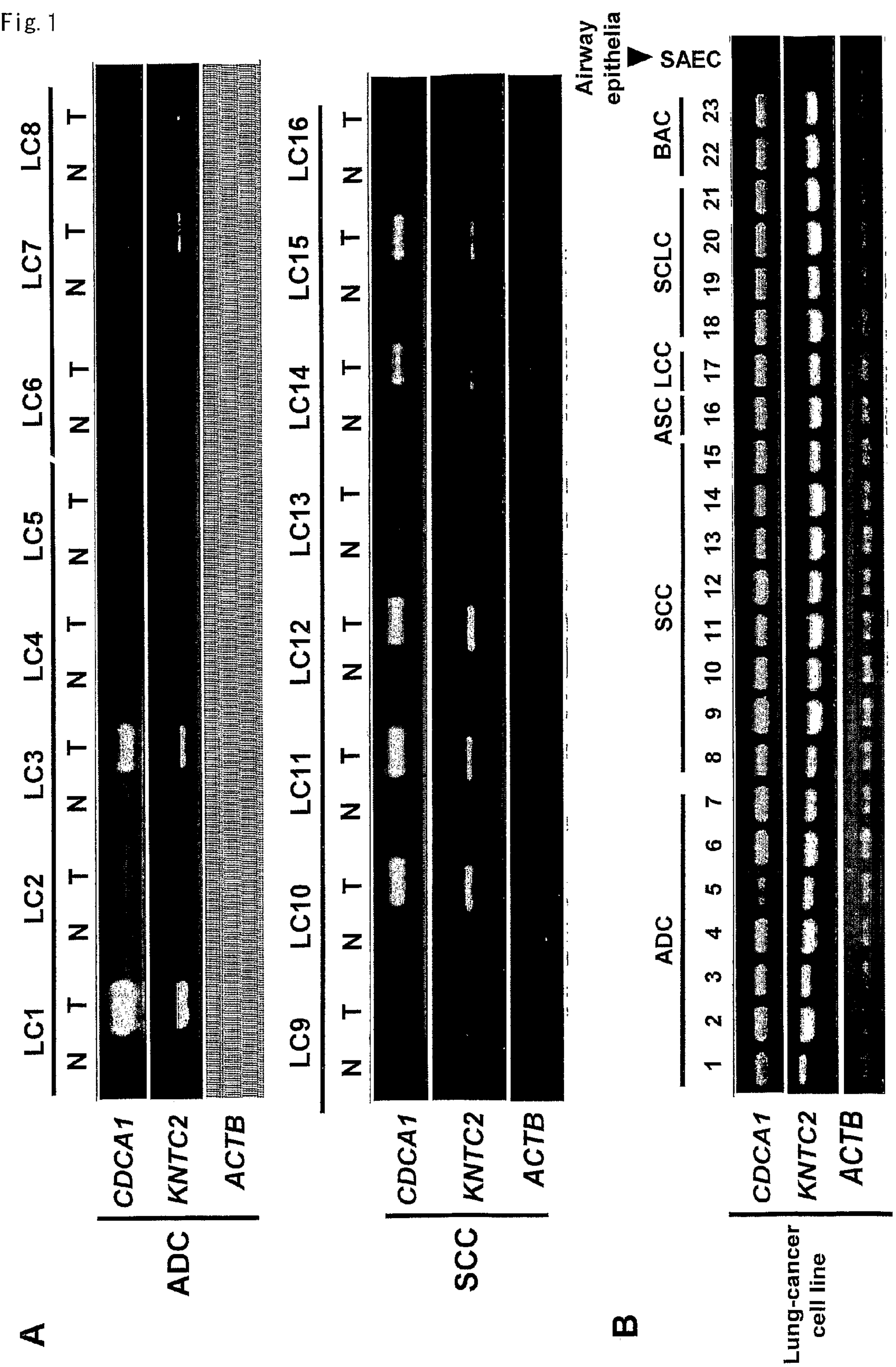
FIG. 1 depicts the expression of CDCA1 and KNTC2 in lung tumors, cell lines, and normal tissues.

Screening for a Compound for Treating or Preventing NSCLC

As described above, the present inventors revealed that CDCA1 interacts with KNTC2 in NSCLC cells. Thus, the present invention provides methods of screening for a compound for treating or preventing NSCLC. The methods include the steps of:

(1) contacting a KNTC2 polypeptide or functional equivalent thereof with a CDCA1 polypeptide or functional equivalent thereof in the presence of a test compound;

(2) detecting the binding between the polypeptides of step (1); and (3) selecting the test compound that inhibits the binding between the polypeptides.

In the context of the present invention, a functional equivalent of a CDCA1 or KNTC2 polypeptide is a polypeptide that has a biological activity equivalent to a CDCA1 polypeptide (SEQ ID NO: 34) or KNTC2 polypeptide (SEQ ID NO: 32), respectively.

Methods for preparing polypeptides functionally equivalent to a given protein are well known by a person skilled in the art and include known methods of introducing mutations into the protein. For example, one skilled in the art can prepare polypeptides functionally equivalent to CDCA1 or KNTC2 by introducing an appropriate mutation in the amino acid sequence of either of these proteins by site-directed mutagenesis (Hashimoto-Gotoh et al., Gene 152:271-5 (1995); Zoller and Smith, Methods Enzymol 100: 468-500 (1983); Kramer et al., Nucleic Acids Res. 12:9441-9456 (1984); Kramer and Fritz, Methods Enzymol 154: 350-67 (1987); Kunkel, Proc Natl Acad Sci USA 82: 488-92 (1985); Kunkel T A, et al., Methods Enzymol. 1991; 204:125-39.). Amino acid mutations can occur in nature, too. The polypeptides of the present invention includes those having the amino acid sequences of CDCA1 or KNTC2 in which one or more amino acids are mutated, provided the resulting mutated polypeptides are functionally equivalent to CDCA1 or KNTC2, respectively. The number of amino acids to be mutated in such a mutant is generally 20 amino acids or less, more typically 10 amino acids or less, preferably 5-6 amino acids or less, and more preferably 1-3 amino acids.

Mutated or modified proteins, proteins having amino acid sequences modified by substituting, deleting, inserting, and/or adding one or more amino acid residues of a certain amino acid sequence, have been known to retain the original biological activity (Mark et al., Proc Natl Acad Sci USA 81: 5662-6 (1984); Zoller and Smith, Nucleic Acids Res 10:6487-500 (1982); Dalbadie-McFarland et al., Proc Natl Acad Sci USA 79: 6409-13 (1982)).

The amino acid residue to be mutated is preferably mutated into a different amino acid in which the properties of the amino acid side-chain are conserved (a process known as conservative amino acid substitution). Examples of properties of amino acid side chains are hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). Note, the parenthetic letters indicate the one-letter codes of amino acids.

An example of a polypeptide to which one or more amino acids residues are added to the amino acid sequence of CDCA1 or KNTC2 is a fusion protein containing CDCA1 or KNTC2, respectively. Accordingly, fusion proteins, i.e., fusions of CDCA1 or KNTC2 and other peptides or proteins, are included in the present invention. Fusion proteins can be made by techniques well known to a person skilled in the art, such as by linking the DNA encoding CDCA1 or KNTC2 with DNA encoding other peptides or proteins, so that the frames match, inserting the fusion DNA into an expression vector and expressing it in a host. There is no restriction as to the peptides or proteins fused to the protein of the present invention.

An alternative method known in the art to isolate functionally equivalent polypeptides is, for example, the method using a hybridization technique (Sambrook et al., Molecular Cloning 2nd ed. 9.47-9.58, Cold Spring Harbor Lab. Press (1989)). One skilled in the art can readily isolate a DNA having high homology with CDCA1 or KNTC2 (i.e., SEQ ID NOs: 34 and 32, respectively), and isolate functionally equivalent polypeptides to the CDCA1 or KNTC2 from the isolated DNA. The proteins of the present invention include those that are encoded by DNA that hybridize with a whole or part of the DNA sequence encoding CDCA1 or KNTC2 and are functionally equivalent to CDCA1 or KNTC2. These polypeptides include mammal homologues corresponding to the protein derived from human (for example, a polypeptide encoded by a monkey, rat, rabbit and bovine gene). In isolating a cDNA highly homologous to the DNA encoding CDCA1 or KNTC2 from animals, it is particularly preferable to use lung cancer tissues.

Preferably, the functional equivalent polypeptide has an amino acid sequence with at least about 80% homology (also referred to as sequence identity) to the native CDCA1 or KNTC2 sequence disclosed here, more preferably at least about 85%, 90%, 95%, 96%, 97%, 98%, or 99% homology. The homology of a polypeptide can be determined by following the algorithm in "Wilbur and Lipman, Proc Natl Acad Sci USA 80: 726-30 (1983)". In other embodiments, the functional equivalent polypeptide can be encoded by a polynucleotide that hybridizes under stringent conditions (as defined below) to a polynucleotide encoding such a functional equivalent polypeptide.

In place of hybridization, a gene amplification method, for example, the polymerase chain reaction (PCR) method, can be utilized to isolate a DNA encoding a polypeptide functionally equivalent to CDCA1 or KNTC2, using a primer synthesized based on the sequence information for CDCA1 or KNTC2.

A CDCA1 or KNTC2 functional equivalent useful in the context of the present invention may have variations in amino acid sequence, molecular weight, isoelectric point, the presence or absence of sugar chains, or form, depending on the cell or host used to produce it or the purification method utilized. Nevertheless, so long as it is a function equivalent of either the CDCA1 or KNTC2 polypeptide, it is within the scope of the present invention.

In some preferred embodiments, the functional equivalent of the CDCA1 polypeptide can include an amino acid sequence corresponding to the KNTC2 binding domain, for example the amino acid sequence of SEQ ID NO: 35 (IQKIKLGIQQ LKDAAEREK). Similarly, the functional equivalent of KNTC2 polypeptide can include an amino acid sequence corresponding to the CDCA1 binding domain.

As discussed above, the inhibition of binding between CDCA1 and KNTC2 leads to the suppression of cell proliferation. Accordingly, compounds that inhibit this binding may serve as pharmaceuticals for treating or preventing NSCLCs. The CDCA1 and KNTC2 polypeptides to be used for the screening methods of the present invention may be a recombinant polypeptide or a protein derived from the nature, or may also be a partial peptide thereof, so long as it retains the binding ability of the full-length protein. Such partial peptides retaining the binding ability are herein referred to as "functional equivalents". The CDCA1 and KNTC2 polypeptides to be used in the screening methods can be, for example, a purified polypeptide, a soluble protein, a form bound to a carrier or a fusion protein fused with other polypeptides.

As a method of screening for compounds that inhibit the binding between CDCA1 and KNTC2, many methods well known by one skilled in the art can be used. For example, screening can be carried out as an in vitro assay system, such as a cellular system. More specifically, first, either CDCA1 or KNTC2 is bound to a support, and the other protein is added together with a test compound thereto. Next, the mixture is incubated, washed and the other protein bound to the support is detected and/or measured.

Examples of supports that may be used for binding proteins include, for example, insoluble polysaccharides, such as agarose, cellulose and dextran; and synthetic resins, such as polyacrylamide, polystyrene and silicon; preferably commercial available beads and plates (e.g., multi-well plates, biosensor chip, etc.) prepared from the above materials may be used. When using beads, they may be filled into a column. Alternatively, the use of magnetic beads is also known in the art, and enables one to readily isolate proteins bound on the beads via magnetism.

The binding of a protein to a support may be conducted according to routine methods, such as chemical bonding and physical adsorption, for example. Alternatively, a protein may be bound to a support via antibodies that specifically recognize the protein. Moreover, binding of a protein to a support can be also conducted by means of avidin and biotin.

The binding between proteins is preferably carried out in buffer, examples of which include, but are not limited to, phosphate buffer and Tris buffer. However, the selected buffer must not inhibit binding between the proteins.

In the context of the present invention, a biosensor using the surface plasmon resonance phenomenon may be used as a mean for detecting or quantifying the bound protein. When such a biosensor is used, the interaction between the proteins can be observed in real-time as a surface plasmon resonance signal, using only a minute amount of polypeptide and without labeling (for example, BIAcore, Pharmacia). Therefore, it is possible to evaluate binding between the CDCA1 and KNTC2 using a biosensor such as BIAcore.

Alternatively, either CDCA1 or KNTC2 may be labeled, and the label of the bound protein may be used to detect or measure the bound protein. Specifically, after pre-labeling one of the proteins, the labeled protein is contacted with the other protein in the presence of a test compound, and then bound proteins are detected or measured according to the label after washing.

Labeling substances including but not limited to radioisotope (e.g., $^{3}H$, $^{14}C$, $^{32}P$, $^{33}P$, $^{35}S$, $^{125}I$, $^{131}I$), enzymes (e.g., alkaline phosphatase, horseradish peroxidase, β-galactosidase, β-glucosidase), fluorescent substances (e.g., fluorescein isothiosyanete (FITC), rhodamine) and biotin/avidin may be used for the labeling of a protein in the present method. When the protein is labeled with a radioisotope, the detection or measurement can be carried out by liquid scintillation. Alternatively, proteins labeled with enzymes can be detected or measured by adding a substrate of the enzyme to detect the enzymatic change of the substrate, such as generation of color, with absorptiometer. Further, in case where a fluorescent substance is used as the label, the bound protein may be detected or measured using fluorophotometer.

Furthermore, binding of CDCA1 and KNTC2 can be also detected or measured using antibodies to CDCA1 or KNTC2. For example, after contacting the CDCA1 polypeptide immobilized on a support with a test compound and KNTC2, the mixture is incubated and washed, and detection or measurement can be conducted using an antibody against KNTC2. Alternatively, KNTC2 may be immobilized on a support, and an antibody against CDCA1 may be used as the antibody.

When using an antibody in the present screening, the antibody is preferably labeled with one of the labeling substances mentioned above, and detected or measured based on the labeling substance. Alternatively, an antibody against CDCA1 or KNTC2 may be used as a primary antibody to be detected with a secondary antibody that is labeled with a labeling substance. Furthermore, an antibody bound to the protein in the screening of the present invention may be detected or measured using protein G or protein A column.

Alternatively, in another embodiment of the screening method of the present invention, a two-hybrid system utilizing cells may be used ("MATCHMAKER Two-Hybrid system", "Mammalian MATCHMAKER Two-Hybrid Assay Kit", "MATCHMAKER one-Hybrid system" (Clontech); "HybriZAP Two-Hybrid Vector System" (Stratagene); the references "Dalton and Treisman, Cell 68: 597-612 (1992)", "Fields and Sternglanz, Trends Genet 10: 286-92 (1994)").

In the two-hybrid system, for example, a CDCA1 polypeptide is fused to an SRF-binding region or GAL4-binding region and expressed in yeast cells. A KNTC2 polypeptide that binds to the CDCA1 polypeptide is fused to a VP16 or GAL4 transcriptional activation region and also expressed in the yeast cells in the existence of a test compound. Alternatively, a KNTC2 polypeptide may be fused to an SRF-binding region or GAL4-binding region, and a CDCA1 polypeptide fused to a VP16 or GAL4 transcriptional activation region. When the test compound does not inhibit the binding between CDCA1 and KNTC2, the binding of the two activates a reporter gene, making positive clones detectable. As a reporter gene, in addition to the HIS3 gene, suitable examples include, but are not limited to, Ade2 gene, lacZ gene, CAT gene, luciferase gene and the like.

Any test compound, for example, cell extracts, cell culture supernatant, products of fermenting microorganism, extracts from marine organism, plant extracts, purified or crude proteins, peptides, non-peptide compounds, synthetic micromolecular compounds and natural compounds can be used in the context of the screening methods of the present invention. The test compound of the present invention can be also obtained using any of the numerous approaches in combinatorial library methods known in the art, including, but not limited to, (1) biological libraries, (2) spatially addressable parallel solid phase or solution phase libraries, (3) synthetic library methods requiring deconvolution, (4) the "one-bead one-compound" library method and (5) synthetic library methods using affinity chromatography selection. The biological library methods using affinity chromatography selection is limited to peptide libraries, while the other four approaches are applicable to peptide, non-peptide oligomer or small molecule libraries of compounds (Lam, Anticancer Drug Des. 12: 145-67 (1997)). Examples of methods for the synthesis of molecular libraries can be found in the art (DeWitt et al., *Proc. Natl. Acad. Sci. USA* 90: 6909 (1993); Erb et al., *Proc. Natl. Acad. Sci. USA* 91: 11422-6 (1994); Zuckermann et al., *J. Med. Chem.* 37: 2678-85 (1994); Cho et al., *Science* 261: 1303-5 (1993); Carell et al., *Angew. Chem. Int. Ed. Engl.* 33: 2059 (1994); Carell et al., *Angew. Chem. Int. Ed. Engl.* 33: 2061 (1994); Gallop et al., *J. Med. Chem.* 37:1233-51 (1994)). Libraries of compounds may be presented in solution (see Houghten, *Bio/Techniques* 13: 412-21 (1992)) or on beads (Lam, *Nature* 354: 82-4 (1991)), chips (Fodor, *Nature* 364: 555-6 (1993)), bacteria (U.S. Pat. No. 5,223,409), spores (U.S. Pat. Nos. 5,571,698; 5,403,484, and 5,223,409), plasmids (Cull et al., *Proc. Natl. Acad. Sci. USA* 89: 1865-9 (1992)) or phage (Scott and Smith, *Science* 249: 386-90 (1990); Devlin, *Science* 249: 404-6 (1990); Cwirla et al., *Proc. Natl. Acad. Sci. USA* 87: 6378-82 (1990); Felici, *J. Mol. Biol.* 222: 301-10 (1991); US Pat. Application 20020103360). The test compound exposed to a cell or protein according to the screening methods of the present invention may be a single compound or a combination of compounds. When a combination of compounds is used in the screening methods of the invention, the compounds may be contacted sequentially or simultaneously.

A compound isolated by the screening methods of the present invention is a candidate for drugs which inhibit the activity of CDCA1 and KNTC2, for treating or preventing diseases attributed to, for example, cell proliferative diseases, such as NSCLC. A compound in which a part of the structure of the compound obtained by the present screening methods of the present invention is converted by addition, deletion and/or replacement, is included in the compounds obtained by the screening methods of the present invention. A compound effective in suppressing the expression of over-expressed genes, i.e., the CDCA1 and KNTC2 genes, is deemed to have a clinical benefit and can be further tested for its ability to reduce or prevent cancer cell growth in animal models or test subjects.

The present invention may also include screening for proteins that bind to a CDCA1 or KNTC2 polypeptide to inhibit the interaction thereof. To that end, many methods well known to those skilled in the art can be used. Such a screening can be conducted by, for example, an immunoprecipitation assay using methods well known in the art. The proteins of the invention can be recombinantly produced using standard procedures. For example, a gene encoding a polypeptide of interest may be expressed in animal cells by inserting the gene into an expression vector for foreign genes, such as pSV2neo, pcDNA I, pcDNA3.1, pCAGGS and pCD8. The promoter to be used for the expression may be any promoter that can be used commonly and include, for example, the SV40 early promoter (Rigby in Williamson (ed.), *Genetic Engineering*, vol. 3. Academic Press, London, 83-141 (1982)), the EF-α promoter (Kim et al., *Gene* 91: 217-23 (1990)), the CAG promoter (Niwa et al., *Gene* 108: 193 (1991)), the RSV LTR promoter (Cullen, *Methods in Enzymology* 152: 684-704 (1987)) the SR α promoter (Takebe et al., *Mol Cell Biol* 8: 466-72 (1988)), the CMV immediate early promoter (Seed and Aruffo, *Proc Natl Acad Sci USA* 84: 3365-9 (1987)), the SV40 late promoter (Gheysen and Fiers, *J Mol Appl Genet* 1: 385-94 (1982)), the Adenovirus late promoter (Kaufman et al., *Mol Cell Biol* 9: 946-58 (1989)), the HSV TK promoter and so on. The introduction of the gene into animal cells to express a foreign gene can be performed according to any conventional method, for example, the electroporation method (Chu et al., *Nucleic Acids Res* 15: 1311-26 (1987)), the calcium phosphate method (Chen and Okayama, *Mol Cell Biol* 7: 2745-52 (1987)), the DEAE dextran method (Lopata et al., *Nucleic Acids Res* 12: 5707-17 (1984); Sussman and Milman, *Mol Cell Biol* 4: 1641-3 (1984)), the Lipofectin method (Derijard B, *Cell* 76: 1025-37 (1994); Lamb et al., *Nature Genetics* 5: 22-30 (1993): Rabindran et al., *Science* 259: 230-4 (1993)), and so on. The polypeptide can also be expressed as a fusion protein including a recognition site (epitope) of a monoclonal antibody by introducing the epitope of the monoclonal antibody, whose specificity has been revealed, to the N- or C-terminus of the polypeptide. A commercially available epitope-antibody system can also be used (*Experimental Medicine* 13: 85-90 (1995)). Vectors which can express a fusion protein with, for example, β-galactosidase, maltose binding protein, glutathione S-transferase, green florescence protein (GFP), and so on, by the use of its multiple cloning sites are commercially available.

A fusion protein, prepared by introducing only small epitopes composed of several to a dozen amino acids so as not to change the property of the original polypeptide by the fusion, is also provided herein. Epitopes, such as polyhistidine (His-tag), influenza aggregate HA, human c-myc, FLAG, Vesicular stomatitis virus glycoprotein (VSV-GP), T7 gene 10 protein (T7-tag), human simple herpes virus glycoprotein (HSV-tag), E-tag (an epitope on monoclonal phage) and such, and monoclonal antibodies recognizing them can be used as the epitope-antibody system for screening proteins binding to the CDCA1 or KNTC2 polypeptide (*Experimental Medicine* 13: 85-90 (1995)).

In immunoprecipitation, an immune complex is formed by adding these antibodies to cell lysate prepared using an appropriate detergent. The immune complex is composed of the CDCA1 or KNTC2 polypeptide, a polypeptide having binding affinity for the polypeptide, and an antibody. Immunoprecipitation can be also conducted using antibodies against the CDCA1 or KNTC2 polypeptide, in addition to antibodies against the above epitopes, which antibodies can be prepared according to conventional methods and may be in any form, such as monoclonal or polyclonal antibodies, and include, for example, antiserum obtained by immunizing an animal such as a rabbit with the polypeptide, all classes of polyclonal and monoclonal antibodies, as well as recombinant antibodies (e.g., humanized antibodies).

Specifically, antibodies against the CDCA1 or KNTC2 polypeptide can be prepared using techniques well known in the art. For example, the CDCA1 or KNTC2 polypeptides used as an antigen to obtain an antibody may be derived from any animal species, but preferably is derived from a mammal such as a human, mouse, rabbit, or rat, more preferably from a human. The polypeptide used as the antigen can be recombinantly produced or isolated from natural sources. In the context of the present invention, the polypeptide to be used as an immunization antigen may be a complete protein or a partial peptide of the CDCA1 or KNTC2 polypeptide.

Any mammalian animal may be immunized with the antigen; however, the compatibility with parental cells used for cell fusion is preferably taken into account. In general, animals of the order Rodentia, Lagomorpha or Primate are used. Animals of the Rodentia order include, for example, mice, rats and hamsters. Animals of Lagomorpha order include, for example, hares, pikas, and rabbits. Animals of Primate order include, for example, monkeys of Catarrhini (old world monkey) such as *Macaca fascicularis*, rhesus monkeys, sacred baboons and chimpanzees.

Methods for immunizing animals with antigens are well known in the art. Intraperitoneal injection or subcutaneous injection of antigens is a standard method for immunizing mammals. More specifically, antigens may be diluted and suspended in an appropriate amount of phosphate buffered saline (PBS), physiological saline, etc. If desired, the antigen suspension may be mixed with an appropriate amount of a standard adjuvant, such as Freund's complete adjuvant, made into emulsion, and then administered to mammalian animals. Preferably, it is followed by several administrations of the antigen mixed with an appropriately amount of Freund's incomplete adjuvant every 4 to 21 days. An appropriate carrier may also be used for immunization. After immunization as above, the serum is examined by a standard method for an increase in the amount of desired antibodies.

Polyclonal antibodies against a CDCA1 or KNTC2 polypeptide may be prepared by collecting blood from the immunized mammal examined for the increase of desired antibodies in the serum, and by separating serum from the blood by any conventional method. Polyclonal antibodies include serum containing the polyclonal antibodies, as well as the fraction containing the polyclonal antibodies isolated from the serum. Immunoglobulin G or M can be prepared from a fraction which recognizes only the CDCA1 or KNTC2 polypeptide using, for example, an affinity column coupled with the polypeptide, and further purifying this fraction using protein A or protein G column.

To prepare monoclonal antibodies, immune cells are collected from the mammal immunized with the antigen and checked for the increased level of desired antibodies in the serum as described above, and are subjected to cell fusion. The immune cells used for cell fusion are preferably obtained from spleen. Other preferred parental cells to be fused with the above immunocyte include, for example, myeloma cells of mammalians, and more preferably myeloma cells having an acquired property for the selection of fused cells by drugs.

The above immunocyte and myeloma cells can be fused according to known methods, for example, the method of Milstein et al., (Galfre and Milstein, Methods Enzymol 73: 3-46 (1981)).

Resulting hybridomas obtained by the cell fusion may be selected by cultivating them in a standard selection medium, such as HAT medium (hypoxanthine, aminopterin, and thymidine containing medium). The cell culture is typically continued in the HAT medium for several days to several weeks, the time being sufficient to allow all the other cells, with the exception of the desired hybridoma (non-fused cells), to die. Then, the standard limiting dilution is performed to screen and clone a hybridoma cell producing the desired antibody.

In addition to the above method, in which a non-human animal is immunized with an antigen for preparing hybridoma, human lymphocytes, such as those infected by the EB virus, may be immunized with a CDCA1 or KNTC2 polypeptide, cells expressing such a polypeptide, or their lysates in vitro. Then, the immunized lymphocytes are fused with human-derived myeloma cells that are capable of indefinitely dividing, such as U266, to yield a hybridoma producing a desired human antibody that is able to bind to the CDCA1 or KNTC2 polypeptide (Unexamined Published Japanese Patent Application No. (JP-A) Sho 63-17688).

The obtained hybridomas may be subsequently transplanted into the abdominal cavity of a mouse and the ascites may be extracted. The obtained monoclonal antibodies can be purified by, for example, ammonium sulfate precipitation, a protein A or protein G column, DEAE ion exchange chromatography, or an affinity column to which any of the target proteins of the present invention (CDCA1 or KNTC2 polypeptide) is coupled. The antibody can be used not only in the present screening method, but also for the purification and detection of a CDCA1 or KNTC2 polypeptide. They may further serve as candidates for agonists and antagonists of the polypeptides of interest. In addition, such antibodies, serving as candidates for antagonists, can be applied to the antibody treatment for diseases related to the CDCA1 or KNTC2 polypeptide, including NSCLC as described infra.

Monoclonal antibodies thus obtained can be also recombinantly prepared using genetic engineering techniques (see, for example, Borrebaeck and Larrick, Therapeutic Monoclonal Antibodies, published in the United Kingdom by MacMillan Publishers LTD (1990)). For example, a DNA encoding an antibody may be cloned from an immune cell, such as a hybridoma or an immunized lymphocyte producing the antibody, inserted into an appropriate vector, and introduced into host cells to prepare a recombinant antibody. Such recombinant antibody can also be used in the context of the present screening.

Furthermore, an antibody used in the screening and so on may be a fragment of an antibody or a modified antibody, so long as it binds to one or both of CDCA1 and KNTC2. For instance, the antibody fragment may be an Fab, $F(ab')_2$, Fv, or single chain Fv (scFv), in which Fv fragments from H and L chains are ligated by an appropriate linker (Huston et al., *Proc Natl Acad Sci USA* 85: 5879-83 (1988)). More specifically, an antibody fragment may be generated by treating an antibody with an enzyme, such as papain or pepsin. Alternatively, a gene encoding an antibody fragment may be constructed, inserted into an expression vector, and expressed in an appropriate host cell (see, for example, Co et al., *J Immunol* 152: 2968-76 (1994); Better and Horwitz, *Methods Enzymol* 178: 476-96 (1989); Pluckthun and Skerra, *Methods Enzymol* 178: 497-515 (1989); Lamoyi, *Methods Enzymol* 121: 652-63 (1986); Rousseaux et al., *Methods Enzymol* 121: 663-9 (1986); Bird and Walker, *Trends Biotechnol* 9:132-7 (1991)).

An antibody may be modified by conjugation with a variety of molecules, such as polyethylene glycol (PEG). Modified antibodies can be obtained through chemically modification of an antibody. These modification methods are conventional in the field.

Alternatively, an antibody may be obtained as a chimeric antibody, between a variable region derived from a nonhuman antibody and a constant region derived from a human antibody, or as a humanized antibody, composed of a complementarity determining region (CDR) derived from a nonhuman antibody, a frame work region (FR) derived from a human antibody, and a constant region. Such antibodies can be prepared using known technology.

Humanization can be performed by substituting rodent CDRs or CDR sequences for the corresponding sequences of a human antibody (see, e.g., Verhoeyen et al., *Science* 239: 1534-6 (1988)). Accordingly, such humanized antibodies are chimeric antibodies, wherein substantially less than an intact human variable domain has been substituted by the corresponding sequence from a non-human species. Fully human antibodies composed of human variable regions in addition to human framework and constant regions can also be used. Such antibodies can be produced using various techniques known in the art. For example, in vitro methods involve use of recombinant libraries of human antibody fragments displayed on bacteriophage (e.g., Hoogenboom & Winter, *J. Mol. Biol.* 227:381-8 (1992), Similarly, human antibodies can be made by introducing of human immunoglobulin loci into transgenic animals, e.g., mice in which the endogenous immunoglobulin genes have been partially or completely inactivated. This approach is described, e.g., in U.S. Pat. Nos. 6,150,584, 5,545,807; 5,545,806; 5,569,825; 5,625,126; 5,633,425; 5,661,016.

Antibodies obtained as above may be purified to homogeneity. For example, the separation and purification of the antibody can be performed according to separation and purification methods used for general proteins. For example, the antibody may be separated and isolated by appropriately selected and combined column chromatographies, such as affinity chromatography, filter, ultrafiltration, salting-out, dialysis, SDS polyacrylamide gel electrophoresis, isoelectric focusing, and others (Antibodies: A Laboratory Manual. Ed Harlow and David Lane, Cold Spring Harbor Laboratory (1988)); however, the present invention is not limited thereto. A protein A column and protein G column can be used as the affinity column. Exemplary protein A columns to be used include, for example, Hyper D, POROS, and Sepharose F.F. (Pharmacia).

Exemplary chromatography, with the exception of affinity, includes, for example, ion-exchange chromatography, hydrophobic chromatography, gel filtration, reverse-phase chromatography, adsorption chromatography, and the like (Strategies for Protein Purification and Characterization: A Laboratory Course Manual. Ed Daniel R. Marshak et al., Cold Spring Harbor Laboratory Press (1996)). The chromatographic procedures can be carried out by liquid-phase chromatography, such as HPLC and FPLC.

An immune complex can be precipitated, for example with Protein A sepharose or Protein G sepharose when the antibody is a mouse IgG antibody. If the CDCA1 or KNTC2 polypeptide is prepared as a fusion protein with an epitope, such as GST, an immune complex can be formed in the same manner as in the use of the antibody against the CDCA1 or KNTC2 polypeptide, using a substance specifically binding to these epitopes, such as glutathione-Sepharose 4B.

Immunoprecipitation can be performed by following or according to, for example, the methods in the literature (Harlow and Lane, Antibodies, 511-52, Cold Spring Harbor Laboratory publications, New York (1988)).

SDS-PAGE is commonly used for analysis of immunoprecipitated proteins and the bound protein can be analyzed by the molecular weight of the protein using gels with an appropriate concentration. Since the protein bound to the CDCA1 or KNTC2 polypeptide is difficult to detect with conventional staining methods, such as Coomassie staining or silver staining, the detection sensitivity for the protein can be improved by culturing cells in culture medium containing radioactive isotope, $^{35}$S-methionine or $^{35}$S-cystein, labeling proteins in the cells, and detecting the proteins. The target protein can be purified directly from the SDS-polyacrylamide gel and its sequence can be determined, when the molecular weight of the protein has been revealed.

A compound binding to the CDCA1 or KNTC2 polypeptide can also be screened using affinity chromatography. For example, a CDCA1 or KNTC2 polypeptide may be immobilized on a carrier of an affinity column, and a test compound is applied to the column. A test compound herein may be, for example, cell extracts, cell lysates, etc. After loading the test compound, the column is washed, and compounds bound to the CDCA1 or KNTC2 polypeptide can be prepared.

When the test compound is a protein, the amino acid sequence of the obtained protein is analyzed, an oligo DNA is synthesized based on the sequence, and cDNA libraries are screened using the oligo DNA as a probe to obtain a DNA encoding the protein.

A biosensor using the surface plasmon resonance phenomenon may be used as a mean for detecting or quantifying the bound compound in the present invention. When such a biosensor is used, the interaction between the CDCA1 or KNTC2 polypeptide and a test compound can be observed in real-time as a surface plasmon resonance signal, using only a minute amount of polypeptide and without labeling (for example, BIAcore, Pharmacia). Therefore, it is possible to evaluate the binding between a CDCA1 or KNTC2 polypeptide and a test compound using a biosensor such as BIAcore.

The methods of screening for molecules that bind when an immobilized CDCA1 or KNTC2 polypeptide is exposed to synthetic chemical compounds, or natural substance banks or a random phage peptide display library, and the methods of screening using high-throughput based on combinatorial chemistry techniques (Wrighton et al., *Science* 273: 458-64 (1996); Verdine, *Nature* 384: 11-3 (1996)) to isolate not only proteins but chemical compounds that bind to a CDCA1 or KNTC2 protein (including agonist and antagonist) are well known to one skilled in the art.

Differences in the genetic makeup of individuals can result in differences in their relative abilities to metabolize various drugs. A compound that is metabolized in a subject to act as an anti-NSCLC agent can manifest itself by inducing a change in a gene expression pattern in the subject's cells from that characteristic of a cancerous state to a gene expression pattern characteristic of a non-cancerous state. Accordingly, the differentially expressed CDCA1 or KNTC2 genes disclosed herein allow for the selection of a putative therapeutic or prophylactic inhibitor of NSCLC specifically adequate for a subject by testing candidate compounds in a test cell (or test cell population) derived from the selected subject.

To identify an anti-NSCLC agent that is appropriate for a specific subject, a test cell or test cell population derived from the subject is exposed to a therapeutic agent and the expression of one or more of the CDCA1 or KNTC2 genes is determined.

The test cell is or the test cell population contains an NSCLC cell expressing a CDCA1 or KNTC2 gene. Preferably, the test cell or the test cell population includes a lung cell. For example, the test cell or test cell population may be incubated in the presence of a candidate agent and the pattern of gene expression of the test cell or cell population may be measured and compared to one or more reference profiles, e.g., an NSCLC reference expression profile or a non-NSCLC reference expression profile.

A decrease in the expression of CDCA1 or KNTC2 in a test cell or test cell population relative to a reference cell population containing NSCLC is indicative that the agent is therapeutically efficacious.

Methods for Treating or Preventing NSCLC

The present invention further provides a method for treating, alleviating or preventing NSCLC in a subject. Therapeutic compounds may be administered prophylactically or therapeutically to subjects suffering from or at risk of (or susceptible to) developing NSCLC. Such subjects are identified using standard clinical methods or by detecting an aberrant level of expression or activity of CDCA1 or KNTC2 gene or polypeptide. Prophylactic administration occurs prior to the manifestation of overt clinical symptoms of disease, such that a disease or disorder is prevented or alternatively delayed in its progression.

The inventive method includes decreasing the expression or function, or both, of one or more gene products of genes whose expression is aberrantly increased in an NSCLC cell relative to normal cells of the same tissue type from which the NSCLC cells are derived. The expression may be inhibited by any method known in the art. For example, a subject may be treated with an effective amount of a compound that decreases the amount of a CDCA1 or KNTC2 gene in the subject. Administration of the compound can be systemic or local. Such therapeutic compounds include compounds that decrease the expression level of such gene that endogenously exists in the NSCLC cells (i.e., compounds that down-regulate the expression of CDCA1 or KNTC2 genes). The administration of such therapeutic compounds counter the effects of aberrantly-over expressed gene(s) in the subjects NSCLC cells and are expected to improve the clinical condition of the subject. Such compounds can be obtained by the screening method of the present invention described above.

Alternatively, the expression of CDCA1 or KNTC2 can be inhibited by administering to the subject a nucleic acid that inhibits or antagonizes the expression of the over-expressed gene(s). Antisense oligonucleotides, siRNAs or ribozymes which disrupt the expression of the over-expressed gene(s) can be used for inhibiting the expression of the over-expressed gene(s).

As noted above, antisense-oligonucleotides corresponding to any of the nucleotide sequence of a CDCA1 or KNTC2 gene can be used to reduce the expression level of the gene. Antisense-oligonucleotides corresponding to the CDCA1 or KNTC2 genes that are up-regulated in NSCLC are useful in the treatment or prevention of NSCLC. Specifically, antisense-oligonucleotides against the genes may act by binding to any of the corresponding polypeptides encoded by these genes, or mRNAs corresponding thereto, thereby inhibiting the transcription or translation of the genes, promoting the degradation of the mRNAs, and/or inhibiting the expression of proteins encoded by the CDCA1 or KNTC2 nucleotides, and finally inhibiting the function of the proteins. The term "antisense-oligonucleotides" as used herein encompasses both nucleotides that are entirely complementary to the target sequence and those having a mismatch of one or more nucleotides, so long as the antisense-oligonucleotides can specifically hybridize to the target sequence. For example, the antisense-oligonucleotides of the present invention include polynucleotides having a homology (also referred to as sequence identity) of at least 70% or higher, preferably at 80% or higher, more preferably 90% or higher, even more preferably 95% or higher over a span of at least 15 continuous nucleotides up to the full length sequence of any of the nucleotide sequences of a CDCA1 or KNTC2 gene. Algorithms known in the art can be used to determine the homology. Furthermore, derivatives or modified products of the antisense-oligonucleotides can also be used as antisense-oligonucleotides in the present invention. Examples of such modified products include lower alkyl phosphonate modifications, such as methyl-phosphonate-type or ethyl-phosphonate-type, phosphorothioate modifications and phosphoroamidate modifications siRNA molecules of the invention can also be defined by their ability to hybridize specifically to mRNA or cDNA from the genes disclosed here. In the context of the present invention, the terms "hybridize" and "hybridize specifically" are used interchangeably to refer the ability of two nucleic acid molecules to hybridize under "stringent hybridization conditions." The phrase "stringent hybridization conditions" refers to conditions under which a nucleic acid molecule will hybridize to its target sequence, typically in a complex mixture of nucleic acids, but not detectably to other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 50° C. The antisense-oligonucleotides and derivatives thereof act on cells producing the proteins encoded by a CDCA1 or KNTC2 gene by binding to the DNA or mRNA encoding the protein, inhibiting transcription or translation thereof, promoting the degradation of the mRNAs and inhibiting the expression of the protein, thereby resulting in the inhibition of the protein function.

Antisense-oligonucleotides and derivatives thereof can be made into an external preparation, such as a liniment or a poultice, by mixing with a suitable base material which is inactive against the derivative.

The antisense-oligonucleotides of the invention inhibit the expression of at least one protein encoded by a CDCA1 or KNTC2 gene, and thus are useful for suppressing the biological activity of the respective protein.

The polynucleotides that inhibit one or more gene products of over-expressed genes also include small interfering RNAs (siRNA) composed of a combination of a sense strand nucleic acid and an antisense strand nucleic acid of the nucleotide sequence encoding an over-expressed protein encoded by a CDCA1 or KNTC2 gene. The term "siRNA" refers to a double stranded RNA molecule which prevents translation of a target mRNA. Standard techniques of introducing siRNA into the cell can be used in the treatment or prevention of the present invention, including those in which DNA is a template from which RNA is transcribed. The siRNA is constructed such that a single transcript has both the sense and complementary antisense sequences from the target gene, e.g., a hairpin.

The method is used to suppress gene expression of a cell having up-regulated expression of a CDCA1 or KNTC2 gene. Binding of the siRNA to a CDCA1 or KNTC2 gene transcript in the target cell results in a reduction of a CDCA1 or KNTC2 protein production by the cell. The length of the oligonucleotide is at least about 10 nucleotides and may be as long as the naturally occurring transcript. Preferably, the oligonucleotide is about 75, about 50 or about 25 nucleotides in length. Most preferably, the oligonucleotide is less than about 19 to about 25 nucleotides in length. A preferable siRNA used in the present invention has the general formula:

5'-[A]-[B]-[A']-3', wherein [A] is a ribonucleotide sequence corresponding to a target sequence of a CDCA1 or KNTC2 gene; [B] is a ribonucleotide sequence consisting of about 3 to about 23 nucleotides; and [A'] is a ribonucleotide sequence complementary to [A]. Herein, the phrase a "target sequence of a CDCA1 or KNTC2 gene" refers to a sequence that, when introduced into NSCLC cell lines, is effective for suppressing cell viability.

A preferred siRNA is an siRNA that reduces the expression of a KNTC2 gene, wherein the siRNA has the nucleotide sequence of SEQ ID NO: 9, in the sense strand. The siRNA has the general formula:

5'-[A]-[B]-[A']-3', wherein [A] is a ribonucleotide sequence corresponding to SEQ ID NO: 9; [B] is a ribonucleotide sequence composed of 3 to 23 nucleotides; and [A'] is a ribonucleotide sequence complementary to [A].

Furthermore, the nucleotide sequence of siRNAs may be designed using a siRNA design computer program available from the Ambion website (http://world wide web.ambion-.com/techlib/misc/siRNA_finder.html). The nucleotide sequences for the siRNA may be selected by a computer program based on the following protocol:

Selection of siRNA Target Sites:

1. Beginning with the AUG start codon of the transcript, scan downstream for AA dinucleotide sequences. Record the occurrence of each AA and the 3' adjacent 19 nucleotides as potential siRNA target sites. Tuschl, et al. *Genes Dev* 13(24): 3191-7 (1999), not recommend against designing siRNA against the 5' and 3' untranslated regions (UTRs) and regions near the start codon (within 75 bases) as these may be richer in regulatory protein binding sites, and thus the complex of endonuclease and siRNAs that were designed against these regions may interfere with the binding of UTR-binding proteins and/or translation initiation complexes.
2. Compare the potential target sites to the human genome database and eliminate from consideration any target sequences with significant homology to other coding sequences. The homology search can be performed using BLAST (Altschul S F, et al., Nucleic Acids Res. 1997; 25: 3389-402.; J Mol Biol. 1990; 215:403-10.), which can be found on the NCBI server at: world wide web.ncbi.nlm.nih.gov/BLAST/
3. Select qualifying target sequences for synthesis. On the website of Ambion, several preferable target sequences can be selected along the length of the gene for evaluation.

Transfection of vectors expressing siRNA polynucleotides of the invention can be used to inhibit growth of NSCLC cells. Thus, it is another aspect of the present invention to provide a double-stranded molecule comprising a sense-strand and antisense-strand which molecule functions as an siRNA for CDCA1 or KNTC2, and a vector encoding the double-stranded molecule.

The double-stranded molecule of the present invention includes a sense strand and an antisense strand, wherein the sense strand is a ribonucleotide sequence corresponding to a CDCA1 or KNTC2 target sequence, and wherein the antisense strand is a ribonucleotide sequence which is complementary to said sense strand, wherein said sense strand and said antisense strand hybridize to each other to form the double-stranded molecule, and wherein said double-stranded molecule, when introduced into a cell expressing a CDCA1 or KNTC2 gene, inhibits expression of said gene.

The double-stranded molecule of the present invention may be a polynucleotide derived from its original environment (i.e., when it is a naturally occurring molecule, the natural environment), physically or chemically altered from its natural state, or chemically synthesized. According to the present invention, such double-stranded molecules include those composed of DNA, RNA, and derivatives thereof. A DNA is suitably composed of bases such as A, T, C and G, and T is replaced by U in an RNA.

The vector of the present invention preferably includes a regulatory sequence adjacent to the region encoding the present double-stranded molecule that directs the expression of the molecule in an adequate cell. For example, the double-stranded molecules of the present invention are intracellularly transcribed by cloning their coding sequence into a vector containing, e.g., a RNA polymerase III transcription unit from the small nuclear RNA (snRNA) U6 or the human Hi RNA promoter.

Alternatively, the present vectors may be produced, for example, by cloning the target sequence into an expression vector so the objective sequence is operatively-linked to a regulatory sequence of the vector in a manner to allow expression thereof (transcription of the DNA molecule) (Lee, N. S. et al., *Nature Biotechnology* 20: 500-5 (2002)). For example, the transcription of an RNA molecule having an antisense sequence to the target sequence may be driven by a first promoter (e.g., a promoter sequence linked to the 3'-end of the cloned DNA) and that having the sense strand to the target sequence by a second promoter (e.g., a promoter sequence linked to the 5'-end of the cloned DNA). The expressed sense and antisense strands hybridize to each other in vivo to generate a siRNA construct to silence a gene that comprises the target sequence. Furthermore, two constructs (vectors) may be utilized to respectively produce the sense and anti-sense strands of a siRNA construct.

For introducing the vectors into a cell, transfection-enhancing agent can be used. FuGENE6 (Roche diagnostice), Lipofectamine 2000 (Invitrogen), Oligofectamine (Invitrogen), and Nucleofector (Wako pure Chemical) are useful as the transfection-enhancing agent.

The nucleic acids that inhibit one or more gene products of over-expressed genes also include ribozymes against such gene(s). In the context of the present invention, ribozymes inhibit the expression of the over-expressed CDCA1 or KNTC2 protein and are thereby useful for suppressing the biological activity of such protein. Therefore, a composition composed of such a ribozyme is useful in treating or preventing NSCLC.

Generally, ribozymes are classified into large ribozymes and small ribozymes. A large ribozyme is known as an enzyme that cleaves the phosphate ester bond of nucleic acids. After the reaction with the large ribozyme, the reacted site consists of a 5'-phosphate and 3'-hydroxyl group. The large ribozyme is further classified into (1) group I intron RNA catalyzing transesterification at the 5'-splice site by guanosine; (2) group II intron RNA catalyzing self-splicing through a two step reaction via lariat structure; and (3) RNA component of the ribonuclease P that cleaves the tRNA precursor at the 5' site through hydrolysis. On the other hand, small ribozymes have a smaller size (about 40 bp) as compared to the large ribozymes and cleave RNAs to generate a 5'-hydroxyl group and a 2'-3' cyclic phosphate. Hammerhead type ribozymes (Koizumi et al., *FEBS Lett.* 228: 225 (1988)) and hairpin type ribozymes (Buzayan, *Nature* 323: 349 (1986); Kikuchi and Sasaki, *Nucleic Acids Res.* 19: 6751 (1991)) are included in the small ribozymes. Methods for designing and constructing ribozymes are known in the art (see Koizumi et al., *FEBS Lett.* 228: 225 (1988); Koizumi et al., *Nucleic Acids Res.* 17: 7059-71 (1989); Kikuchi and Sasaki, *Nucleic Acids Res.* 19: 6751-5 (1991)) and ribozymes inhibiting the expression of an over-expressed NSC protein can be constructed based on the sequence information of the nucleotide sequence encoding a CDCA1 or KNTC2 protein according to conventional methods for producing ribozymes.

Alternatively, the function of one or more gene products of the over-expressed genes can be inhibited by administering a compound that binds to or otherwise inhibits the function of the gene products. An example of such a compound is an antibody that binds to the over-expressed gene product or gene products.

The present invention refers to the use of antibodies, particularly antibodies against a protein encoded by any of the up-regulated genes CDCA1 or KNTC2, or a fragment of such an antibody. As used herein, the term “antibody” refers to an immunoglobulin molecule having a specific structure that interacts (binds) specifically with a molecule comprising the antigen used for synthesizing the antibody (i.e., the up-regulated gene product) or with an antigen closely related to it. An antibody that binds to the over-expressed CDCA1 or KNTC2 nucleotide may be in any form, such as monoclonal or polyclonal antibodies, and includes antiserum obtained by immunizing an animal such as a rabbit with the polypeptide, all classes of polyclonal and monoclonal antibodies, human antibodies and humanized antibodies produced by genetic recombination. Furthermore, the antibody used in the method of treating or preventing NSCLC of the present invention may be a fragment of an antibody or a modified antibody, so long as it binds to one or more of the proteins encoded by the marker genes (a CDCA1 or KNTC2 gene). The antibodies and antibody fragments used in the context of the present method of treating or preventing NSCLC may be modified, and include chemically modified and chimeric antibodies. Such antibodies and antibody fragments can be obtained according to the above-mentioned methods, supra.

When the obtained antibody is to be administered to the human body (antibody treatment), a human antibody or a humanized antibody is preferable for reducing immunogenicity. For example, transgenic animals having a repertory of human antibody genes may be immunized with an antigen such as a CDCA1 or KNTC2 polypeptide, cells expressing the polypeptide, or their lysates. Antibody producing cells are then collected from the animals and fused with myeloma cells to obtain hybridoma, from which human antibodies against the polypeptide can be prepared (see WO92-03918, WO94-02602, WO94-25585, WO96-33735, and WO96-34096).

Alternatively, an immune cell, such as an immunized lymphocyte, producing antibodies may be immortalized by an oncogene and used for preparing monoclonal antibodies. The present invention provides a method for treating or preventing NSCLC, using an antibody against an over-expressed a CDCA1 or KNTC2 polypeptide. According to the method, a pharmaceutically effective amount of an antibody against a CDCA1 or KNTC2 polypeptide is administered. An antibody against an over-expressed CDCA1 or KNTC2 polypeptide is administered at a dosage sufficient to reduce the activity of a CDCA1 or KNTC2 protein. Alternatively, an antibody binding to a cell surface marker specific for tumor cells can be used as a tool for drug delivery. Thus, for example, an antibody against an over-expressed CDCA1 or KNTC2 polypeptide conjugated with a cytotoxic agent may be administered at a dosage sufficient to injure tumor cells.

In addition, dominant negative mutants of the proteins disclosed here can be used to treat or prevent NSCLC. For example, the present invention provides methods for treating or preventing NSCLC in a subject by administering a CDCA1 mutant having a dominant negative effect, or a polynucleotide encoding such a mutant. The CDCA1 mutant may include an amino acid sequence that includes a KNTC2 binding region, and excludes a nuf2 domain thereof. The CDCA1 mutant may have the amino acid sequence of SEQ ID NO: 35.

In some preferred embodiments, the CDCA1 mutant is linked to a membrane transducing agent. A number of peptide sequences have been characterized for their ability to translocate into live cells and can be used for this purpose in the present invention. Such membrane transducing agents (typically peptides) are defined by their ability to reach the cytoplasmic and/or nuclear compartments in live cells after internalization. Examples of proteins from which transducing agents may be derived include HIV Tat transactivator1, 2, the *Drosophila melanogaster* transcription factor Antennapedia3. In addition, nonnatural peptides with transducing activity have been used. These peptides are typically small peptides known for their membrane-interacting properties which are tested for translocation. The hydrophobic region within the secretion signal sequence of K-fibroblast growth factor (FGF), the venom toxin mastoparan (transportan)13, and Buforin I14 (an amphibian antimicrobial peptide) have been shown to be useful as transducing agents. For a review of transducing agents useful in the present invention see Joliot et al. *Nature Cell Biology* 6:189-196 (2004).

The CDCA1 mutant may have the general formula:

[R]-[D], wherein [R] is a membrane transducing agent, and [D] is a polypeptide having the amino acid sequence of SEQ ID NO: 35. In the general formula, [R] may directly link with [D], or indirectly link with [D] through a linker. Peptides or compounds having plural functional groups may be used as the linker. Specifically, an amino acid sequence of -GGG- may be used as the linker. Alternatively, the membrane transducing agent and the polypeptide having the amino acid sequence of SEQ ID NO: 35 can bind to the surface of micro-particle. In the present invention, [R] may link with arbitral region of [D]. For example, [R] may link with N-terminus or C-terminus of [D], or side chain of the amino acid residues constituting [D]. Furthermore, plural molecules of [R] may also link with one molecule of [D]. In some embodiments, plural molecules of [R]s may link with different site of [D]. In another embodiments, [D] may be modified with some [R]s linked together.

The membrane transducing agent can be selected from group listed below;

[poly-arginine]; Matsushita, M. et al, J Neurosci. 21, 6000-6007 (2003).

[Tat/RKKRRQRRR] (SEQ ID NO: 37) Frankel, A. et al, Cell 55, 1189-93 (1988).
Green, M. & Loewenstein, P. M. Cell 55, 1179-88 (1988).

[Penetratin/RQIKIWFQNRRMKWKK] (SEQ ID NO: 38)
Derossi, D. et al, J. Biol. Chem. 269, 10444-50 (1994).

[Buforin II/TRSSRAGLQFPVGRVHRLLRK] (SEQ ID NO: 39)
Park, C. B. et al. Proc. Natl. Acad. Sci. USA 97, 8245-50 (2000).

[Transportan/GWTLNSAGYLLGKINLKALAALAKKIL] (SEQ ID NO: 40)
Pooga, M. et al. FASEB J. 12, 67-77 (1998)

[MAP (model amphipathic peptide)/KLALKLALKALKAALKLA] (SEQ ID NO: 41)
Oehlke, J. et al. Biochim. Biophys. Acta. 1414, 127-39 (1998).

[K-FGF/AAVALLPAVLLALLAP] (SEQ ID NO: 42)
Lin, Y. Z. et al. J. Biol. Chem. 270, 14255-14258 (1995).

[Ku70/VPMLK] (SEQ ID NO: 43)
Sawada, M. et al. Nature Cell Biol. 5, 352-7 (2003).

[Ku70/PMLKE] (SEQ ID NO: 50)
Sawada, M. et al. Nature Cell Biol. 5, 352-7 (2003).

[Prion/MANLGYWLLALFVTMWTDVGLCKKR KP] (SEQ ID NO: 44)
Lundberg, P. et al. Biochem. Biophys. Res. Commun. 299, 85-90 (2002).

[pVEC/LLIILRRRIRKQAHAHSK] (SEQ ID NO: 45)
Elmquist, A. et al. Exp. Cell Res. 269, 237-44 (2001).

[Pep-1/KETWWETWWTEWSQPKKKRKV] (SEQ ID NO: 46)
Morris, M. C. et al. Nature Biotechnol. 19, 1173-76 (2001).

[SynB1/RGGRLSYSRRRFSTSTGR] (SEQ ID NO: 47)
Rousselle, C. et al. Mol. Pharmacol. 57, 679-86 (2000).

[Pep-7/SDLWEMMMVSLACQY] (SEQ ID NO: 48)
Gao, C. et al. Bioorg. Med. Chem. 10, 4057-65 (2002).

[HN-1/TSPLNIHNGQKL] (SEQ ID NO: 49)
Hong, F. D. & Clayman, G. L. Cancer Res. 60, 6551-6 (2000).

In the present invention, number of arginine residues that constitute the poly-arginine is not limited. In some preferred embodiments, 5 to 20 contiguous arginine residues may be exemplified. In a preferred embodiment, the number of arginine residues of the poly-arginine is 11 (SEQ ID NO:36).

As used herein, the phrase "dominant negative fragment of CDCA1" refers to a mutated form of CDCA1 that is capable of complexing with KNTC2. Thus, a dominant negative fragment is one that is not functionally equivalent to the full length CDCA1 polypeptide. Preferred dominant negative fragments are those that include a KNTC2 binding region, and exclude the nuf2 domain thereof.

Pharmaceutical Compositions for Treating or Preventing NSCLC

The present invention provides compositions for treating or preventing NSCLC that include a compound selected by the present method of screening for a compound that alters the expression or activity of a CDCA1 or KNTC2 gene. Such active ingredient can also be an antisense-oligonucleotide, siRNA or ribozyme against the gene, or derivatives, such as expression vector, of the antisense-oligonucleotide, siRNA or ribozyme, as described above.

When administering a compound isolated by the screening method of the present invention as a pharmaceutical for humans and other mammals, such as mice, rats, guinea-pig, rabbits, cats, dogs, sheep, pigs, cattle, monkeys, baboons or chimpanzees for treating a cell proliferative disease (e.g., non-small cell lung cancer), the isolated compound can be directly administered or can be formulated into a dosage form using conventional pharmaceutical preparation methods. Such pharmaceutical formulations of the present compositions include those suitable for oral, rectal, nasal, topical (including buccal and sub-lingual), vaginal or parenteral (including intramuscular, sub-cutaneous and intravenous) administration, or for administration by inhalation or insufflation. The formulations may be optionally packaged in discrete dosage units.

Pharmaceutical formulations suitable for oral administration include, but are not limited to, capsules, cachets or tablets, each containing a predetermined amount of the active ingredient. Illustrative formulations further include powders, granules, solutions, suspensions and emulsions. The active ingredient is optionally administered as a bolus electuary or paste. Tablets and capsules suitable for oral administration may contain conventional excipients, such as binding agents, fillers, lubricants, disintegrants and/or wetting agents. A tablet may be made by compression or molding, optionally with one or more formulational ingredients. Compressed tablets may be prepared by compressing in a suitable machine the active ingredients in a free-flowing form such as powder or granules, optionally mixed with a binder, lubricant, inert diluent, lubricating, surface active or dispersing agent. Molded tablets may be made via molding in a suitable machine a mixture of the powdered compound moistened with an inert liquid diluent. The tablets may be coated according to methods well known in the art. Oral fluid preparations may be in the form of, for example, aqueous or oily suspensions, solutions, emulsions, syrups or elixirs, or may be presented as a dry product for reconstitution with water or other suitable vehicle prior to use. Such liquid preparations may contain conventional additives such as suspending agents, emulsifying agents, non-aqueous vehicles (which may include edible oils) or preservatives. The tablets may optionally be formulated so as to provide slow or controlled release of the active ingredient in vivo. A package of tablets may contain one tablet to be taken on each of the month. The formulation or dose of medicament in these preparations makes a suitable dosage within the indicated range acquirable.

Exemplary formulations for parenteral administration include aqueous and non-aqueous sterile injection solutions which optionally contain anti-oxidants, buffers, bacteriostats and solutes which render the formulation isotonic with the blood of the intended recipient; and aqueous and non-aqueous sterile suspensions which may include, but are not limited to, suspending agents and thickening agents. The formulations may be presented in unit dose or multi-dose containers, for example sealed ampoules and vials, and may be stored in a freeze-dried (lyophilized) condition requiring only the addition of the sterile liquid carrier, for example, saline, water-for-injection, immediately prior to use. Alternatively, the formulations may be presented for continuous infusion. Extemporaneous injection solutions and suspensions may be prepared from sterile powders, granules and tablets of the kind previously described.

Exemplary formulations for rectal administration include suppositories with standard carriers such as cocoa butter or polyethylene glycol. Formulations for topical administration in the mouth, for example, buccally or sublingually, include lozenges, which contain the active ingredient in a flavored base such as sucrose and acacia or tragacanth, and pastilles comprising the active ingredient in a base such as gelatin, glycerin, sucrose or acacia. For intra-nasal administration of an active ingredient, a liquid spray or dispersible powder or in the form of drops may be used. Drops may be formulated with an aqueous or non-aqueous base also comprising one or more dispersing agents, solubilizing agents or suspending agents.

For administration by inhalation, the compositions may be conveniently delivered from an insufflator, nebulizer, pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the compositions may take the form of a dry powder composition, for example, a powder mix of an active ingredient and a suitable powder base such as lactose or starch. The powder composition may be presented in unit dosage form in, for example, capsules, cartridges, gelatin or blister packs from which the powder may be administered with the aid of an inhalator or insufflators.

Other suitable formulations include implantable devices and adhesive patches; which release a therapeutic agent.

When desired, the above-described formulations may be adapted to provide sustained release of the active ingredient. The pharmaceutical compositions may also contain other active ingredients, including, but not limited to, antimicrobial agents, immunosuppressants and preservatives.

It should be understood that in addition to the ingredients particularly mentioned above, the formulations of this invention may include other agents conventional in the art having regard to the type of formulation in question; for example, those suitable for oral administration may include flavoring agents.

Preferred unit dosage formulations are those containing an effective dose, as recited below, of the active ingredient or an appropriate fraction thereof.

For each of the aforementioned conditions, the compositions, e.g., polypeptides and organic compounds, may be administered orally or via injection at a dose of from about 0.1 to about 250 mg/kg per day. The dose range for adult humans is generally from about 5 mg to about 17.5 g/day, preferably about 5 mg to about 10 g/day, and most preferably about 100 mg to about 3 g/day. Tablets or other unit dosage forms of presentation provided in discrete units may conveniently contain an amount which is effective at such dosage or as a multiple of the same, for instance, units containing about 5 mg to about 500 mg, usually from about 100 mg to about 500 mg.

The dose employed will depend upon a number of factors, including the age and sex of the subject, the precise disorder being treated, and its severity. Also the route of administration may vary depending upon the condition and its severity.

As noted above, the present invention further provides a composition for treating or preventing NSCLC that contains an active ingredient that inhibits the expression of the over-expressed genes. The active ingredient may be made into an external preparation, such as liniment or a poultice, by mixing with a suitable base material which is inactive against the derivatives.

Also, as needed, the active ingredient can be formulated into tablets, powders, granules, capsules, liposome capsules, injections, solutions, nose-drops and freeze-drying agents by adding excipients, isotonic agents, solubilizers, preservatives, pain-killers and such. These can be prepared according to conventional methods for preparing nucleic acid containing pharmaceuticals.

Preferably, the antisense-oligonucleotide derivative, siRNA derivative or ribozyme derivative is given to the patient by direct application to the ailing site or by injection into a blood vessel so that it will reach the site of ailment. A mounting medium can also be used in the composition to increase durability and membrane-permeability. Examples of mounting mediums include liposome, poly-L-lysine, lipid, cholesterol, lipofectin and derivatives thereof.

The dosage of such compositions can be adjusted suitably according to the patient's condition and used in desired amounts. For example, a dose range of 0.1 to 100 mg/kg, preferably 0.1 to 50 mg/kg can be administered.

Another embodiment of the present invention is a composition for treating or preventing NSCLC composed of an antibody against a CDCA1 or KNTC2 polypeptide or fragments of the antibody that bind to the polypeptide.

Although dosages may vary according to the symptoms, an exemplary dose of an antibody or fragments thereof for treating or preventing NSCLC is about 0.1 mg to about 100 mg per day, preferably about 1.0 mg to about 50 mg per day and more preferably about 1.0 mg to about 20 mg per day, when administered orally to a normal adult (weight 60 kg).

When administering parenterally, in the form of an injection to a normal adult (weight 60 kg), although there are some differences according to the condition of the patient, symptoms of the disease and method of administration, it is convenient to intravenously inject a dose of about 0.01 mg to about 30 mg per day, preferably about 0.1 to about 20 mg per day and more preferably about 0.1 to about 10 mg per day. Also, in the case of other animals too, it is possible to administer an amount converted to 60 kg of body-weight.

The differentially expressed CDCA1 or KNTC2 gene identified herein can also allow for prognosis or monitoring the course of treatment of NSCLC. In this method, a test biological sample is provided from a subject undergoing treatment for NSCLC. If desired, multiple test biological samples are obtained from the subject at various time points, for example, before, during or after the treatment. The expression level of one or more of a CDCA1 or KNTC2 gene in the sample is then determined and compared to a reference sample with a known state of NSCLC that has not been exposed to the treatment. In some preferred embodiments of the present invention, the expression level of both of CDCA1 and KNTC2 gene may be detected.

If the reference sample contains no NSCLC cells, a similarity in the expression level of the CDCA1 or KNTC2 gene in the test biological sample and the reference sample indicates the efficaciousness of the treatment. However, a difference in the expression level of a CDCA1 or KNTC2 gene in the test as compared to the reference samples indicates a less favorable clinical outcome or prognosis. In the context of the present invention, NSCLC cells obtained from patients with a favorable prognosis may be used as the reference sample. For example, generally, when a patient could survive more than five years after the surgery, the patient had favorable prognosis. More specifically, long survivors (i.e. favorable prognosis) and short survivors (i.e. poor prognosis) groups include patients whose average 5-years tumor-specific survival rate was more than 69% and less than 45%, respectively. Thus, samples derived from such short survivors, and showing strong staining can be used as a positive control for poor prognosis. Alternatively, instead of the patient derived samples, samples or lung cancer cell lines showing strong staining similar to the patient derived samples can also be used as the positive control. Furthermore, in some embodiments, normal lung cells, lung cancer cells or other cells with no expression of CDCA1 and KNTC2 can be used as negative controls for poor prognosis.

The present invention also includes kits for predicting a NSCLC prognosis, wherein the kit includes one or more of the components selected from the group consisting of:

(a) a reagent for detecting the presence of an mRNA encoding the amino acid sequence of SEQ ID NO: 34 (CDCA1) or SEQ ID NO: 32 (KNTC2), (b) a reagent for detecting the presence of a protein having the amino acid sequence of SEQ ID NO: 34 (CDCA1) or SEQ ID NO: 32 (KNTC2), and (c) a reagent for detecting the biological activity of a protein having the amino acid sequence of SEQ ID NO: 34 (CDCA1) or SEQ ID NO: 32 (KNTC2).

In some preferred embodiments, (a) a reagent for detecting the presence of an mRNA encoding the amino acid sequence of SEQ ID NO: 34 (CDCA1) or SEQ ID NO: 32 (KNTC2) may be a nucleic acid that specifically binds to or identifies CDCA1 or KNTC2 nucleic acids, such as oligonucleotide sequences which are complementary to a CDCA1 or KNTC2 nucleic acid. Specifically, amino acid sequence of SEQ ID NO: 34 (CDCA1) and SEQ ID NO: 32 (KNTC2) are encoded by nucleotide sequence of SEQ ID NO: 33 and SEQ ID NO: 31. Thus, an oligonucleotide that includes the nucleotide sequence selected from nucleotide sequence of SEQ ID NO: 33 and SEQ ID NO: 31 may be used as preferable primer or probe of the present invention. Alternatively, in the present invention, (b) a reagent for detecting the presence of a protein including the amino acid sequence of SEQ ID NO: 34 (CDCA1) or SEQ ID NO: 32 (KNTC2) may be an antibody that bind to CDCA1 or KNTC2 proteins. Furthermore, (c) a reagent for detecting the biological activity of a protein including the amino acid sequence of SEQ ID NO: 34 (CDCA1) or SEQ ID NO: 32 (KNTC2) can be used for the kit of the present invention. The detection reagents may be packaged together in the form of a kit. The reagents are preferably packaged in separate containers, e.g., a nucleic acid or antibody (either bound to a solid matrix or packaged separately with reagents for binding them to the matrix), a control reagent (positive and/or negative), and/or a detectable label. Instructions (e.g., written, tape, VCR, CD-ROM, etc.) for carrying out the assay may also be included in the kit. The assay format of the kit may be a Northern hybridization or a sandwich ELISA, both of which are known in the art.

For example, the detection reagent may be immobilized on a solid matrix such as a porous strip to form at least one NSCLC detection site. The measurement or detection region of the porous strip may include a plurality of sites, each containing a nucleic acid. A test strip may also contain sites for negative and/or positive controls. Alternatively, control sites may be located on a separate strip from the test strip. Optionally, the different detection sites may contain different amounts of immobilized nucleic acids, i.e., a higher amount in the first detection site and lesser amounts in subsequent sites. Upon the addition of test sample, the number of sites displaying a detectable signal provides a quantitative indication of the prognosis of the sample. The detection sites may be configured in any suitably detectable shape and are typically in the shape of a bar or dot spanning the width of a test strip.

The following examples are presented to illustrate the present invention and to assist one of ordinary skill in making and using the same. The examples are not intended in any way to otherwise limit the scope of the invention. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. Any patents, patent applications and publications cited herein are incorporated by reference in their entirety.

EXAMPLES

The following examples are offered to illustrate, but not to limit the claimed invention.

Materials and Methods (a) Lung-Cancer Cell Lines and Tissue Samples: The human lung-cancer cell lines used in the following protocols were as follows: lung adenocarcinomas (ADC) A427, A549, LC319, PC3, PC9, PC14, NCI-H23, NCI-H522, and NCI-H1373; bronchioloalveolar cell carcinomas (BAC) NCI-H1666 and NCI-H1781; lung adenosquamous carcinomas (ASC) NCI-H226 and NCI-H647; lung squamous-cell carcinomas (SCC) RERF-LC-AI, SK-MES-1, EBC-1, LC176, LU61, NCI-H520, NCI-H1703, and NCI-H2170; a lung large-cell carcinoma (LCC) LX1; and small cell lung cancers (SCLC) DMS114, DMS273, SBC-3, and SBC-5. All cells were grown in monolayers in appropriate medium supplemented with 10% fetal calf serum (FCS) and were maintained at 37° C. in atmospheres of humidified air with 5% $CO_2$. Human small airway epithelial cells (SAEC) were grown in optimized medium (SAGM) purchased from Cambrex Bio Science Inc. (Walkersville, Md.). Primary NSCLC samples, of which 22 were classified as ADCs, 14 as SCCs, and one as ASC, had been obtained from 37 patients with written informed consent, as described previously (Kikuchi T, et al., Oncogene. 2003; 22(14):2192-205). An independent set of 16 additional primary NSCLCs, including eight ADCs and eight SCCs, were obtained along with adjacent normal lung-tissue samples from patients undergoing surgery. A total of 256 NSCLC and adjacent normal lung-tissue samples for immunostaining on tissue microarray and additional statistical analysis were also obtained from patients who underwent surgery. This study and the use of all clinical materials were approved by individual institutional Ethical Committee.

(b) Semiquantitative RT-PCR: Total RNA was extracted from cultured cells and clinical tissues using Trizol reagent (Life Technologies, Inc., Gaithersburg, Md.) according to the manufacturer's protocol. Extracted RNAs and normal human tissue poly(A) RNAs were treated with DNase I (Nippon Gene, Tokyo, Japan) and reversely-transcribed using oligo (dT) primer and SuperScript II reverse transcriptase (Invitrogen, Carlsbad, Calif.). Semiquantitative RT-PCR experiments were carried out with the following synthesized CDCA1-specific primers, KNTC2-specific primers or with ACTB-specific primers as an internal control:

```
CDCA1,
5'-GAGAAACTGAAGTCCCAGGAAAT-3'     (SEQ ID NO: 1)
and

5'-CTGATACTTCCATTCGCTTCAAC-3';    (SEQ ID NO: 2)

KNTC2,
5'-AAAAGAACCGAATCGTCTAGAGTC-3'    (SEQ ID NO: 29)
and

5'-CCGAGAGATCTTCTGACATGC-3';      (SEQ ID NO: 30)

ACTB,
5'-GAGGTGATAGCATTGCTTTCG-3'       (SEQ ID NO: 3)
and

5'-CAAGTCAGTGTACAGGTAAGC-3'.      (SEQ ID NO: 4)
```

PCR reactions were optimized for the number of cycles to ensure product intensity within the logarithmic phase of amplification.

(c) Northern-blot Analysis: Human multiple-tissue blots (BD Biosciences Clontech, Palo Alto, Calif.) were hybridized with a $^{32}$P-labeled PCR product of CDCA1 or KNTC2. The cDNA probes of CDCA1 and KNTC2 were prepared by RT-PCR using the primers described above. Pre-hybridization, hybridization, and washing were performed according to the supplier's recommendations. The blots were autoradiographed at room temperature for 30 hours with intensifying BAS screens (BIO-RAD, Hercules, Calif.).

(d) Antibodies: To obtain anti-CDCA1 antibody, the present inventors prepared plasmids expressing partial fragments of CDCA1 (codons 15-338) that contained His-tagged epitopes at their NH2-terminals using pET28 vector (Novagen, Madison, Wis.). The recombinant peptides were expressed in *Escherichia coli*, BL21 codon-plus strain (Stratagene, LaJolla, Calif.), and purified using TALON resin (BD Bioscience) according to the supplier's protocol. The protein, extracted on an SDS-PAGE gel, was inoculated into rabbits; the immune sera were purified on affinity columns according to standard methodology. Affinity-purified rabbit polyclonal anti-CDCA1 antibodies were used for western blotting, immunoprecipitation, and immunostaining. A goat polyclonal anti-KNTC2 antibody was purchased from abcam Inc. (Cambridge, Mass.). On western blots, the present inventors confirmed that the antibody was specific to CDCA1 or KNTC2, using lysates from NSCLC cell lines that either expressed CDCA1 and KNTC2 endogenously or not, or cells that had been transfected with a CDCA1 or KNTC2 expression vector.

(e) Western-blotting: Cells were lysed in lysis buffer; 50 mM Tris-HCl (pH 8.0), 150 mM NaCl, 0.5% NP-40, 0.5% deoxycholate-Na, 0.1% SDS, plus protease inhibitor (Protease Inhibitor Cocktail Set III; Calbiochem Darmstadt, Germany). The present inventors used an ECL western-blotting analysis system (GE Healthcare/Amersham Biosciences Corp, Piscataway, N.J.), as previously described (Ishikawa N, et al., Clin Cancer Res. 2004; 10(24):8363-70.).

(f) Identification of CDCA1-associated Proteins: Cell extracts from lung-cancer cell line LC319 were pre-cleared by incubation at 4° C. for 1 hour with 50 µl of protein A and G-agarose beads, in final volumes of 2 ml of immunoprecipitation buffer (0.5% NP-40, 50 mM Tris-HCl, 150 mM NaCl) in the presence of proteinase inhibitor. After centrifugation at 1,000 rpm for 5 min at 4° C., the supernatants were incubated at 4° C. with anti-CDCA1 polyclonal antibody, anti-KNTC2 polyclonal antibody, or normal rabbit IgG for 2 hours. After incubation at 4° C. for 1 hour with 50 µl of protein A and G-agarose beads, the beads were collected from each sample by centrifugation at 5,000 rpm for 2 min and washed six times with 1 ml of immunoprecipitation buffer, and the washed beads were re-suspended in 50 µl of Laemmli sample buffer and boiled for 5 min before the proteins were separated on 5-10% SDS PAGE gels (BIO RAD). After electrophoresis, the gels were stained with silver. Protein bands found specifically in extracts incubated with anti-CDCA1 polyclonal antibody were excised to serve for analysis by matrix-assisted laser desorption/ionization-time of flight mass spectrometry (MALDI-TOF-MS; AXIMA-CFR plus, SHIMADZU BIOTECH, Kyoto, Japan). To confirm the interaction between CDCA1 and KNTC2, the present inventors carried out the immunoprecipitation experiment. To achieve pCAGGSn3Fc-CDCA1, the present inventors cloned the entire coding sequence into the appropriate site of pCAGGSn3Fc-CDCA1 plasmid vector. The nucleotide sequence of each cDNA clone was determined with an ABI Prism 3700 DNA sequencer (Applied Biosystems, Foster City, Calif.), using T3, T7, or synthetic oligonucleotide primers according to the manufacturer's instructions. The extracts from LC319 cell transfected with pCAGGSn3Fc-CDCA1 were immunoprecipitated with KNTC2 polyclonal antibody (Abcom, Inc.) and normal rabbit IgG, respectively. Immunoblot was performed using anti-FLAG M2 monoclonal antibody (Sigma-Aldrich Co.).

(g) Identification of the KNTC2-binding region in CDCA1: Eleven deletion-constructs of CDCA1 (CDCA1 200-464, CDCA1 149-464, CDCA11-348, CDCA11-148, CDCA1 149-306, CDCA1 306-464, CDCA1 319-464, CDCA1 277-416, CDCA1 277-367, CDCA1 319-416, and CDCA1 319-367) were cloned into appropriate sites of C-terminal FLAG-tagged-pCAGGS vector. Cell extracts from lung-cancer cell line LC319, transfected with plasmids expressing eleven deletion-constructs of CDCA1 were pre-cleared by incubation at 4° C. for 1 hour with 100 µl of protein G-agarose beads in final volumes of 2 ml of immunoprecipitation buffer (0.5% NP-40, 50 mM Tris-HCl, 150 mM NaCl) in the presence of proteinase inhibitor. After centrifugation at 1,000 rpm for 5 min at 4° C., the supernatants were incubated at 4° C. with anti-FLAG M2 agarose for 2 hours. After the beads were collected from each sample by centrifugation at 5,000 rpm for 2 min and washed six times with 1 ml of immunoprecipitation buffer, the washed beads were re-suspended in 50 µl of Laemmli sample buffer and boiled for 5 min before the proteins were separated on 10% SDS PAGE gels. Immunoblot was performed using KNTC2 polyclonal antibody (Abcom, Inc.) and anti-FLAG M2 monoclonal antibody respectively (Sigma-Aldrich Co.).

(h) Immunocytochemistry: Cultured cells were washed twice with PBS(−), fixed in 4% formaldehyde solution for 60 min at room temperature, and rendered permeable by treatment for 1.5 minutes with PBS(−) containing 0.1% Triton X-100. Cells were covered with 3% BSA in PBS(−) for 60 minutes to block non-specific binding prior to the primary antibody reaction. The cells were then incubated with an antibody to human CDCA1 or KNTC2 protein. The immune complexes were stained with a goat anti-rabbit secondary antibody conjugated to Alexa488 (Molecular Probes, Eugene, Oreg.) and donkey anti-goat secondary antibody conjugated to Alexa594 (Molecular Probes), and viewed with a laser confocal microscope (TCS SP2 AOBS: Leica Microsystems, Wetzlar, Germany).

(i) Immunohistochemistry and Tissue-microarray Analysis: Tumor-tissue microarrays were constructed as published previously, using formalin-fixed NSCLCs (Ishikawa N, et al., Clin Cancer Res. 2004; 10(24):8363-70). Tissue areas for sampling were selected based on visual alignment with the corresponding HBE-stained sections on slides. Three, four, or five tissue cores (diameter 0.6 mm; height 3-4 mm) taken from donor-tumor blocks were placed into recipient paraffin blocks using a tissue microarrayer (Beecher Instruments, Sun Prairie, Wis.). A core of normal tissue was punched from each case. Five-μm sections of the resulting microarray block were used for immunohistochemical analysis. Positivity for CDCA1 and KNTC2 was assessed semiquantitatively by three independent investigators without prior knowledge of the clinical follow-up data, each of whom recorded staining intensity as absent (scored as 0), weak (1+) or strongly positive (2+). Lung-cancers were scored as strongly positive (2+) only if all reviewers defined them as such. To investigate the presence of CDCA1/KNTC2 protein in clinical materials, the present inventors stained tissue sections using ENVISION+ KitRP (DakoCytomation, Glostrup, Denmark). Affinity-purified anti-CDCA1 antibody or anti-KNTC2 antibody was added after blocking of endogenous peroxidase and proteins, and each section was incubated with HRP-labeled anti-rabbit or anti-goat IgG as the secondary antibody. Substrate-chromogen was added and the specimens were counterstained with hematoxylin.

(j) Statistical Analysis: The present inventors attempted to correlate clinicopathological variables such as age, gender, and pathological TNM stage with the expression levels of CDCA1 and/or KNTC2 protein determined by tissue-microarray analysis. Tumor-specific survival curves were calculated from the date of surgery to the time of death related to NSCLC, or to the last follow-up observation. Kaplan-Meier curves were calculated for each relevant variable and for CDCA1/KNTC2 expression; differences in survival times among patient subgroups were analyzed using the log-rank test. Univariate and multivariate analyses were performed with the Cox proportional-hazard regression model to determine associations between clinicopathological variables and cancer-related mortality. First, the present inventors analyzed associations between death and possible prognostic factors including age, gender, pT-classification, and pN-classification, taking into consideration one factor at a time. Second, multivariate Cox analysis was applied on backward (stepwise) procedures that always forced CDCA1/KNTC2 expression into the model, along with any and all variables that satisfied an entry level of a p value less than 0.05. As the model continued to add factors, independent factors did not exceed an exit level of $P<0.05$.

(k) RNA Interference Assay: The present inventors previously established a vector-based RNA interference (RNAi) system, psiH1BX3.0, that was designed to synthesize siRNAs in mammalian cells (Shimokawa T, et al., Cancer Res. 2003; 63(19):6116-20). A siRNA expression vector against CDCA1 (si-CDCA1) and KNTC2 (si-KNTC2) was prepared by cloning of double-stranded oligonucleotides in Table 1 into the BbsI site in the psiH1BX vector. 10 μg of siRNA-expression vector was transfected using 301 of Lipofectamine 2000 (Invitrogen) into NSCLC cell lines, A549 and LC319. The transfected cells were cultured for seven days in the presence of appropriate concentrations of geneticin (G418), and the number of colonies was counted by Giemsa staining, and viability of cells was evaluated by MTT assay at 7 days after the treatment; briefly, cell-counting kit-8 solution (DOJINDO, Kumamoto, Japan) was added to each dish at a concentration of 1/10 volume, and the plates were incubated at 37° C. for additional 4 hours. Absorbance was then measured at 490 nm, and at 630 nm as a reference, with a Microplate Reader 550 (BIO-RAD). To confirm suppression of CDCA1 or KNTC2 mRNA expression, semiquantitative RT-PCR experiments were carried out with the following synthesized CDCA1-specific primers and KNTC2-specific primers according to the standard protocol. The target sequences of the synthetic oligonucleotides for RNAi were as follows: (EGFP: enhanced green fluorescent protein (GFP) gene, a mutant of *Aequorea victoria* GFP), 5'-GAAGCAGCACGACTTCTTC-3' (SEQ ID NO: 5); control 2 (Scramble: chloroplast *Euglena gracilis* gene coding for 5S and 16S rRNAs), 5'-GCGCGCTTTGTAGGATTCG-3' (SEQ ID NO: 6); control 3 (Luciferase: *Photinus pyralis* luciferase gene), 5'-CGTACGCGGAATACTTCGA-3' (SEQ ID NO: 7); siRNA-CDCA1-#2,5'-AAGATGCTGCTGAAAGGGAGA-3' (SEQ ID NO: 8); siRNA-KNTC2-#1,5'-GCTGGATGATCTTTACCAA-3' (SEQ ID NO: 9).

TABLE 1

Sequences of specific double-stranded oligonucleotide inserted into siRNA expression vector and target sequences of each siRNAs

| gene | | Nucleotide Sequence | SEQ ID NO: |
|---|---|---|---|
| EGFP | insert | TCCCGAAGCAGCACGACTTCTTCTTCAAGAGAGAAGAAGTCGTGCTGCTTC | 14 |
| EGFP | insert | AAAAGAAGCAGCACGACTTCTTCTCTCTTGAAGAAGAAGTCGTGCTGCTTC | 15 |
| EGFP | hairpin | GAAGCAGCACGACTTCTTCTTCAAGAGAGAAGAAGTCGTGCTGCTTC | 16 |
| SCR | insert | TCCCGCGCGCTTTGTAGGATTCGTTCAAGAGACGAATCCTACAAAGCGCGC | 17 |
| SCR | insert | AAAAGCGCGCTTTGTAGGATTCGTCTCTTGAACGAATCCTACAAAGCGCGC | 18 |
| SCR | hairpin | GCGCGCTTTGTAGGATTCGTTCAAGAGACGAATCCTACAAAGCGCGC | 19 |
| LUC | insert | TCCCCGTACGCGGAATACTTCGATTCAAGAGATCGAAGTATTCCGCGTACG | 20 |
| LUC | insert | AAAACGTACGCGGAATACTTCGATCTCTTGAATCGAAGTATTCCGCGTACG | 21 |
| LUC | hairpin | CGTACGCGGAATACTTCGATTCAAGAGATCGAAGTATTCCGCGTACG | 22 |
| CDCA1 | insert | TCCCAAGATGCTGCTGAAAGGGAGATTCAAGAGATCTCCCTTTCAGCAGCATCTT | 23 |
| CDCA1 | insert | AAAAAAGATGCTGCTGAAAGGGAGATCTCTTGAATCTCCCTTTCAGCAGCATCTT | 24 |
| CDCA1 | hairpin | AAGATGCTGCTGAAAGGGAGATTCAAGAGATCTCCCTTTCAGCAGCATCTT | 25 |
| KNTC2 | insert | TCCCGCTGGATGATCTTTACCAATTCAAGAGATTGGTAAAGATCATCCAGC | 26 |

TABLE 1-continued

Sequences of specific double-stranded oligonucleotide inserted into siRNA expression vector and target sequences of each siRNAs

| gene | | Nucleotide Sequence | SEQ ID NO: |
|---|---|---|---|
| KNTC2 | insert | AAAAGCTGGATGATCTTTACCAATCTC TTGAATTGGTAAAGATCATCCAGC | 27 |
| KNTC2 | hairpin | GCTGGATGATCTTTACCAATTCAAGAG ATTGGTAAAGATCATCCAGC | 28 |

(l) Synthesized Dominant-negative Peptide: Dominant-negative 20 or 19 amino-acid sequences derived from the KNTC2 binding domain of CDCA1 were covalently linked at their N-termini to a membrane transducing 11 poly-arginine sequence (11R). Four dominant-negative peptides were synthesized; 11R-CDCA1 368-387, RRRRRRRRRR-GGG-QYKRTVIEDCNKVQEKRGAV (SEQ ID NO: 10); 11R-CDCA1 378-397, RRRRRRRRR-GGG-NKVQEKRGAVYERVTTINQE (SEQ ID NO: 11), 11R-CDCA1 388-407, RRRRRRRRRR-GGG-YERVTTINQEIQKIKLGIQQ (SEQ ID NO:12); 11R-CDCA1 398-416 RRRRRRRRR-GGG-IQKIKLGIQQLKDAAEREK (SEQ ID NO: 13). Peptides were purified by preparative reverse-phase HPLC and were >95% purity.

(m) Effect of 11R-peptides on lung-cancer cell growth: LC319 and A546 and normal human lung fibroblast derived MRC5 cells were incubated with 11R-peptides at the concentration of 5 μM, 10 μM, and 20 μM for seven days. The medium was exchanged every other day at the appropriate concentrations of each peptide and the viability of cells was evaluated by MTT assay at 7 days after the treatment; briefly, cell-counting kit-8 solution (DOJINDO, Kumamoto, Japan) was added to each dish at a concentration of 1/10 volume, and the plates were incubated at 37° C. for additional 4 hours. Absorbance was then measured at 490 nm, and at 630 nm as a reference, with a Microplate Reader 550 (BIO-RAD). Flow-cytometric analysis was performed as described previously (Suzuki, C. et al. Cancer Res. 65, 11314-11325 (2005).).

(n) Mouse model: The animal experiments were conducted according to the institutional and national guidelines for the care and use of laboratory animals, and approved by the institutional animal use committee. $1\times10^6$ of A549 cells were subcutaneously implanted into the right shoulder of 6-week-old male BALB/c nude mice (nu/nu). Two weeks after the injection, the mice with tumor (30 $mm^3$ volume on average) were randomized into three groups and intratumorly administered with 11R-CDCA1398-416 peptides (0.15 μmol/body/day), scramble (0.15 μmol/body/day), or PBS (control) for 7 weeks. Tumor volume was measured once a day by using a caliper and applying the data to the formula (volume=0.52×[width]$^2$×[length]) to calculate the volume of a spheroid.

Results (a) Co-activation of the CDCA1 and KNTC2 Gene: Using a cDNA microarray representing 23,040 genes to screen for elements that were highly transactivated in a large proportion of NSCLCs, CDCA1 (Accession NO. hCT1957725 (Celera) SEQ ID NO: 33, 34) was identified as a good candidate. This gene showed a 3-fold or higher level of expression in the great majority of the NSCLC cases examined. Subsequently, its transactivation was confirmed by semiquantitative RT-PCR experiments in 10 of 16 additional NSCLC cases (4 of 8 ADCs; 6 of 8 SCCs) (FIG. 1A). Up-regulation of CDCA1 was observed in all of the 23 NSCLC and SCLC cell lines examined, while the transcript was hardly detectable in SAEC cells derived from normal bronchial epithelium (FIG. 1B). The endogenous expression of the CDCA1 protein was confirmed on western blots using anti-CDCA1 antibody in 12 lung-cancer cell lines (data not shown). Northern-blot analysis using CDCA1 cDNA as a probe identified a 2.4-kb transcript; observed exclusively and abundantly only in testis, suggested that CDCA1 is atypical cancer-testis antigen (FIG. 1C).

(b) Identification of KNTC2 as a Protein Interacting with CDCA1: To elucidate the function of CDCA1 in lung-cancer cells, the present inventors first looked for protein(s) that would interact with CDCA1. Lysates of LC319 cells were extracted and immunoprecipitated with anti-CDCA1 antibody. Protein complexes were stained with SilverQuest (Invitrogen) on SDS-PAGE gels. A 75-kDa band, which was seen in cell lysates immunoprecipitated with anti-CDCA1 but not with normal rabbit IgG, was extracted and its peptide sequence was determined by MALDI-TOF mass spectrometry. This procedure identified KNTC2 (GenBank Accession NO. NM_006101, SEQ ID NO: 31, 32) as a candidate for CDCA1-interacting protein. The cognate interaction between exogenous CDCA1 and endogenous KNTC2 was confirmed by an immunoprecipitation experiment (FIG. 2A).

Figure 2:
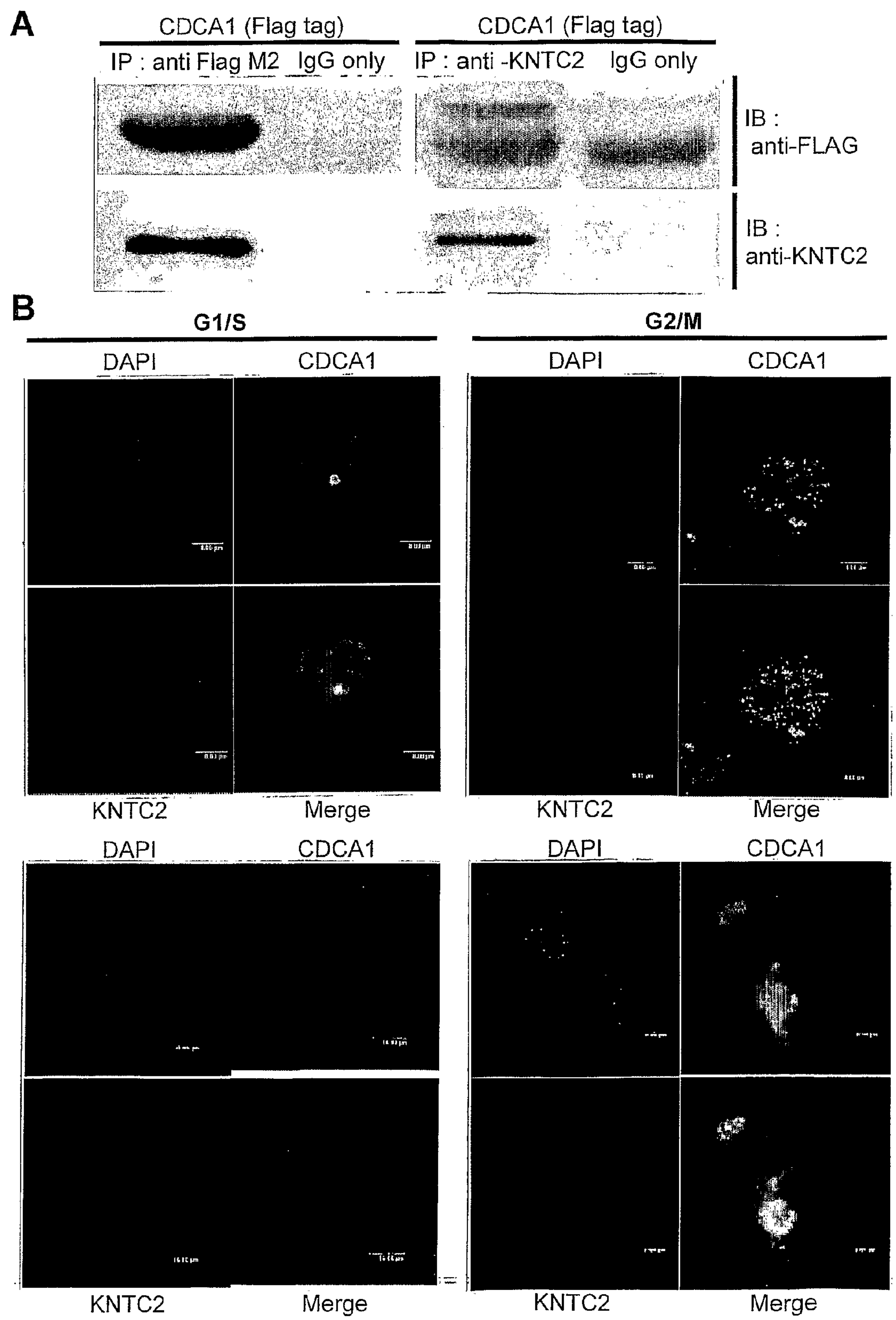
FIG. 2 depicts the interaction of CDCA1 with KNTC2 and the subcellular localization of the resulting complex.

To determine the subcellular localization of endogenous CDCA1 and KNTC2 in lung-cancer cells, immunocytochemical analysis was performed using a rabbit polyclonal anti-CDCA1 and a goat polyclonal anti-KNTC2 antibodies; co-localization of both the proteins mainly at centrosome and nucleus in G1/S phase, and centrosome and centromere at G2/M was detected (FIG. 2B).

Primary NSCLC tissues and lung-cancer cell lines were subsequently re-examined and found increased KNTC2 expression in 9 of 16 NSCLC clinical samples (3 of 8 ADCs; 6 of 8 SCCs) by semiquantitative RT-PCR experiments as well as in all of 23 lung-cancer cell lines (FIG. 1A, B). The higher mRNA expression pattern of the CDCA1 and KNTC2 genes relative to those of ACTB gene were significantly correlated in clinical samples (P<0.001 by $\chi^2$-test). These two genes were also co-activated in almost all lung-cancer cell lines examined (P<0.001 by $\chi^2$-test). Northern blotting using KNTC2 cDNA as a probe identified a 2.5-kb transcript, exclusively and abundantly in testis, indicating that KNTC2 was belonged to the category of cancer-testis antigen (FIG. 1C). The expression distribution patterns of KNTC2 in lung cancers and normal tissues were very similar to those of CDCA1.

(c) Identification of the KNTC2-binding region in CDCA1: To determine the specific domain of CDCA1 required for interaction with KNTC2, one of six deletion-constructs of CDCA1 with COOH(C)-terminal FLAG-sequences (CDCA1 200-464, CDCA1 149-464, CDCA11-348, CDCA11-148, CDCA1 149-306, and CDCA1 306-464) were transfected into LC319 cells. Immunoprecipitation with monoclonal anti-Flag indicated that the CDCA11-148 and CDCA1 149-306 constructs, which lost C-terminal 158 amino-acids, were unable to interact with endogenous KNTC2 (FIG. 2C). To further determine the minimal KNTC2-binding domain of CDCA1, one of additional five deletion-constructs of CDCA1 with C-terminal FLAG-sequences (CDCA1 319-464, CDCA1 277-416, CDCA1 277-367, CDCA1 319-416, and CDCA1 319-367) were transfected into LC319 cells. Immunoprecipitation with monoclonal anti-Flag antibody indicated that the CDCA1 277-367 and CDCA1 319-367 constructs, which lost 49 amino-acids of CDCA1 368-416, were unable to interact with endogenous KNTC2 (FIG. 2D).

Figure 3:
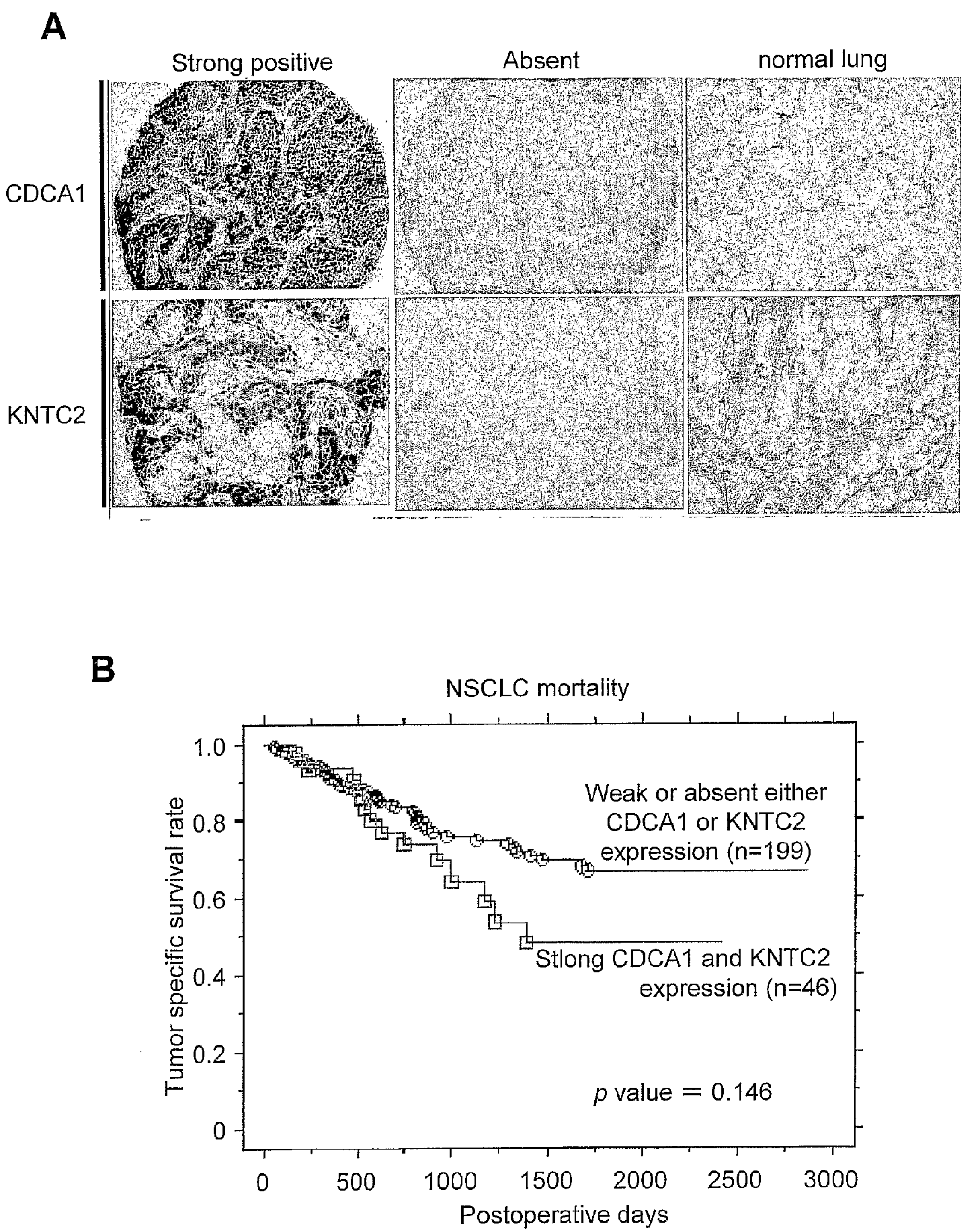
FIG. 3 depicts the association of CDCA1 and KNTC2 over-expression with worse outcomes in NSCLC.

(d) Association of Over-expression of CDCA1 and KNTC2 with Poor Prognosis: Using tissue microarrays prepared from 256 NSCLCs, immunohistochemical analysis was performed with affinity-purified anti-CDCA1 and KNTC2 polyclonal antibodies and positive staining was found in 225 (88%) and 225 (88%) cases respectively. Of those, CDCA1 staining was positive for 117 of 138 ADC tumors (85%); 72 of 80 cases were SCCs (90%); 19 of 21 were LCCs (90%); all of 10 BAC (100%) and all of 7 ASC cases (100%), while KNTC2 staining was positive for 113 of 138 were ADC tumors (82%); 75 of 80 cases were SCCs (94%); 20 of 21 were LCCs (95%); all of 10 BAC (100%) and all of 7 ASC cases (100%). All of these tumors were surgically-resected NSCLCs, and no staining was observed in any of their adjacent normal lung tissues (FIG. 3A). The expression pattern of CDCA1 protein was significantly concordant with KNTC2 protein expression in these tumors (P<0.001 by $\chi^2$-test), confirming the results by RT-PCR and western-blotting. Patterns of CDCA1/KNTC2 expression were classified as absent/weak (scored as 0~1+) or strong (scored as 2+). Cases with tumors that represent both CDCA1 and KNTC2 strongly positive were likely to be worse prognosis (P=0.146 by the Log-rank test; FIG. 3B). The definition of the long-term and short term survivors in this CDCA1/KNTC2 immunostaining test is as follows:

Long survivors: Patients belonging to a group of patients whose average 5-years survival rate was at least 69%, and Short survivors: Patients belonging to a group of patients whose average 5-years survival rate was no more than 45%.

Furthermore, using tissue microarrays prepared from 282 paraffin-embedded NSCLCs, immunohistochemical analysis was performed with affinity-purified anti-CDCA1 and anti-KNTC2 polyclonal antibodies. Patterns of CDCA1/KNTC2 expression was classified as absent/weak (scored as 0~1+) or strong (scored as 2+). Of the 282 NSCLC cases examined, 95 (33.7%) revealed strong CDCA1 staining (score 2+), 113 (40.1%) were stained weakly (score 1+), and no staining (score 0) was observed in 74 cases (26.2%). For KNTC2, strong staining (score 2+) was observed in 112 cases (39.7%), weak staining (score 1+) in 122 cases (43.3%), and no staining (score 0) in 48 cases (17%). All of these tumors were surgically-resected NSCLC cases, and no staining was observed in any of their adjacent normal lung tissues (FIG. 1*c*). 189 of the 282 tumors were positive (scored as 1+~2+) for both CDCA1 and KNTC2, and 29 were negative for the both proteins. 19 of the 282 cases were positive for only CDCA1 and 45 were positive for only KNTC2. The fact that the expression pattern of CDCA1 protein was significantly concordant with KNTC2 protein expression in these tumors (P<0.0001 by $\chi^2$-test) further confirmed the results by RT-PCR and western-blotting, suggesting that there might be common transcriptional regulator(s) for CDCA1 and KNTC2. Strong expression of CDCA1 in NSCLCs was significantly associated with pT factor status ($\chi^2$=5.473, P=0.019) and with tumor-specific 5-year survival (P=0.0233 by the Log-rank test) (FIG. 3C). Strong expression of KNTC2 in NSCLCs was significantly associated with pT factor ($\chi^2$=11.664, P=0.0006) and 5 year-survival (P=0.0384 by the Log-rank test) (FIG. 3D). NSCLC patients whose tumors expressed neither CDCA1 nor KNTC2 could receive the best survival benefit, while patients with strong positive values for both markers suffered the shortest tumor-specific survival (P=0.0250 by the Log-rank test; FIG. 3E). Using univariate analysis, the present inventors found that node status (N0 vs N1, N2: P<0.0001; score test), tumor size (T1 vs T2, T3, T4: P<0.001; score test), and high CDCA1/KNTC2 expression (P=0.0233, 0.0384, respectively; score test) were important correlative features for poor prognoses of patients with NSCLC.

Figure 4:
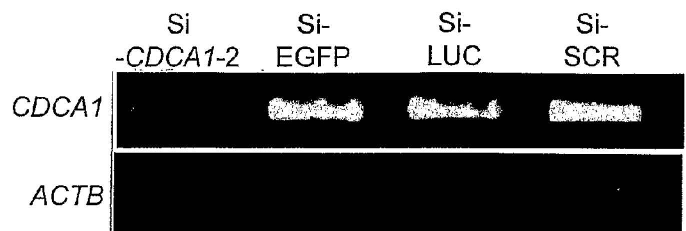
FIG. 4 depicts the inhibition of growth of NSCLC cells by siRNAs against CDCA1 and KNTC2.
Figure 4:
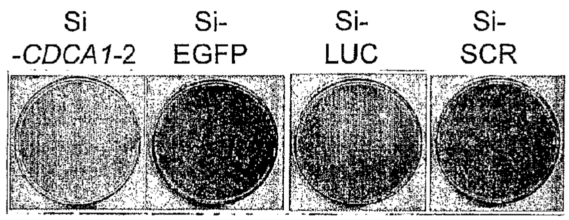
Figure 4:
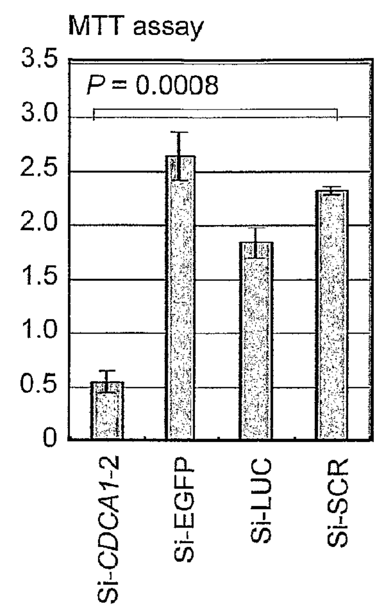
Figure 4:
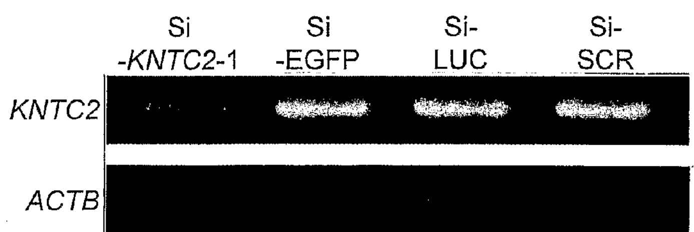
Figure 4:
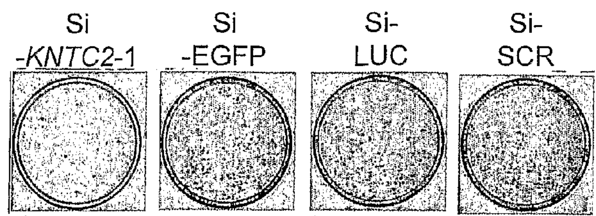
Figure 4:
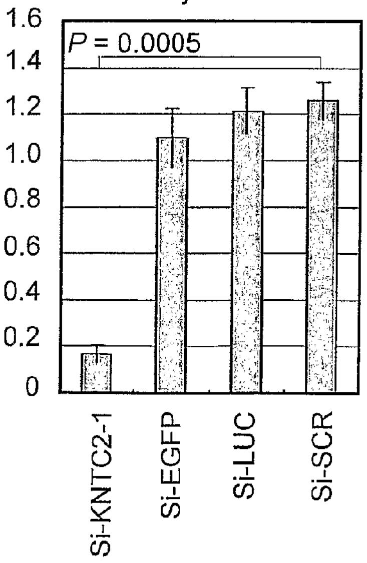

(e) Inhibition of Growth of NSCLC Cells by Specific siRNA against CDCA1 and KNTC2: To assess whether CDCA1 and KNTC2 are essential for growth or survival of lung-cancer cells, plasmids were constructed to express siRNA against CDCA1 (si-CDCA1) or KNTC2 (si-KNTC2), using siRNAs for EGFP, Luciferase, and Scramble as controls. Transfection of either of the plasmids (si-CDCA1-#2 or si-KNTC2#1) into A549 or LC319 cells significantly suppressed expression of endogenous CDCA1 or KNTC2 proteins in comparison with the controls, and resulted in significant decreases in cell viability and colony numbers measured by MTT (P=0.0008 and 0.0005 respectively by unpaired t-test) and colony-formation assays (representative data of A549 was shown in FIG. 4A, B).

Figure 5:
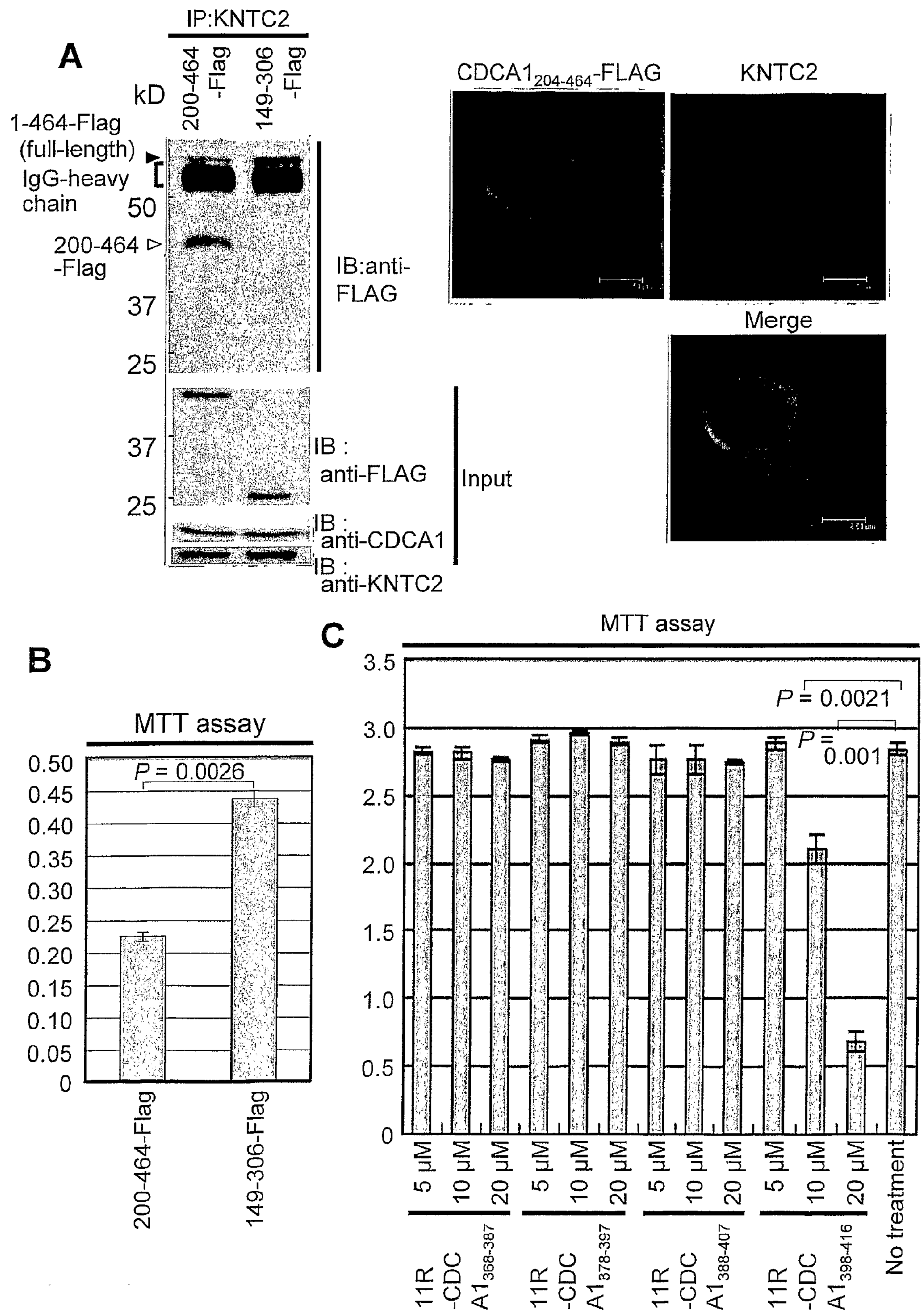
FIG. 5 depicts the inhibition of growth of NSCLC cells by a dominant-negative CDCA1 fragment and peptides.

(f) Inhibition of Growth of NSCLC Cells by Dominant-negative Peptides of CDCA1: To investigate the functional significance of CDCA1-KNTC2 interaction for growth or survival of lung-cancer cells, a deletion fragment of CDCA1 which lacked the N-terminal portion of CDCA1 but had shown strongest affinity to endogenous KNTC2 (CDCA1 200-464; see FIG. 2C), compared with other deletion mutants, was examined for a dominant-negative function of suppressing direct interaction between CDCA1 and KNTC2. Since the band of endogenous CDCA1 immunoprecipitated with anti-CDCA1/KNTC2 antibody overlapped with IgG-heavy chain bands, it was difficult to detect the interaction between endogenous CDCA1 and KNTC2. Therefore, to confirm the suppression of direct interaction between CDCA1 and KNTC2 by CDCA1 200-464 construct, the two combination of plasmids; CDCA11-464 (full length) and CDCA1 200-464 or CDCA11-464 (full length) and CDCA1 149-306 (control) that was unable to interact with endogenous KNTC2 (FIG. 5A; left second-top panel) were co-transfected into LC319 cells. Interaction of only CDCA1 1-464 (full length) or CDCA1 200-464 with endogenous KNTC2 was detected by immunoprecipitation using anti-KNTC2 polyclonal antibody (FIG. 5A; left top panel; black and white arrows). It was further confirmed that over-expression of the CDCA1 200-464 reduced complex formation between exogenous CDCA1 (CDCA11-464; full length) and endogenous KNTC2 (FIG. 5A; left top panel; black arrow). Co-localization of CDCA1 200-464 and endogenous KNTC2 in the LC319 cells was also confirmed by immunocytochemistry (FIG. 5A; right panels). Next, the plasmids encoding CDCA1 200-464 were transfected into LC319 cells to detect the dominant-negative effect of this construct. Expectedly, transfection of the dominant-negative fragment of CDCA1 200-464 resulted in significant decreases in cell viability as measured by MTT assay (P=0.0026 by unpaired t-test, CDCA1 200-464 vs CDCA1 149-306; FIG. 5B).

Figure 6:
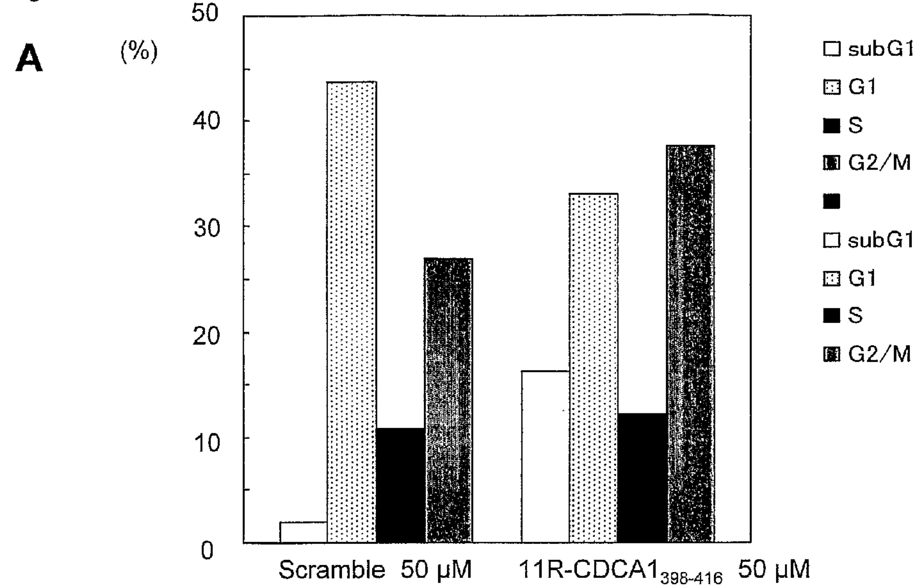
FIG. 6 depicts the inhibition of growth of NSCLC cells by dominant-negative peptides of CDCA1.
Figure 6:
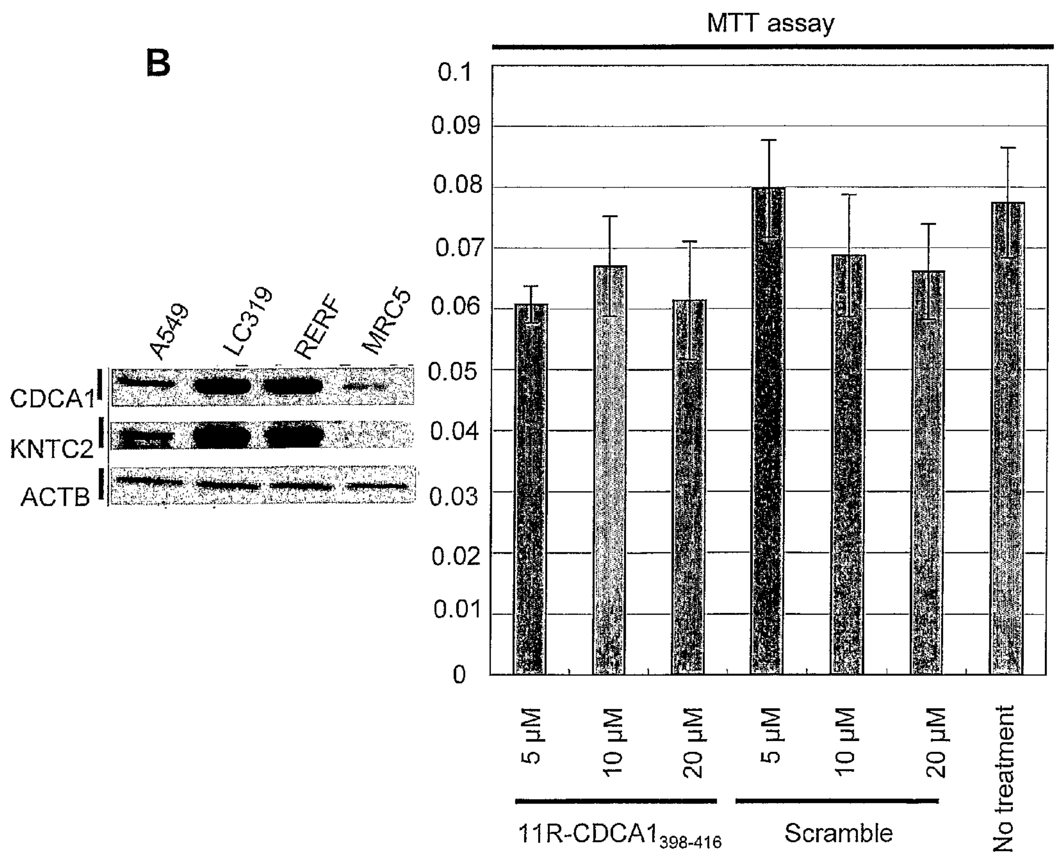

As shown in FIG. 2D, 49 amino-acid peptides of CDCA1 368-416, were supposed to be the most important region to interact with endogenous KNTC2. To develop the bioactive cell-permeable compounds that can inhibit the CDCA1-KNTC2 complex formation in vivo, four amino-acids polypeptides covering the KNTC2 binding domain of CDCA1 368-416 that covalently linked at its N terminus to a membrane transducing 11 poly-arginine sequence (11R) were synthesized. To test the effect of these poly-arginine-linked peptides on lung-cancer cell growth/survival, LC319 cells were treated with one of the four CDCA1-derived peptides individually. Transfection of the 11R-CDCA1 398-416 resulted in significant and dose-dependent decreases in cell viability, as measured by MTT assay (FIG. 5C; P=0.001 or 0.0021 by unpaired t-test). 72 hours after the 11R-CDCA1398-416 treatment, several cells had progressed through the cell cycle and blocked at mitosis, exhibiting a rounded cellular morphology that was very similar to the effect of either CDCA1 or KNTC2 suppression with siRNAs (data not shown). In contrast, there was no difference in cellular morphology between the non-treated cells and those treated with non-effective peptides, both of which exhibited normal distribution of interphase cells in spread shape and mitotic cells in rounded shape. To clarify the mechanism of tumor suppression by 11R-CDCA1398-416 peptides, flow cytometric analysis of the tumor cells treated with these peptides was performed, and it was discovered that the cells caused the G2/M arrest and sub-G1 fraction at 72 hours after the treatment was significantly increased (FIG. 6A). 11R-CDCA1398-416 revealed no effect on cell viability of normal human lung fibroblast derived MRC5 cells that expressed a hardly detectable level of CDCA1 and KNTC2 (FIG. 6B). These data suggest that transducible 11R-CDCA1398-416 peptides could inhibit a functional complex formation of CDCA1 and KNTC2 and have no toxic effect on normal human cells that do not express these proteins.

Figure 7:
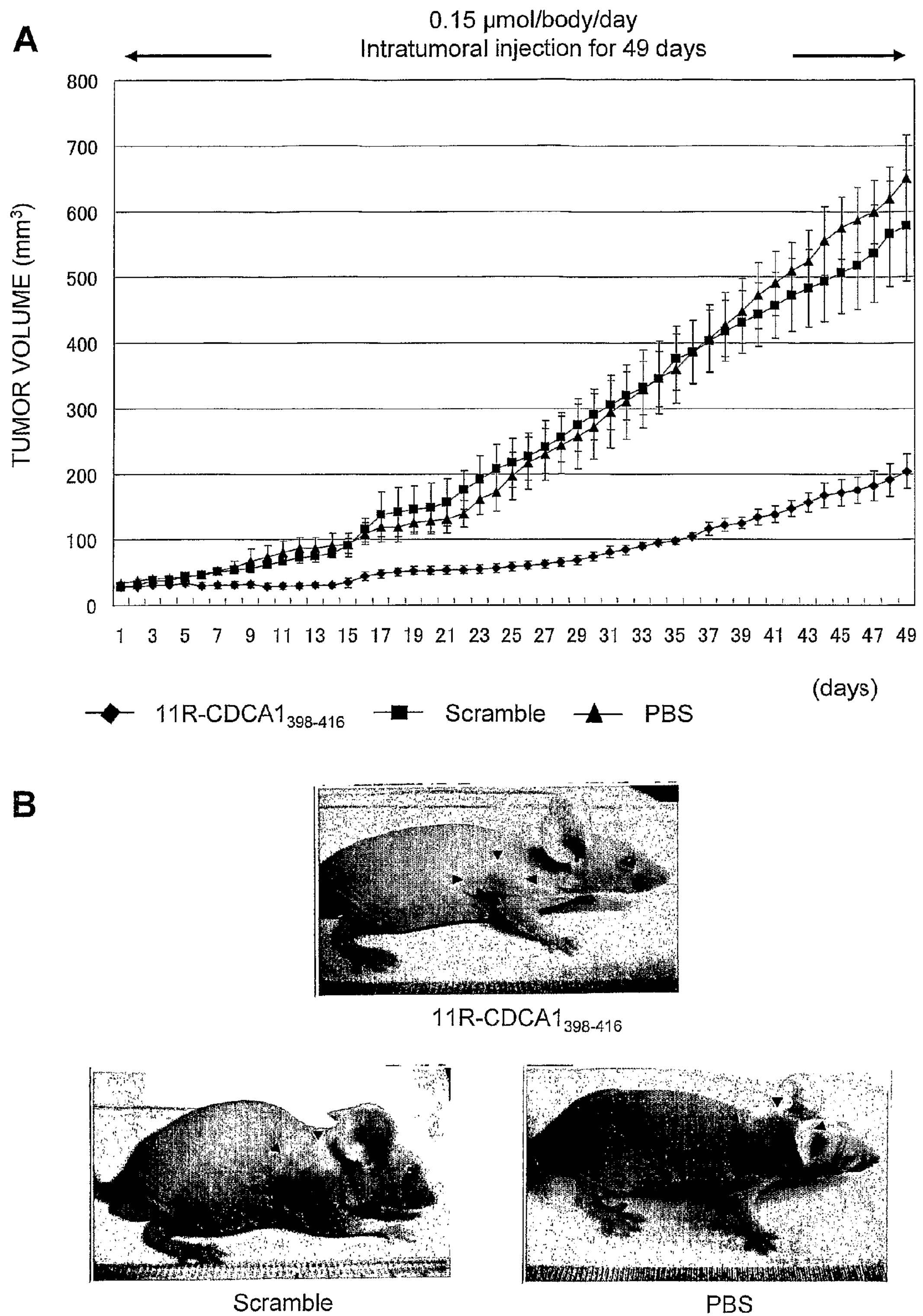
FIG. 7 depicts the in vivo growth suppression of NSCLC cells by cell-permeable CDCA1-peptides.

(g) In vivo growth inhibition of NSCLC cells by dominant-negative peptides: To further investigate the in vivo tumor suppressive effect of the dominant-negative peptides of CDCA1, A549 cells were subcutaneously transplanted to right shoulder of 6-week-old BALB/c mice and treated the mice by intratumoral injection of the 11R-CDCA1398-416 peptide (0.15 μmol/body/day), scramble peptides (0.15 μmol/body/day), or PBS (control) for 7 weeks. There was no difference in body weight or food intake among three treatment groups (data not shown). Tumor growth was significantly suppressed by the 11R-CDCA1398-416 peptide, but not by scramble peptides or PBS (FIGS. 7A, B). These data suggested that dominant-negative peptides of CDCA1 had the growth suppressive effect on cancer cells in vitro and in vivo, and that inhibition of the CDCA1-KNTC2 interaction might be a promising target for developing novel type of anti-cancer drugs.

Discussion

Although many molecular targets for lung cancer therapy have been reported, to date, few agents have been shown to exert biological activity against cancer in a clinical setting while minimizing negative side effects. Therefore, the present inventors sought to identify up-regulated genes with the goal of developing a novel small compound for lung cancer therapy. The strategy was as follows: 1) identify up-regulated genes in NSCLC by the genome wide screening using the cDNA microarray system, 2) verify that the candidate genes had minimal expression in normal organs by multiple tissue northern blot, 3) confirm over-expression and correlation with clinicopathological factors in hundreds of NSCLC tissue samples by tissue microarray, and 4) verify that the targeted gene is essential for the survival or growth of lung cancer cells by siRNA. Through this systematic approach, two novel cancer-testis antigens, CDCA1 and KNTC2, were identified as co-over-expressed in the great majority of clinical NSCLC samples and cell lines. In addition, a complex formed by the products of these genes was found to be indispensable for growth and progression of NSCLC cells.

CDCA1 and KNTC2 were indicated to be involved in the regulation of mitosis (Ciferri, C. et al. J Biol Chem. 280, 29088-95 (2005).). A large proportion of the proteins that regulate mitosis are aberrantly expressed in human tumor cells when compared to their normal counterparts, and some of them are known to function as oncogenes (Nicholas, K. and Stephen, T. Nat Rev Cancer. 4, 927-36 (2004).). A subset thereof has also been expected to represent a possible source of target molecules for development of novel anti-cancer agents. For example, highly conserved aurora kinases represent one of such families that are critical as mitotic regulators (Doggrell, S. A. Expert Opin Investig Drugs. 13, 1199-201 (2004).). Indeed, several aurora-kinase inhibitors including ZM447439, Hesperadin, and VX-680, have recently been described as anti-cancer drugs (Doggrell, S. A. Expert Opin Investig Drugs. 13, 1199-201 (2004); Harrington, E. A. et al. Nat Med. 10, 262-7 (2004).). In this study, the present inventors found by tissue microarray analysis that NSCLC patients showing abundant expression of CDCA1/KNTC2 revealed a shorter tumor-specific survival period, thus suggesting that CDCA1, along with KNTC2, plays important roles in progression of lung cancers.

A novel molecular target is expected to have an estimated minimal diverse effect as well as to have a powerful biological activity against cancer. CDCA1 and KNTC2 are both known to be cell cycle regulators, and by means of our MTN screening, the present inventors demonstrated that these two proteins belonged to cancer-testis antigens. The present inventors also demonstrated that CDCA1 and KNTC2 were over-expressed simultaneously in NSCLCs. Immunohistochemical analysis on tissue microarrays prepared from 256 or 282 NSCLCs, revealed that patients with NSCLC showing strong positive staining of both the proteins were likely to represent a shorter tumor-specific survival times, suggesting that CDCA1, along with KNTC2, plays a crucial role for progression lung cancers. Furthermore, suppression of endogenous CDCA1 or KNTC2 reduced their expression and suppressed growth of A549 and LC319 cells. In addition, the present inventors demonstrated for the first time that these binding were blocked by a dominant-negative form of CDCA1 protein and synthesized 33 amino-acids polypeptide composed of the membrane transducing poly-arginine sequence and CDCA1-derived 19 amino-acids peptides (codons 398-416), and subsequently the growth of lung cancer cells were suppressed effectively. Recently, several groups reported that inhibition of the interaction between the molecules led to loss of function of the complex. For example, the covalent linkage of a short cell-permeable peptide to a 20 amino-acid sequence derived from the JNK binding domain of JNK-interacting protein-1 (JIP-1) has lead to the improvement of insulin resistance and ameliorated glucose tolerance in diabetic mice (Kaneto H, et al., Nat Med. 2004; 10:1128-32). In addition, a cell-permeable peptide (SN50) blocked translocation of NF-[kappa]B after activation by external stimuli (Lin Y Z, et al., J Biol Chem. 1995; 270:14255-8). Blocking NF-[kappa]B protects [beta]-cells from IL-1[beta]-induced apoptosis (Stephens L A, et al., J Autoimmun. 1997; 10:293-8). Similar approaches have been successfully used for blocking activating protein 1 (AP-1), a nuclear factor of activated T-cells (NFAT), and signal transducer and activator of transcription (STAT) 1 nuclear import (Torgerson T R, et al., J Immunol. 1998; 161:6084-92; Bonny C, et al., Diabetes. 2001; 50:77-82). All of these indicated that the conversion of large proteins into small compounds is amenable to success. Selective killing of tumor cells with no or minimum toxic effect to normal cells is most desirable in the treatment of cancer patients. Chen et al. reported that cell membrane-permeable peptides containing the motif inhibiting the phosphorylation of substrates by cyclin A (CCNA)/cyclin-dependent kinase 2 (CDK2) or cyclin E (CCNE)/CDK2 induced cancer cells to undergo apoptosis at a relative higher level than non-transformed cells (Chen, Y. N. et al. Proc Natl Acad Sci USA. 96, 4325-9 (1999).). The anti- MDM2 peptide blocking p53-MD2 interaction was also reported to induce rapid accumulation of p53, activation of apoptosis-inducing genes, preferential killing of retinoblastoma cells, and minimal retinal damage after intravitreal injection (Harbour, J. W. et al. Arch. Opthalmol. 2, 1341-6 (2002).). Our results using cell permeable peptides specifically targeting cancer cells, suggest that inhibition of CDCA1-KNTC2 complex provide a rationale for development of novel antagonists as anti-neoplastic agents.

In summary, the present inventors have found that the CDCA1-KNTC2 cancer-testis antigen complex plays a specific functional role in the growth and/or survival of cancer cells. Our data show the feasibility of designing new anti-cancer peptides as well as small compounds to specifically target the activity of CDCA1 and KNTC2 and/or the their complex, as a therapeutic strategy for treatment of lung-cancer patients.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The invention claimed is:

1. A method of assessing a non-small cell lung cancer prognosis, wherein the method comprises the steps of:

(a) detecting the expression level of a cell division associated 1 (CDCA1) gene encoding a protein consisting of the amino acid sequence of SEQ ID NO: 34 in a non-small cell lung cancer specimen collected from a subject whose non-small cell lung cancer prognosis is to be assessed, and (b) indicating a poor prognosis when an elevation in the expression level of CDCA1 is detected.

2. The method of claim 1, wherein the method further comprises the steps of:

(c) detecting the expression level of a kinetocore associated 2 (KNTC2) gene encoding a protein consisting of the amino acid sequence of SEQ ID NO: 32 in a non-small cell lung cancer specimen collected from a subject whose non-small cell lung cancer prognosis is to be assessed, and (d) indicating a poor prognosis when an elevation in the expression level of a KNTC2 gene is detected.

3. The method of claim 1, wherein the expression level is detected by any one of the methods selected from the group consisting of:

(a) detecting the presence of an mRNA encoding the amino acid sequence of SEQ ID NO: 34, and (b) detecting the presence of a protein consisting of the amino acid sequence of SEQ ID NO: 34.

* * * * *

SEQUENCE LISTING

```
<160> NUMBER OF SEQ ID NOS: 50

<210> SEQ ID NO 1
<211> LENGTH: 23
<212> TYPE: DNA
<213> ORGANISM: Artificial
<220> FEATURE:
<223> OTHER INFORMATION: An artificially synthesized primer sequence
      for RT-PCR

<400> SEQUENCE: 1

gagaaactga agtcccagga aat                                           23


<210> SEQ ID NO 2
<211> LENGTH: 23
<212> TYPE: DNA
<213> ORGANISM: Artificial
<220> FEATURE:
<223> OTHER INFORMATION: Artificially synthesized primer sequence for
      RT-PCR

<400> SEQUENCE: 2

ctgatacttc cattcgcttc aac                                           23


<210> SEQ ID NO 3
<211> LENGTH: 21
<212> TYPE: DNA
<213> ORGANISM: Artificial
<220> FEATURE:
<223> OTHER INFORMATION: An artificially synthesized primer sequence
      for RT-PCR

<400> SEQUENCE: 3

gaggtgatag cattgctttc g                                             21


<210> SEQ ID NO 4
<211> LENGTH: 21
<212> TYPE: DNA
<213> ORGANISM: Artificial
<220> FEATURE:
<223> OTHER INFORMATION: An artificially synthesized primer sequence
      for RT-PCR

<400> SEQUENCE: 4

caagtcagtg tacaggtaag c                                             21


<210> SEQ ID NO 5
<211> LENGTH: 19
<212> TYPE: DNA
<213> ORGANISM: Artificial
<220> FEATURE:
<223> OTHER INFORMATION: target sequence for siRNA
```

<400> SEQUENCE: 5
gaagcagcac gacttcttc 19

<210> SEQ ID NO 6
<211> LENGTH: 19
<212> TYPE: DNA
<213> ORGANISM: Artificial
<220> FEATURE:
<223> OTHER INFORMATION: target sequence for siRNA

<400> SEQUENCE: 6
gcgcgctttg taggattcg 19

<210> SEQ ID NO 7
<211> LENGTH: 19
<212> TYPE: DNA
<213> ORGANISM: Artificial
<220> FEATURE:
<223> OTHER INFORMATION: target sequence for siRNA

<400> SEQUENCE: 7
cgtacgcgga atacttcga 19

<210> SEQ ID NO 8
<211> LENGTH: 21
<212> TYPE: DNA
<213> ORGANISM: Artificial
<220> FEATURE:
<223> OTHER INFORMATION: target sequence for siRNA

<400> SEQUENCE: 8
aagatgctgc tgaaagggag a 21

<210> SEQ ID NO 9
<211> LENGTH: 19
<212> TYPE: DNA
<213> ORGANISM: Artificial
<220> FEATURE:
<223> OTHER INFORMATION: target sequence for siRNA

<400> SEQUENCE: 9
gctggatgat ctttaccaa 19

<210> SEQ ID NO 10
<211> LENGTH: 34
<212> TYPE: PRT
<213> ORGANISM: Artificial
<220> FEATURE:
<223> OTHER INFORMATION: An artificially synthesized peptide sequence for dominant-negative construct

<400> SEQUENCE: 10

```
Arg Arg Arg Arg Arg Arg Arg Arg Arg Arg Arg Gly Gly Gly Gln Tyr
1               5                   10                  15

Lys Arg Thr Val Ile Glu Asp Cys Asn Lys Val Gln Glu Lys Arg Gly
            20                  25                  30

Ala Val
```

<210> SEQ ID NO 11
<211> LENGTH: 34
<212> TYPE: PRT
<213> ORGANISM: Artificial
<220> FEATURE:
<223> OTHER INFORMATION: An artificially synthesized peptide sequence for dominant-negative construct

<400> SEQUENCE: 11

```
Arg Arg Arg Arg Arg Arg Arg Arg Arg Arg Arg Gly Gly Gly Asn Lys
1               5                   10                  15

Val Gln Glu Lys Arg Gly Ala Val Tyr Glu Arg Val Thr Thr Ile Asn
            20                  25                  30

Gln Glu
```

<210> SEQ ID NO 12
<211> LENGTH: 34
<212> TYPE: PRT
<213> ORGANISM: Artificial
<220> FEATURE:
<223> OTHER INFORMATION: An artificially synthesized peptide sequence for dominant-negative construct

<400> SEQUENCE: 12

```
Arg Arg Arg Arg Arg Arg Arg Arg Arg Arg Arg Gly Gly Gly Tyr Glu
1               5                   10                  15

Arg Val Thr Thr Ile Asn Gln Glu Ile Gln Lys Ile Lys Leu Gly Ile
            20                  25                  30

Gln Gln
```

<210> SEQ ID NO 13
<211> LENGTH: 33
<212> TYPE: PRT
<213> ORGANISM: Artificial
<220> FEATURE:
<223> OTHER INFORMATION: An artificially synthesized peptide sequence for dominant-negative construct

<400> SEQUENCE: 13

```
Arg Arg Arg Arg Arg Arg Arg Arg Arg Arg Arg Gly Gly Gly Ile Gln
1               5                   10                  15

Lys Ile Lys Leu Gly Ile Gln Gln Leu Lys Asp Ala Ala Glu Arg Glu
            20                  25                  30

Lys
```

<210> SEQ ID NO 14
<211> LENGTH: 51
<212> TYPE: DNA
<213> ORGANISM: Artificial
<220> FEATURE:
<223> OTHER INFORMATION: An artificially synthesized oligonucleotide for constructing of siRNA expression vector

<400> SEQUENCE: 14

```
tcccgaagca gcacgacttc ttcttcaaga gagaagaagt cgtgctgctt c              51
```

<210> SEQ ID NO 15
<211> LENGTH: 51
<212> TYPE: DNA
<213> ORGANISM: Artificial
<220> FEATURE:
<223> OTHER INFORMATION: An artificially synthesized oligonucleotide for constructing of siRNA expression vector

<400> SEQUENCE: 15

```
aaaagaagca gcacgacttc ttctctcttg aagaagaagt cgtgctgctt c              51
```

<210> SEQ ID NO 16
<211> LENGTH: 47
<212> TYPE: DNA
<213> ORGANISM: Artificial

<220> FEATURE:
<223> OTHER INFORMATION: hairpin structure for siRNA

<400> SEQUENCE: 16
gaagcagcac gacttcttct tcaagagaga agaagtcgtg ctgcttc 47

<210> SEQ ID NO 17
<211> LENGTH: 51
<212> TYPE: DNA
<213> ORGANISM: Artificial
<220> FEATURE:
<223> OTHER INFORMATION: An artificially synthesized oligonucleotide for constructing of siRNA expression vector

<400> SEQUENCE: 17
tcccgcgcgc tttgtaggat tcgttcaaga gacgaatcct acaaagcgcg c 51

<210> SEQ ID NO 18
<211> LENGTH: 51
<212> TYPE: DNA
<213> ORGANISM: Artificial
<220> FEATURE:
<223> OTHER INFORMATION: An artificially synthesized oligonucleotide for constructing of siRNA expression vector

<400> SEQUENCE: 18
aaaagcgcgc tttgtaggat tcgtctcttg aacgaatcct acaaagcgcg c 51

<210> SEQ ID NO 19
<211> LENGTH: 47
<212> TYPE: DNA
<213> ORGANISM: Artificial
<220> FEATURE:
<223> OTHER INFORMATION: hairpin structure for siRNA

<400> SEQUENCE: 19
gcgcgctttg taggattcgt tcaagagacg aatcctacaa agcgcgc 47

<210> SEQ ID NO 20
<211> LENGTH: 51
<212> TYPE: DNA
<213> ORGANISM: Artificial
<220> FEATURE:
<223> OTHER INFORMATION: An artificially synthesized oligonucleotide for constructing of siRNA expression vector

<400> SEQUENCE: 20
tccccgtacg cggaatactt cgattcaaga gatcgaagta ttccgcgtac g 51

<210> SEQ ID NO 21
<211> LENGTH: 51
<212> TYPE: DNA
<213> ORGANISM: Artificial
<220> FEATURE:
<223> OTHER INFORMATION: An artificially synthesized oligonucleotide for constructing of siRNA expression vector

<400> SEQUENCE: 21
aaaacgtacg cggaatactt cgatctcttg aatcgaagta ttccgcgtac g 51

<210> SEQ ID NO 22
<211> LENGTH: 47
<212> TYPE: DNA
<213> ORGANISM: Artificial
<220> FEATURE:
<223> OTHER INFORMATION: hairpin structure for siRNA

<400> SEQUENCE: 22
cgtacgcgga atacttcgat tcaagagatc gaagtattcc gcgtacg 47

<210> SEQ ID NO 23
<211> LENGTH: 55
<212> TYPE: DNA
<213> ORGANISM: Artificial
<220> FEATURE:
<223> OTHER INFORMATION: An artificially synthesized oligonucleotide for constructing of siRNA expression vector

<400> SEQUENCE: 23
tcccaagatg ctgctgaaag ggagattcaa gagatctccc tttcagcagc atctt 55

<210> SEQ ID NO 24
<211> LENGTH: 55
<212> TYPE: DNA
<213> ORGANISM: Artificial
<220> FEATURE:
<223> OTHER INFORMATION: An artificially synthesized oligonucleotide for constructing of siRNA expression vector

<400> SEQUENCE: 24
aaaaaagatg ctgctgaaag ggagatctct tgaatctccc tttcagcagc atctt 55

<210> SEQ ID NO 25
<211> LENGTH: 51
<212> TYPE: DNA
<213> ORGANISM: Artificial
<220> FEATURE:
<223> OTHER INFORMATION: siRNA hairpin design

<400> SEQUENCE: 25
aagatgctgc tgaaagggag attcaagaga tctccctttc agcagcatct t 51

<210> SEQ ID NO 26
<211> LENGTH: 51
<212> TYPE: DNA
<213> ORGANISM: Artificial
<220> FEATURE:
<223> OTHER INFORMATION: An artificially synthesized oligonucleotide for constructing of siRNA expression vector

<400> SEQUENCE: 26
tcccgctgga tgatctttac caattcaaga gattggtaaa gatcatccag c 51

<210> SEQ ID NO 27
<211> LENGTH: 51
<212> TYPE: DNA
<213> ORGANISM: Artificial
<220> FEATURE:
<223> OTHER INFORMATION: An artificially synthesized oligonucleotide for constructing of siRNA expression vector

<400> SEQUENCE: 27
aaaagctgga tgatctttac caatctcttg aattggtaaa gatcatccag c 51

<210> SEQ ID NO 28
<211> LENGTH: 47
<212> TYPE: DNA
<213> ORGANISM: Artificial
<220> FEATURE:
<223> OTHER INFORMATION: siRNA hairpin design

<400> SEQUENCE: 28
gctggatgat ctttaccaat tcaagagatt ggtaaagatc atccagc 47

```
<210> SEQ ID NO 29
<211> LENGTH: 24
<212> TYPE: DNA
<213> ORGANISM: Artificial
<220> FEATURE:
<223> OTHER INFORMATION: An artificially synthesized primer sequence
      for RT-PCR

<400> SEQUENCE: 29

aaaagaaccg aatcgtctag agtc                                             24


<210> SEQ ID NO 30
<211> LENGTH: 21
<212> TYPE: DNA
<213> ORGANISM: Artificial
<220> FEATURE:
<223> OTHER INFORMATION: An artificially synthesized primer sequence
      for RT-PCR

<400> SEQUENCE: 30

ccgagagatc ttctgacatg c                                                21


<210> SEQ ID NO 31
<211> LENGTH: 2150
<212> TYPE: DNA
<213> ORGANISM: Homo sapiens
<220> FEATURE:
<221> NAME/KEY: CDS
<222> LOCATION: (105)..(2033)

<400> SEQUENCE: 31

ctcgagccac gaaggccccg ctgtcctgtc tagcagatac ttgcacggtt tacagaaatt      60

cggtccctgg gtcgtgtcag gaaactggaa aaaaggtcat aagc atg aag cgc agt      116
                                                 Met Lys Arg Ser
                                                 1

tca gtt tcc agc ggt ggt gct ggc cgc ctc tcc atg cag gag tta aga       164
Ser Val Ser Ser Gly Gly Ala Gly Arg Leu Ser Met Gln Glu Leu Arg
5                   10                  15                  20

tcc cag gat gta aat aaa caa ggc ctc tat acc cct caa acc aaa gag       212
Ser Gln Asp Val Asn Lys Gln Gly Leu Tyr Thr Pro Gln Thr Lys Glu
                25                  30                  35

aaa cca acc ttt gga aag ttg agt ata aac aaa ccg aca tct gaa aga       260
Lys Pro Thr Phe Gly Lys Leu Ser Ile Asn Lys Pro Thr Ser Glu Arg
            40                  45                  50

aaa gtc tcg cta ttt ggc aaa aga act agt gga cat gga tcc cgg aat       308
Lys Val Ser Leu Phe Gly Lys Arg Thr Ser Gly His Gly Ser Arg Asn
        55                  60                  65

agt caa ctt ggt ata ttt tcc agt tct gag aaa atc aag gac ccg aga       356
Ser Gln Leu Gly Ile Phe Ser Ser Ser Glu Lys Ile Lys Asp Pro Arg
    70                  75                  80

cca ctt aat gac aaa gca ttc att cag cag tgt att cga caa ctc tgt       404
Pro Leu Asn Asp Lys Ala Phe Ile Gln Gln Cys Ile Arg Gln Leu Cys
85                  90                  95                  100

gag ttt ctt aca gaa aat ggt tat gca cat aat gtg tcc atg aaa tct       452
Glu Phe Leu Thr Glu Asn Gly Tyr Ala His Asn Val Ser Met Lys Ser
                105                 110                 115

cta caa gct ccc tct gtt aaa gac ttc ctg aag atc ttc aca ttt ctt       500
Leu Gln Ala Pro Ser Val Lys Asp Phe Leu Lys Ile Phe Thr Phe Leu
            120                 125                 130

tat ggc ttc ctg tgc ccc tca tac gaa ctt cct gac aca aag ttt gaa       548
Tyr Gly Phe Leu Cys Pro Ser Tyr Glu Leu Pro Asp Thr Lys Phe Glu
        135                 140                 145

gaa gag gtt cca aga atc ttt aaa gac ctt ggg tat cct ttt gca cta       596
Glu Glu Val Pro Arg Ile Phe Lys Asp Leu Gly Tyr Pro Phe Ala Leu
```

```
    150                 155                 160

tcc aaa agc tcc atg tac aca gtg ggg gct cct cat aca tgg cct cac      644
Ser Lys Ser Ser Met Tyr Thr Val Gly Ala Pro His Thr Trp Pro His
165                 170                 175                 180

att gtg gca gcc tta gtt tgg cta ata gac tgc atc aag ata cat act      692
Ile Val Ala Ala Leu Val Trp Leu Ile Asp Cys Ile Lys Ile His Thr
                185                 190                 195

gcc atg aaa gaa agc tca cct tta ttt gat gat ggg cag cct tgg gga      740
Ala Met Lys Glu Ser Ser Pro Leu Phe Asp Asp Gly Gln Pro Trp Gly
            200                 205                 210

gaa gaa act gaa gat gga att atg cat aat aag ttg ttt ttg gac tac      788
Glu Glu Thr Glu Asp Gly Ile Met His Asn Lys Leu Phe Leu Asp Tyr
        215                 220                 225

acc ata aaa tgc tat gag agt ttt atg agt ggt gcc gac agc ttt gat      836
Thr Ile Lys Cys Tyr Glu Ser Phe Met Ser Gly Ala Asp Ser Phe Asp
    230                 235                 240

gag atg aat gca gag ctg cag tca aaa ctg aag gat tta ttt aat gtg      884
Glu Met Asn Ala Glu Leu Gln Ser Lys Leu Lys Asp Leu Phe Asn Val
245                 250                 255                 260

gat gct ttt aag ctg gaa tca tta gaa gca aaa aac aga gca ttg aat      932
Asp Ala Phe Lys Leu Glu Ser Leu Glu Ala Lys Asn Arg Ala Leu Asn
                265                 270                 275

gaa cag att gca aga ttg gaa caa gaa aga gaa aaa gaa ccg aat cgt      980
Glu Gln Ile Ala Arg Leu Glu Gln Glu Arg Glu Lys Glu Pro Asn Arg
            280                 285                 290

cta gag tcg ttg aga aaa ctg aag gct tcc tta caa gga gat gtt caa     1028
Leu Glu Ser Leu Arg Lys Leu Lys Ala Ser Leu Gln Gly Asp Val Gln
        295                 300                 305

aag tat cag gca tac atg agc aat ttg gag tct cat tca gcc att ctt     1076
Lys Tyr Gln Ala Tyr Met Ser Asn Leu Glu Ser His Ser Ala Ile Leu
    310                 315                 320

gac cag aaa tta aat ggt ctc aat gag gaa att gct aga gta gaa cta     1124
Asp Gln Lys Leu Asn Gly Leu Asn Glu Glu Ile Ala Arg Val Glu Leu
325                 330                 335                 340

gaa tgt gaa aca ata aaa cag gag aac act cga cta cag aat atc att     1172
Glu Cys Glu Thr Ile Lys Gln Glu Asn Thr Arg Leu Gln Asn Ile Ile
                345                 350                 355

gac aac cag aag tac tca gtt gca gac att gag cga ata aat cat gaa     1220
Asp Asn Gln Lys Tyr Ser Val Ala Asp Ile Glu Arg Ile Asn His Glu
            360                 365                 370

aga aat gaa ttg cag cag act att aat aaa tta acc aag gac ctg gaa     1268
Arg Asn Glu Leu Gln Gln Thr Ile Asn Lys Leu Thr Lys Asp Leu Glu
        375                 380                 385

gct gaa caa cag aag ttg tgg aat gag gag tta aaa tat gcc aga ggc     1316
Ala Glu Gln Gln Lys Leu Trp Asn Glu Glu Leu Lys Tyr Ala Arg Gly
    390                 395                 400

aaa gaa gcg att gaa aca caa tta gca gag tat cac aaa ttg gct aga     1364
Lys Glu Ala Ile Glu Thr Gln Leu Ala Glu Tyr His Lys Leu Ala Arg
405                 410                 415                 420

aaa tta aaa ctt att cct aaa ggt gct gag aat tcc aaa ggt tat gac     1412
Lys Leu Lys Leu Ile Pro Lys Gly Ala Glu Asn Ser Lys Gly Tyr Asp
                425                 430                 435

ttt gaa att aag ttt aat ccc gag gct ggt gcc aac tgc ctt gtc aaa     1460
Phe Glu Ile Lys Phe Asn Pro Glu Ala Gly Ala Asn Cys Leu Val Lys
            440                 445                 450

tac agg gct caa gtt tat gta cct ctt aag gaa ctc ctg aat gaa act     1508
Tyr Arg Ala Gln Val Tyr Val Pro Leu Lys Glu Leu Leu Asn Glu Thr
        455                 460                 465

gaa gaa gaa att aat aaa gcc cta aat aaa aaa atg ggt ttg gag gat     1556
Glu Glu Glu Ile Asn Lys Ala Leu Asn Lys Lys Met Gly Leu Glu Asp
```

```
    470                 475                 480

act tta gaa caa ttg aat gca atg ata aca gaa agc aag aga agt gtg     1604
Thr Leu Glu Gln Leu Asn Ala Met Ile Thr Glu Ser Lys Arg Ser Val
485                 490                 495                 500

aga act ctg aaa gaa gaa gtt caa aag ctg gat gat ctt tac caa caa     1652
Arg Thr Leu Lys Glu Glu Val Gln Lys Leu Asp Asp Leu Tyr Gln Gln
                505                 510                 515

aaa att aag gaa gca gag gaa gag gat gaa aaa tgt gcc agt gag ctt     1700
Lys Ile Lys Glu Ala Glu Glu Glu Asp Glu Lys Cys Ala Ser Glu Leu
            520                 525                 530

gag tcc ttg gag aaa cac aag cac ctg cta gaa agt act gtt aac cag     1748
Glu Ser Leu Glu Lys His Lys His Leu Leu Glu Ser Thr Val Asn Gln
        535                 540                 545

ggg ctc agt gaa gct atg aat gaa tta gat gct gtt cag cgg gaa tac     1796
Gly Leu Ser Glu Ala Met Asn Glu Leu Asp Ala Val Gln Arg Glu Tyr
    550                 555                 560

caa cta gtt gtg caa acc acg act gaa gaa aga cga aaa gtg gga aat     1844
Gln Leu Val Val Gln Thr Thr Thr Glu Glu Arg Arg Lys Val Gly Asn
565                 570                 575                 580

aac ttg caa cgt ctg tta gag atg gtt gct aca cat gtt ggg tct gta     1892
Asn Leu Gln Arg Leu Leu Glu Met Val Ala Thr His Val Gly Ser Val
                585                 590                 595

gag aaa cat ctt gag gag cag att gct aaa gtt gat aga gaa tat gaa     1940
Glu Lys His Leu Glu Glu Gln Ile Ala Lys Val Asp Arg Glu Tyr Glu
            600                 605                 610

gaa tgc atg tca gaa gat ctc tcg gaa aat att aaa gag att aga gat     1988
Glu Cys Met Ser Glu Asp Leu Ser Glu Asn Ile Lys Glu Ile Arg Asp
        615                 620                 625

aag tat gag aag aaa gct act cta att aag tct tct gaa gaa tga         2033
Lys Tyr Glu Lys Lys Ala Thr Leu Ile Lys Ser Ser Glu Glu
    630                 635                 640

agataaaatg ttgatcatgt atatatatcc atagtgaata aaattgtctc agtaaaaaaa   2093

aaaaaaaaaa aaaaaaaaaa aaaaaaaaaa aaaaaaaaaa aaaaaaaaaa aaaaaaa      2150


<210> SEQ ID NO 32
<211> LENGTH: 642
<212> TYPE: PRT
<213> ORGANISM: Homo sapiens

<400> SEQUENCE: 32

Met Lys Arg Ser Ser Val Ser Ser Gly Gly Ala Gly Arg Leu Ser Met
1               5                   10                  15

Gln Glu Leu Arg Ser Gln Asp Val Asn Lys Gln Gly Leu Tyr Thr Pro
            20                  25                  30

Gln Thr Lys Glu Lys Pro Thr Phe Gly Lys Leu Ser Ile Asn Lys Pro
        35                  40                  45

Thr Ser Glu Arg Lys Val Ser Leu Phe Gly Lys Arg Thr Ser Gly His
    50                  55                  60

Gly Ser Arg Asn Ser Gln Leu Gly Ile Phe Ser Ser Ser Glu Lys Ile
65                  70                  75                  80

Lys Asp Pro Arg Pro Leu Asn Asp Lys Ala Phe Ile Gln Gln Cys Ile
                85                  90                  95

Arg Gln Leu Cys Glu Phe Leu Thr Glu Asn Gly Tyr Ala His Asn Val
            100                 105                 110

Ser Met Lys Ser Leu Gln Ala Pro Ser Val Lys Asp Phe Leu Lys Ile
        115                 120                 125

Phe Thr Phe Leu Tyr Gly Phe Leu Cys Pro Ser Tyr Glu Leu Pro Asp
    130                 135                 140
```

-continued

```
Thr Lys Phe Glu Glu Glu Val Pro Arg Ile Phe Lys Asp Leu Gly Tyr
145                 150                 155                 160

Pro Phe Ala Leu Ser Lys Ser Ser Met Tyr Thr Val Gly Ala Pro His
                165                 170                 175

Thr Trp Pro His Ile Val Ala Ala Leu Val Trp Leu Ile Asp Cys Ile
            180                 185                 190

Lys Ile His Thr Ala Met Lys Glu Ser Ser Pro Leu Phe Asp Asp Gly
        195                 200                 205

Gln Pro Trp Gly Glu Glu Thr Glu Asp Gly Ile Met His Asn Lys Leu
    210                 215                 220

Phe Leu Asp Tyr Thr Ile Lys Cys Tyr Glu Ser Phe Met Ser Gly Ala
225                 230                 235                 240

Asp Ser Phe Asp Glu Met Asn Ala Glu Leu Gln Ser Lys Leu Lys Asp
                245                 250                 255

Leu Phe Asn Val Asp Ala Phe Lys Leu Glu Ser Leu Glu Ala Lys Asn
            260                 265                 270

Arg Ala Leu Asn Glu Gln Ile Ala Arg Leu Glu Gln Glu Arg Glu Lys
        275                 280                 285

Glu Pro Asn Arg Leu Glu Ser Leu Arg Lys Leu Lys Ala Ser Leu Gln
    290                 295                 300

Gly Asp Val Gln Lys Tyr Gln Ala Tyr Met Ser Asn Leu Glu Ser His
305                 310                 315                 320

Ser Ala Ile Leu Asp Gln Lys Leu Asn Gly Leu Asn Glu Glu Ile Ala
                325                 330                 335

Arg Val Glu Leu Glu Cys Glu Thr Ile Lys Gln Glu Asn Thr Arg Leu
            340                 345                 350

Gln Asn Ile Ile Asp Asn Gln Lys Tyr Ser Val Ala Asp Ile Glu Arg
        355                 360                 365

Ile Asn His Glu Arg Asn Glu Leu Gln Gln Thr Ile Asn Lys Leu Thr
    370                 375                 380

Lys Asp Leu Glu Ala Glu Gln Gln Lys Leu Trp Asn Glu Glu Leu Lys
385                 390                 395                 400

Tyr Ala Arg Gly Lys Glu Ala Ile Glu Thr Gln Leu Ala Glu Tyr His
                405                 410                 415

Lys Leu Ala Arg Lys Leu Lys Leu Ile Pro Lys Gly Ala Glu Asn Ser
            420                 425                 430

Lys Gly Tyr Asp Phe Glu Ile Lys Phe Asn Pro Glu Ala Gly Ala Asn
        435                 440                 445

Cys Leu Val Lys Tyr Arg Ala Gln Val Tyr Val Pro Leu Lys Glu Leu
    450                 455                 460

Leu Asn Glu Thr Glu Glu Glu Ile Asn Lys Ala Leu Asn Lys Lys Met
465                 470                 475                 480

Gly Leu Glu Asp Thr Leu Glu Gln Leu Asn Ala Met Ile Thr Glu Ser
                485                 490                 495

Lys Arg Ser Val Arg Thr Leu Lys Glu Glu Val Gln Lys Leu Asp Asp
            500                 505                 510

Leu Tyr Gln Gln Lys Ile Lys Glu Ala Glu Glu Glu Asp Glu Lys Cys
        515                 520                 525

Ala Ser Glu Leu Glu Ser Leu Glu Lys His Lys His Leu Leu Glu Ser
    530                 535                 540

Thr Val Asn Gln Gly Leu Ser Glu Ala Met Asn Glu Leu Asp Ala Val
545                 550                 555                 560

Gln Arg Glu Tyr Gln Leu Val Val Gln Thr Thr Thr Glu Glu Arg Arg
```

```
                565                 570                 575

Lys Val Gly Asn Asn Leu Gln Arg Leu Leu Glu Met Val Ala Thr His
            580                 585                 590

Val Gly Ser Val Glu Lys His Leu Glu Glu Gln Ile Ala Lys Val Asp
        595                 600                 605

Arg Glu Tyr Glu Glu Cys Met Ser Glu Asp Leu Ser Glu Asn Ile Lys
    610                 615                 620

Glu Ile Arg Asp Lys Tyr Glu Lys Lys Ala Thr Leu Ile Lys Ser Ser
625                 630                 635                 640

Glu Glu


<210> SEQ ID NO 33
<211> LENGTH: 2067
<212> TYPE: DNA
<213> ORGANISM: Homo sapiens
<220> FEATURE:
<221> NAME/KEY: CDS
<222> LOCATION: (386)..(1777)

<400> SEQUENCE: 33

tggcggaatg gggcgggact tccagtagga ggcggcaagt ttgaaaagtg atgacggttg      60

acgtttgctg atttttgact ttgcttgtag ctgctccccg aactcgccgt cttcctgtcg     120

gcggccggca ctgtaggagc tcaaactatg tagttggaaa gtgtcttcat ctctcgttaa     180

tgaataaatt gtaactgaaa ttgtacttcg aaagaatgat agaatttgga tattggagga     240

ggttccaaaa ggaaatactg gaagtttggg aaagttagga gactaacttg gagcagaaat     300

ttcattcaat tattaaaggg tttagaagcc tagcagaaaa atttgaattt gatgtggtgg     360

gtaagattaa caggaaactt ccaag atg gaa act ttg tct ttc ccc aga tat       412
                            Met Glu Thr Leu Ser Phe Pro Arg Tyr
                            1               5

aat gta gct gag att gtg att cat att cgc aat aag atc tta aca gga       460
Asn Val Ala Glu Ile Val Ile His Ile Arg Asn Lys Ile Leu Thr Gly
10                  15                  20                  25

gct gat ggt aaa aac ctc acc aag aat gat ctt tat cca aat cca aag       508
Ala Asp Gly Lys Asn Leu Thr Lys Asn Asp Leu Tyr Pro Asn Pro Lys
                30                  35                  40

cct gaa gtc ttg cac atg atc tac atg aga gcc tta caa ata gta tat       556
Pro Glu Val Leu His Met Ile Tyr Met Arg Ala Leu Gln Ile Val Tyr
            45                  50                  55

gga att cga ctg gaa cat ttt tac atg atg cca gtg aac tct gaa gtc       604
Gly Ile Arg Leu Glu His Phe Tyr Met Met Pro Val Asn Ser Glu Val
        60                  65                  70

atg tat cca cat tta atg gaa ggc ttc tta cca ttc agc aat tta gtt       652
Met Tyr Pro His Leu Met Glu Gly Phe Leu Pro Phe Ser Asn Leu Val
    75                  80                  85

act cat ctg gac tca ttt ttg cct atc tgc cgg gtg aat gac ttt gag       700
Thr His Leu Asp Ser Phe Leu Pro Ile Cys Arg Val Asn Asp Phe Glu
90                  95                  100                 105

act gct gat att cta tgt cca aaa gca aaa cgg aca agt cgg ttt tta       748
Thr Ala Asp Ile Leu Cys Pro Lys Ala Lys Arg Thr Ser Arg Phe Leu
                110                 115                 120

agt ggc att atc aac ttt att cac ttc aga gaa gca tgc cgt gaa acg       796
Ser Gly Ile Ile Asn Phe Ile His Phe Arg Glu Ala Cys Arg Glu Thr
            125                 130                 135

tat atg gaa ttt ctt tgg caa tat aaa tcc tct gcg gac aaa atg caa       844
Tyr Met Glu Phe Leu Trp Gln Tyr Lys Ser Ser Ala Asp Lys Met Gln
        140                 145                 150

cag tta aac gcc gca cac cag gag gca tta atg aaa ctg gag aga ctt       892
```

```
Gln Leu Asn Ala Ala His Gln Glu Ala Leu Met Lys Leu Glu Arg Leu
    155                 160                 165

gat tct gtt cca gtt gaa gag caa gaa gag ttc aag cag ctt tca gat      940
Asp Ser Val Pro Val Glu Glu Gln Glu Glu Phe Lys Gln Leu Ser Asp
170                 175                 180                 185

gga att cag gag cta caa caa tca cta aat cag gat ttt cat caa aaa      988
Gly Ile Gln Glu Leu Gln Gln Ser Leu Asn Gln Asp Phe His Gln Lys
                190                 195                 200

acg ata gtg ctg caa gag gga aat tcc caa aag aag tca aat att tca     1036
Thr Ile Val Leu Gln Glu Gly Asn Ser Gln Lys Lys Ser Asn Ile Ser
            205                 210                 215

gag aaa acc aag cgt ttg aat gaa cta aaa ttg ttg gtg gtt tct ttg     1084
Glu Lys Thr Lys Arg Leu Asn Glu Leu Lys Leu Leu Val Val Ser Leu
        220                 225                 230

aaa gaa ata caa gag agt ttg aaa aca aaa att gtg gat tct cca gag     1132
Lys Glu Ile Gln Glu Ser Leu Lys Thr Lys Ile Val Asp Ser Pro Glu
    235                 240                 245

aag tta aag aat tat aaa gaa aaa atg aaa gat acg gtc cag aag ctt     1180
Lys Leu Lys Asn Tyr Lys Glu Lys Met Lys Asp Thr Val Gln Lys Leu
250                 255                 260                 265

aaa aat gcc aga caa gaa gtg gtg gag aaa tat gaa atc tat gga gac     1228
Lys Asn Ala Arg Gln Glu Val Val Glu Lys Tyr Glu Ile Tyr Gly Asp
                270                 275                 280

tca gtt gac tgc ctg cct tca tgt cag ttg gaa gtg cag tta tat caa     1276
Ser Val Asp Cys Leu Pro Ser Cys Gln Leu Glu Val Gln Leu Tyr Gln
            285                 290                 295

aag aaa ata cag gac ctt tca gat aat agg gaa aaa tta gcc agt atc     1324
Lys Lys Ile Gln Asp Leu Ser Asp Asn Arg Glu Lys Leu Ala Ser Ile
        300                 305                 310

tta aag gag agc ctg aac ttg gag gac caa att gag agt gat gag tca     1372
Leu Lys Glu Ser Leu Asn Leu Glu Asp Gln Ile Glu Ser Asp Glu Ser
    315                 320                 325

gaa ctg aag aaa ttg aag act gaa gaa aat tcg ttc aaa aga ctg atg     1420
Glu Leu Lys Lys Leu Lys Thr Glu Glu Asn Ser Phe Lys Arg Leu Met
330                 335                 340                 345

att gtg aag aag gaa aaa ctt gcc aca gca caa ttc aaa ata aat aag     1468
Ile Val Lys Lys Glu Lys Leu Ala Thr Ala Gln Phe Lys Ile Asn Lys
                350                 355                 360

aag cat gaa gat gtt aag caa tac aaa cgc aca gta att gag gat tgc     1516
Lys His Glu Asp Val Lys Gln Tyr Lys Arg Thr Val Ile Glu Asp Cys
            365                 370                 375

aat aaa gtt caa gaa aaa aga ggt gct gtc tat gaa cga gta acc aca     1564
Asn Lys Val Gln Glu Lys Arg Gly Ala Val Tyr Glu Arg Val Thr Thr
        380                 385                 390

att aat caa gaa atc caa aaa att aaa ctt gga att caa caa cta aaa     1612
Ile Asn Gln Glu Ile Gln Lys Ile Lys Leu Gly Ile Gln Gln Leu Lys
    395                 400                 405

gat gct gct gaa agg gag aaa ctg aag tcc cag gaa ata ttt cta aac     1660
Asp Ala Ala Glu Arg Glu Lys Leu Lys Ser Gln Glu Ile Phe Leu Asn
410                 415                 420                 425

ttg aaa act gct ttg gag aaa tac cac gac ggt att gaa aag gca gca     1708
Leu Lys Thr Ala Leu Glu Lys Tyr His Asp Gly Ile Glu Lys Ala Ala
                430                 435                 440

gag gac tcc tat gct aag ata gat gag aag aca gct gaa ctg aag agg     1756
Glu Asp Ser Tyr Ala Lys Ile Asp Glu Lys Thr Ala Glu Leu Lys Arg
            445                 450                 455

aag atg ttc aaa atg tca acc tgattaacaa aattacatgt ctttttgtaa        1807
Lys Met Phe Lys Met Ser Thr
        460

atggcttgcc atcttttaat ttctatttta gaaagaaaag ttgaagcgaa tggaagtatc   1867
```

```
agaagtacca aataatgttg gcttcatcag tttttataca ctctcataag tagttaataa   1927

gatgaattta atgtaggctt ttattaattt ataattaaaa taacttgtgc agctattcat   1987

gtctctactc tgccccttgt tgtaaatagt ttgagtaaaa caaaactagt tacctttgaa   2047

atatatatat tttttctgt                                                 2067


<210> SEQ ID NO 34
<211> LENGTH: 464
<212> TYPE: PRT
<213> ORGANISM: Homo sapiens

<400> SEQUENCE: 34

Met Glu Thr Leu Ser Phe Pro Arg Tyr Asn Val Ala Glu Ile Val Ile
1               5                   10                  15

His Ile Arg Asn Lys Ile Leu Thr Gly Ala Asp Gly Lys Asn Leu Thr
            20                  25                  30

Lys Asn Asp Leu Tyr Pro Asn Pro Lys Pro Glu Val Leu His Met Ile
        35                  40                  45

Tyr Met Arg Ala Leu Gln Ile Val Tyr Gly Ile Arg Leu Glu His Phe
    50                  55                  60

Tyr Met Met Pro Val Asn Ser Glu Val Met Tyr Pro His Leu Met Glu
65                  70                  75                  80

Gly Phe Leu Pro Phe Ser Asn Leu Val Thr His Leu Asp Ser Phe Leu
                85                  90                  95

Pro Ile Cys Arg Val Asn Asp Phe Glu Thr Ala Asp Ile Leu Cys Pro
            100                 105                 110

Lys Ala Lys Arg Thr Ser Arg Phe Leu Ser Gly Ile Ile Asn Phe Ile
        115                 120                 125

His Phe Arg Glu Ala Cys Arg Glu Thr Tyr Met Glu Phe Leu Trp Gln
    130                 135                 140

Tyr Lys Ser Ser Ala Asp Lys Met Gln Gln Leu Asn Ala Ala His Gln
145                 150                 155                 160

Glu Ala Leu Met Lys Leu Glu Arg Leu Asp Ser Val Pro Val Glu Glu
                165                 170                 175

Gln Glu Glu Phe Lys Gln Leu Ser Asp Gly Ile Gln Glu Leu Gln Gln
            180                 185                 190

Ser Leu Asn Gln Asp Phe His Gln Lys Thr Ile Val Leu Gln Glu Gly
        195                 200                 205

Asn Ser Gln Lys Lys Ser Asn Ile Ser Glu Lys Thr Lys Arg Leu Asn
    210                 215                 220

Glu Leu Lys Leu Leu Val Val Ser Leu Lys Glu Ile Gln Glu Ser Leu
225                 230                 235                 240

Lys Thr Lys Ile Val Asp Ser Pro Glu Lys Leu Lys Asn Tyr Lys Glu
                245                 250                 255

Lys Met Lys Asp Thr Val Gln Lys Leu Lys Asn Ala Arg Gln Glu Val
            260                 265                 270

Val Glu Lys Tyr Glu Ile Tyr Gly Asp Ser Val Asp Cys Leu Pro Ser
        275                 280                 285

Cys Gln Leu Glu Val Gln Leu Tyr Gln Lys Lys Ile Gln Asp Leu Ser
    290                 295                 300

Asp Asn Arg Glu Lys Leu Ala Ser Ile Leu Lys Glu Ser Leu Asn Leu
305                 310                 315                 320

Glu Asp Gln Ile Glu Ser Asp Glu Ser Glu Leu Lys Lys Leu Lys Thr
                325                 330                 335
```

```
Glu Glu Asn Ser Phe Lys Arg Leu Met Ile Val Lys Lys Glu Lys Leu
            340                 345                 350

Ala Thr Ala Gln Phe Lys Ile Asn Lys Lys His Glu Asp Val Lys Gln
        355                 360                 365

Tyr Lys Arg Thr Val Ile Glu Asp Cys Asn Lys Val Gln Glu Lys Arg
    370                 375                 380

Gly Ala Val Tyr Glu Arg Val Thr Thr Ile Asn Gln Glu Ile Gln Lys
385                 390                 395                 400

Ile Lys Leu Gly Ile Gln Gln Leu Lys Asp Ala Ala Glu Arg Glu Lys
                405                 410                 415

Leu Lys Ser Gln Glu Ile Phe Leu Asn Leu Lys Thr Ala Leu Glu Lys
            420                 425                 430

Tyr His Asp Gly Ile Glu Lys Ala Ala Glu Asp Ser Tyr Ala Lys Ile
        435                 440                 445

Asp Glu Lys Thr Ala Glu Leu Lys Arg Lys Met Phe Lys Met Ser Thr
    450                 455                 460


<210> SEQ ID NO 35
<211> LENGTH: 19
<212> TYPE: PRT
<213> ORGANISM: artificial
<220> FEATURE:
<223> OTHER INFORMATION: CDCA1-KNTC2 binging region  peptide sequence

<400> SEQUENCE: 35

Ile Gln Lys Ile Lys Leu Gly Ile Gln Gln Leu Lys Asp Ala Ala Glu
1               5                   10                  15

Arg Glu Lys


<210> SEQ ID NO 36
<211> LENGTH: 11
<212> TYPE: PRT
<213> ORGANISM: Artificial
<220> FEATURE:
<223> OTHER INFORMATION: an artificially synthesized 11 mer
      poly-arginine sequence

<400> SEQUENCE: 36

Arg Arg Arg Arg Arg Arg Arg Arg Arg Arg Arg
1               5                   10


<210> SEQ ID NO 37
<211> LENGTH: 9
<212> TYPE: PRT
<213> ORGANISM: Artificial
<220> FEATURE:
<223> OTHER INFORMATION: an artificially synthesized Tat sequence

<400> SEQUENCE: 37

Arg Lys Lys Arg Arg Gln Arg Arg Arg
1               5


<210> SEQ ID NO 38
<211> LENGTH: 16
<212> TYPE: PRT
<213> ORGANISM: Artificial
<220> FEATURE:
<223> OTHER INFORMATION: an artificially synthesized Penetratin
      sequence

<400> SEQUENCE: 38

Arg Gln Ile Lys Ile Trp Phe Gln Asn Arg Arg Met Lys Trp Lys Lys
1               5                   10                  15
```

```
<210> SEQ ID NO 39
<211> LENGTH: 21
<212> TYPE: PRT
<213> ORGANISM: Artificial
<220> FEATURE:
<223> OTHER INFORMATION: an artificially synthesized Buforin II
      sequence

<400> SEQUENCE: 39

Thr Arg Ser Ser Arg Ala Gly Leu Gln Phe Pro Val Gly Arg Val His
1               5                   10                  15

Arg Leu Leu Arg Lys
            20


<210> SEQ ID NO 40
<211> LENGTH: 27
<212> TYPE: PRT
<213> ORGANISM: Artificial
<220> FEATURE:
<223> OTHER INFORMATION: an artificially synthesized Transportan
      sequence

<400> SEQUENCE: 40

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25


<210> SEQ ID NO 41
<211> LENGTH: 18
<212> TYPE: PRT
<213> ORGANISM: Artificial
<220> FEATURE:
<223> OTHER INFORMATION: an artificially synthesized MAP (model
      amphipathic peptide) seque

<400> SEQUENCE: 41

Lys Leu Ala Leu Lys Leu Ala Leu Lys Ala Leu Lys Ala Ala Leu Lys
1               5                   10                  15

Leu Ala


<210> SEQ ID NO 42
<211> LENGTH: 16
<212> TYPE: PRT
<213> ORGANISM: Artificial
<220> FEATURE:
<223> OTHER INFORMATION: an artificially synthesized K-FGF sequence

<400> SEQUENCE: 42

Ala Ala Val Ala Leu Leu Pro Ala Val Leu Leu Ala Leu Leu Ala Pro
1               5                   10                  15


<210> SEQ ID NO 43
<211> LENGTH: 5
<212> TYPE: PRT
<213> ORGANISM: Artificial
<220> FEATURE:
<223> OTHER INFORMATION: an artificially synthesized Ku70 sequence

<400> SEQUENCE: 43

Val Pro Met Leu Lys
1               5


<210> SEQ ID NO 44
<211> LENGTH: 28
<212> TYPE: PRT
```

```
<213> ORGANISM: Artificial
<220> FEATURE:
<223> OTHER INFORMATION: an artificially synthesized Prion sequence

<400> SEQUENCE: 44

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25


<210> SEQ ID NO 45
<211> LENGTH: 18
<212> TYPE: PRT
<213> ORGANISM: Artificial
<220> FEATURE:
<223> OTHER INFORMATION: an artificially synthesized pVEC sequence

<400> SEQUENCE: 45

Leu Leu Ile Ile Leu Arg Arg Arg Ile Arg Lys Gln Ala His Ala His
1               5                   10                  15

Ser Lys


<210> SEQ ID NO 46
<211> LENGTH: 21
<212> TYPE: PRT
<213> ORGANISM: Artificial
<220> FEATURE:
<223> OTHER INFORMATION: an artificially synthesized Pep-1 sequence

<400> SEQUENCE: 46

Lys Glu Thr Trp Trp Glu Thr Trp Trp Thr Glu Trp Ser Gln Pro Lys
1               5                   10                  15

Lys Lys Arg Lys Val
            20


<210> SEQ ID NO 47
<211> LENGTH: 18
<212> TYPE: PRT
<213> ORGANISM: Artificial
<220> FEATURE:
<223> OTHER INFORMATION: an artificially synthesized SynB1 sequence

<400> SEQUENCE: 47

Arg Gly Gly Arg Leu Ser Tyr Ser Arg Arg Arg Phe Ser Thr Ser Thr
1               5                   10                  15

Gly Arg


<210> SEQ ID NO 48
<211> LENGTH: 15
<212> TYPE: PRT
<213> ORGANISM: Artificial
<220> FEATURE:
<223> OTHER INFORMATION: an artificially synthesized Pep-7 sequence

<400> SEQUENCE: 48

Ser Asp Leu Trp Glu Met Met Met Val Ser Leu Ala Cys Gln Tyr
1               5                   10                  15


<210> SEQ ID NO 49
<211> LENGTH: 12
<212> TYPE: PRT
<213> ORGANISM: Artificial
<220> FEATURE:
<223> OTHER INFORMATION: an artificially synthesized HN-1 sequence

<400> SEQUENCE: 49
```

```
Thr Ser Pro Leu Asn Ile His Asn Gly Gln Lys Leu
1               5                   10


<210> SEQ ID NO 50
<211> LENGTH: 5
<212> TYPE: PRT
<213> ORGANISM: Artificial
<220> FEATURE:
<223> OTHER INFORMATION: Artificialy synthesized Ku70 PMLKE sequence

<400> SEQUENCE: 50

Pro Met Leu Lys Glu
1               5
```